US012662670B2

(12) United States Patent
Cook et al.

(10) Patent No.: US 12,662,670 B2
(45) Date of Patent: Jun. 23, 2026

(54) SHORT MULTI-REPEAT RNA TARGETING GENE SILENCING

(71) Applicant: Kansas State University Research Foundation, Manhattan, KS (US)

(72) Inventors: David E. Cook, Manhattan, KS (US); Veerendra Sharma, Manhattan, KS (US); Sandeep Marla, Manhattan, KS (US); Geoffrey Morris, Fort Collins, CO (US)

(73) Assignee: Kansas State University Research Foundation, Manhattan, KS (US)

( * ) Notice: Subject to any disclaimer, the term of this patent is extended or adjusted under 35 U.S.C. 154(b) by 182 days.

(21) Appl. No.: 18/555,161

(22) PCT Filed: Apr. 14, 2022

(86) PCT No.: PCT/US2022/024863
§ 371 (c)(1),
(2) Date: Oct. 12, 2023

(87) PCT Pub. No.: WO2022/245454
PCT Pub. Date: Nov. 24, 2022

(65) Prior Publication Data
US 2024/0182899 A1 Jun. 6, 2024

Related U.S. Application Data

(60) Provisional application No. 63/174,832, filed on Apr. 14, 2021.

(51) Int. Cl.
*C12N 15/11* (2006.01)
*C12N 15/113* (2010.01)
*C12N 15/82* (2006.01)

(52) U.S. Cl.
CPC ........ *C12N 15/113* (2013.01); *C12N 15/8216* (2013.01); *C12N 2310/11* (2013.01)

(58) Field of Classification Search
None
See application file for complete search history.

(56) References Cited

U.S. PATENT DOCUMENTS 10,724,049 B2 7/2020 Jin
2019/0352652 A1* 11/2019 Abudayyeh ........ C12N 15/8283

FOREIGN PATENT DOCUMENTS

WO 2021051630 7/2001
WO 2017219027 12/2017
WO 2020210705 10/2020
WO WO-2020210705 A1 * 10/2020 ........... C12N 15/907

OTHER PUBLICATIONS

International Search Report and Written Opinion in corresponding PCT/US2022/024863, dated Feb. 13, 2023.
Abudayyeh, et al., "C2c2 is a single-component programmable RNA-guided RNA-targeting CRISPR effector", Science, 2016, 353(6299).
Konermann, et al., "Transcriptome Engineering with RNA-Targeting Type VI-D CRISPR Effectors", Cell, 2018, 173(3), pp. 665-676.
Qiao, et al. Spray-induced gene silencing for disease control is dependent on the efficiency of pathogen RNA uptake, vol. 19, Issue9, Mar. 17, 2021, pp. 1756-1768.
Sharma, et al., "CRISPR guides induce gene silencing in plants in the absence of Cas," Genome Biology (2022) 23:6, Published online Jan. 3, 2022.
Wang et al., "Bidirectional cross-kingdom RNAi and fungal uptake of external RNAs confer plant protection," Nat Plants. ; 2: 16151, Mar. 19, 2017.

* cited by examiner

*Primary Examiner* — Weihua Fan
(74) *Attorney, Agent, or Firm* — Hovey Williams LLP; Crissa A. Cook

(57) ABSTRACT

Short multi-repeat RNA targeting constructs for manipulating RNA targets and obtaining variable levels of gene silencing, and methods of using the same to silence RNA targets in mammals, insects, plants, and fungus. The constructs comprise two or more distinct guide nucleotide sequences (in the absence of CRISPR nuclease) that are complementary to one or more RNA targets, wherein each guide nucleotide sequence consists of a single-stranded antisense nucleotide fragment of 100 nt or less.

19 Claims, 27 Drawing Sheets

Specification includes a Sequence Listing.

a
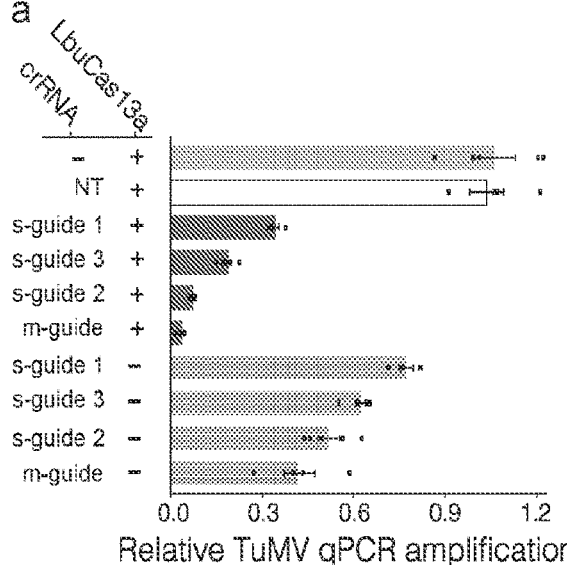
Relative TuMV qPCR amplification
b
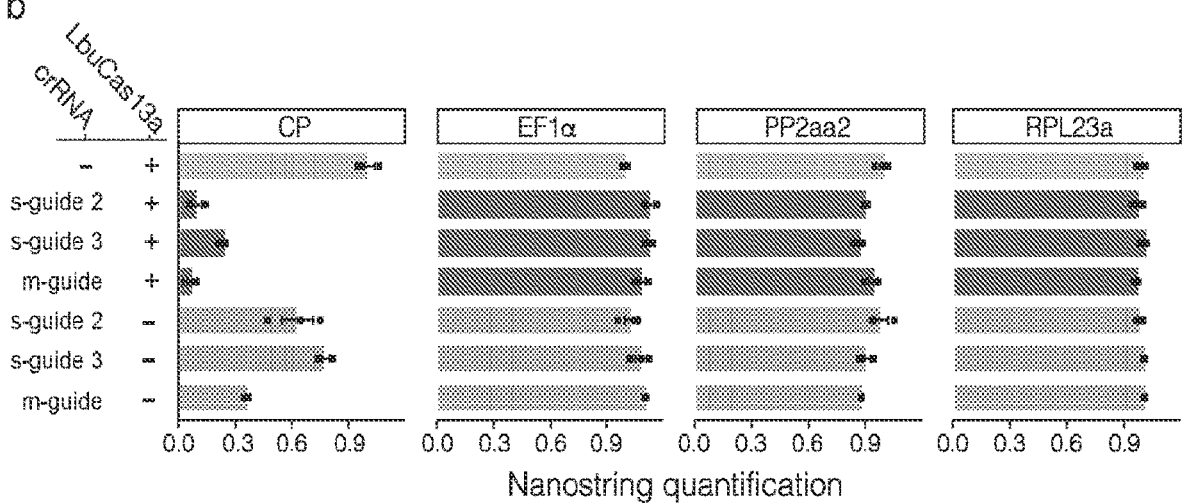
Nanostring quantification
FIG. 6

Guide crRNA targeting Phytoene desaturase (PDS)
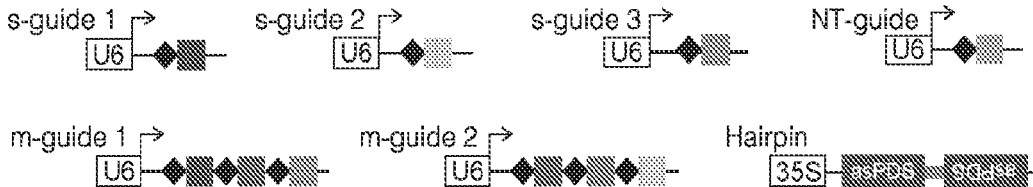
Guide targeting location on PDS transcript
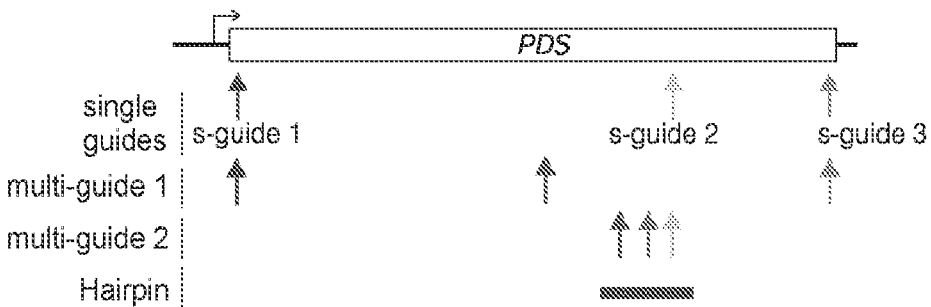
FIG. 8 a
Cas13   ‑   +   +   +   +   +   +   ‑   ‑   ‑   ‑   ‑
guide   ‑   ‑   NT   1   2   3   M   1   2   3   M   H
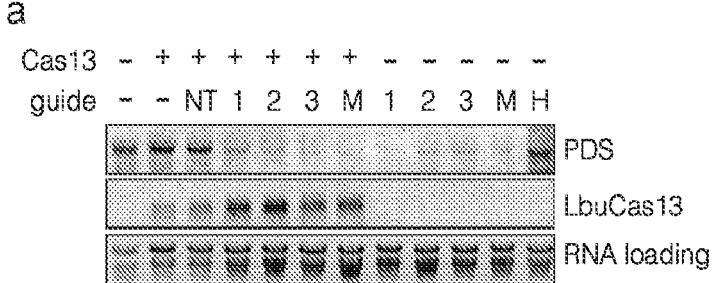
PDS
LbuCas13
RNA loading
b
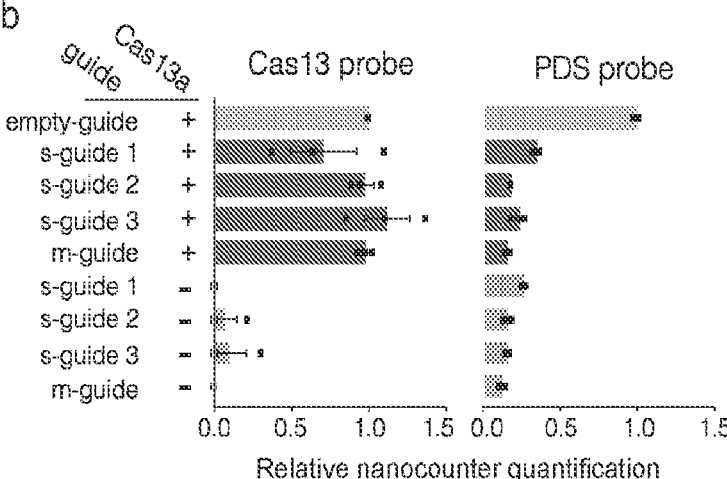
Relative nanocounter quantification
FIG. 9

Tobacco Rattle Virus
cloning and expression
vectors.

TRV is agroinfiltrated
into bottom leaves of
*N. benthamiana.*

TRV spreads systemically,
delivering guide crRNA
and inducing photobleaching.

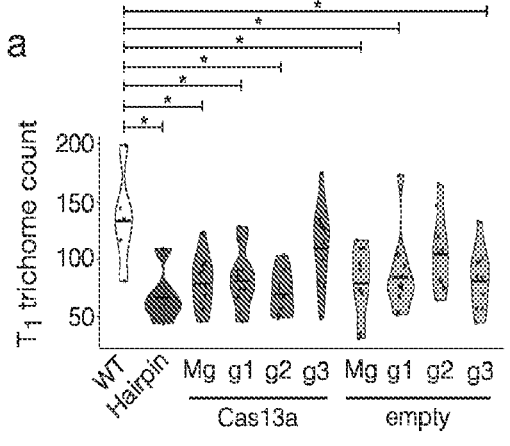
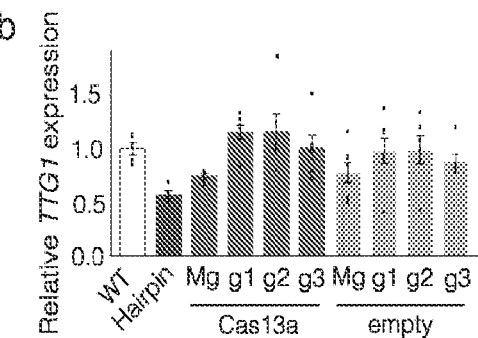
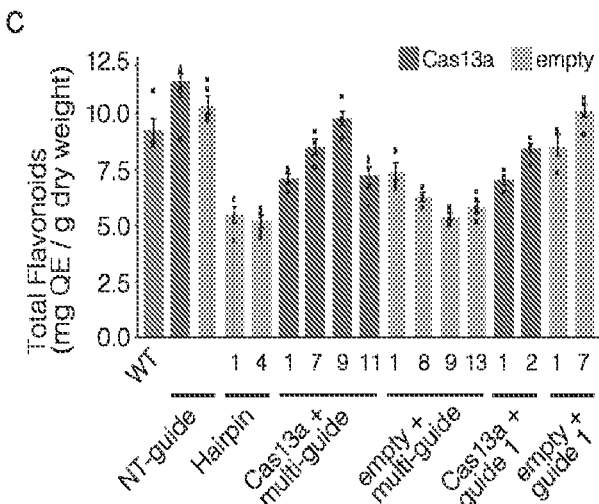
FIG. 12

Multi-guide 1 crRNA design

Guide target location on PDS transcript

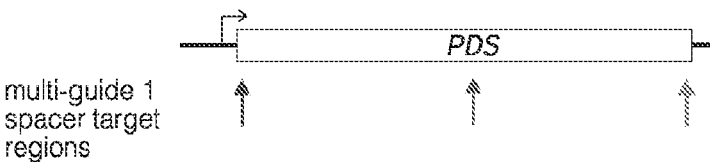

multi-guide 1
spacer target
regions m-guide 1, crRNA 1 sequence

| | | |
|---|---|---|
| m-guide 1 | GTCCAATTTGGGGCATTTTATTGAACAA | (SEQ 24) |
| m-guide 1 [mm5,6] | GTCCATTTGGGGCATTTTATTGAACAA | (SEQ 30) |
| m-guide 1 [mm10,11] | GTCCAATTTGGCATTTTATTGAACAA | (SEQ 31) |
| m-guide 1 [mm21,22] | GTCCAATTTGGGGCATTTTAGAACAA | (SEQ 32) |

```
**   *  ******  ****
``` m-guide 1, crRNA 2 sequence

| | | |
|---|---|---|
| m-guide 1 | TCGAAAGCTCGTCAGGGTTTATGAAGTT | (SEQ 25) |
| m-guide 1 [mm5,6] | TCGAGCTCGTCAGGGTTTATGAAGTT | (SEQ 30) |
| m-guide 1 [mm10,11] | TCGAAAGCTTCAGGGTTTATGAAGTT | (SEQ 31) |
| m-guide 1 [mm21,22] | TCGAAGCTCGTCAGGGTTTGAAGTT | (SEQ 32) |

```
**   *  ******  ****
``` m-guide 1, crRNA 3 sequence

| | | |
|---|---|---|
| m-guide 1 | GAAGTAACTCGTAATCCTGTACAATAGC | (SEQ 26) |
| m-guide 1 [mm5,6] | GAAGACTCGTAATCCTGTACAATAGC | (SEQ 30) |
| m-guide 1 [mm10,11] | GAAGTAACTTAATCCTGTACAATAGC | (SEQ 31) |
| m-guide 1 [mm21,22] | GAAGTAACTCGTAATCCTGTAATAGC | (SEQ 32) |

PDS spacer crRNA sequence    PAM (SEQ 34) sgRNA 1       tracrRNA 78 bp     109 bp (SEQ 35) sgRNA 1 [50%mm]       tracrRNA 78 bp     109 bp (SEQ 26) s-guide 1       Lbu Direct Repeat (DR) 37 bp     65 bp

\* \* \* \* \* \* \* \* \* \* \* \* \* b numeric denotes the independent lines; Red numeric denotes clear reduction numeric denotes the independent lines; Red numeric denotes clear reduction

SHORT MULTI-REPEAT RNA TARGETING GENE SILENCING

CROSS-REFERENCE TO RELATED APPLICATIONS

The present application is the U.S. National Stage of International Patent Application No. PCT/US2022/024863, filed Apr. 14, 2022, which claims the priority benefit of U.S. Provisional Patent Application Ser. No. 63/174,832, filed Apr. 14, 2021, entitled GUIDE-INDUCED GENE SILENCING (GIGS), each of which is incorporated by reference in its entirety herein.

FEDERALLY SPONSORED RESEARCH OR DEVELOPMENT

This invention was made with government support under grant no. D17AP00034 awarded by the Defense Advanced Research Projects Agency. The government has certain rights in the invention.

SEQUENCE LISTING

The following application contains a sequence listing in computer readable format (CRF), submitted via EFS-Web as an ASCII text file entitled "Sequence_Listing," created on Apr. 13, 2022, as 98,100 bytes, to serve as both the paper copy and CRF in compliance with 37 C.F.R. 1.821. The content of the ASCII text file is hereby incorporated by reference herein.

BACKGROUND OF THE INVENTION

Field of the Invention

The present invention relates to new RNA knockdown technology in which guide crRNA silences endogenous genes in the absence of the traditional CRISPR nuclease proteins, and offers a potential cis-genic solution for transcriptome engineering in plants and other organisms.

Description of Related Art

New technological advances are needed to meet 21st century agricultural demands. The development of the clustered regularly interspaced short palindromic repeat (CRISPR) and associated proteins (Cas enzymes) for DNA editing holds significant promise to help increase agricultural productivity. However, targeting and editing DNA has limitations for multigene traits and cannot provide RNA-virus resistance. The editing of DNA may result in unintended and unpredictable pleiotropic phenotypes due to wide spatiotemporal gene function. Additionally, many target traits for improvement are polygenic in nature, and multi-gene genome editing will compound the problem of generating unpredictable and unwanted phenotypes.

CRISPR systems have been developed for various Cas proteins (Cas9, Cas12, Cas13) and have since been modified for RNA targeting, whereby the guide sequence directs the enzyme to edit a complementary RNA strand of the target. Cas13 (formerly C2C2) is a single effector recently identified in type VI CRISPR systems for RNA-guided RNA-interfering activity. See U.S. Patent Pub. No. 2019/035997, filed Jun. 19, 2017, and incorporated by reference herein in its entirety. Existing RNA interference (RNAi) technologies, which enable cleavage or inhibition of desired transcripts, have significant off-target effects and remain challenging for engineering targets.

SUMMARY

As an alternative technology, we have developed a programmable RNA-guided targeting system based upon the CRISPR Cas guide platform, but which avoids the use of the CRISPR nuclease altogether, and the use of RNA sequences related to CRISPR. Thus, it does not require the introduction of "foreign" (i.e., bacterial) nucleic acids and therefore does not implicate the same issues as traditional transgenic technology. In general, the system involves nucleic acid constructs comprising short multiple repeat single stranded antisense sequences that are complementary to a target locus (either directly complementary or encode for the complementary antisense fragment). The guide sequences can be complementary to an endogenous target site of the host organism. Alternatively, the guide sequences can be complementary to an RNA target for an RNA virus that has infected the host organism. High levels of silencing of the target RNA are observed through the use of multiple repeat fragments of the guide sequence, leading to degradation of the target RNA and corresponding reduction of transcripts and thus downstream products. Unlike conventional CRISPR vectors, the construct does not include a second nucleotide sequence encoding for a CRISPR nuclease.

The platform is demonstrated initially using two Cas13a systems from *Leptotrichia buccalis* (Lbu) and *Lachnospiraceae bacterium* (Lba) as a platform for targeting trans, endogenous and viral RNA in plants. The function of the system was tested in *Nicotiana benthamiana* and *Arabidopsis thaliana* using biochemical and genomic techniques and the results show that both tested Cas13s can significantly reduce diverse target mRNAs. Unexpectedly, expressing the Cas13 CRISPR-RNA (crRNA) designed to express multiple guides provided target mRNA reduction independent of the Cas13 protein. Stable transgenic *Arabidopsis* plants have been developed to further understand this phenomenon, which has been further proved in soybean and extended to show efficacy using single-guide designed RNA related to the Cas9 system. Collectively, this research provides molecular characterization of new approaches for plant biotechnology, anti-viral resistance, and functional genomics.

The present disclosure concerns new techniques for gene silencing, in particular relying on guide RNA-alone to target RNA (instead of DNA) through target RNA degradation and without Cas enzymes traditional to CRISPR systems. The approach can be used, inter alia, to suppress plant viruses and plant endogenous transcripts as a new technique to reduce target RNA levels. The disclosure concerns expression constructs comprising single or multi-guide RNA segments or fragments. This technique was originally referred to as guide-induced gene silencing (GIGS), and relies on guide RNA sequences (or DNA sequence encoding for guide RNA) designed to be complementary to the target transcript. Guide-alone silencing can be induced using an array of anti-sense nucleotides that are separated by direct repeat loops, and other sequences, including short random nucleotide linkers. Moreover, multi-guide constructs can also include guides directly connected in the same expression cassette without intervening sequences.

Although the constructs may leverage endogenous RNAi machinery, these constructs are distinct from convention RNAi. Traditional small interfering RNA (siRNA) are usually induced by expressing a hairpin piece of RNA, typically ~200 to 800 bp of a gene that has a linker, and then the same length of gene in the reverse complement. Sometimes the transcript is a short or small hairpin RNA (shRNA) that contains a sense and antisense sequence of 19-30 nucleotides intervened by a few (~4) unpaired base pairs expressed as a single RNA molecule. This way, the one transcript has self-complementarity and folds on itself. For any design, a single transcript that has self-complementarity and forms the double-stranded RNA is introduced into the host organism or cell, and provides the signal to the endogenous machinery to initiate RNAi. Anti-sense RNA has also been used in which a transcript is expressed that is complementary to an mRNA fragment. This transcript binds to the mRNA to produce double-stranded RNA, and again, this triggers RNAi. However, antisense silencing using these approaches results in unpredictable silencing results, and is often unsuccessful unless it uses a very long piece of antisense RNA. The present technology leverages short (less than 100 nt) single-stranded, multiple repeat fragments or segments of a RNA guide sequence that is complementary to a target RNA. These short, multi-guide constructs unexpectedly demonstrate silencing of various targets in the absence of the CRISPR-Cas enzymes.

Advantages include the ability to apply precision biotechnology in crops without the use of "foreign DNA." This approach, by eliminating components previously thought critical (e.g., Cas enzymes), further simplifies the ability to impact endogenous transcripts and knock down mRNA. The use of multiple short pieces of antisense RNA, which do not necessarily need to target contiguous regions of the target RNA, provide numerous advantages, including greater flexibility for design, greater quantitative range of target RNA reduction, and fidelity for silencing, resulting in fewer off-target effects (mRNA silencing of unintended targets). The platform is also superior to traditional RNAi in that constructs can be designed to more easily target multiple genes, which is fundamental for impacting complex traits or gene families. Moreover, the compact design of the expression cassettes makes them easier to use and clone.

Although exemplified in plant systems and crop improvement, the platform could be leveraged in the control of fungal pathogens (e.g., as a fungicide targeting genes in primary metabolism or cell wall components), as an herbicide (e.g., by selectively inhibiting required pathways in hard to control weeds), and as part of a rapid-response to emergent pathogens platform. The platform can be optimized to provide spatial and temporal silencing using SMRRTs that will be a key advancement in crop biotechnology. The platform can also be paired with existing and emerging delivery platforms to introduce the expression cassettes into the target host.

In one aspect, the disclosure concerns short multi-repeat RNA targeting constructs for manipulating RNA targets, said constructs comprising two or more distinct guide nucleotide sequences that are complementary to one or more RNA targets, wherein each guide nucleotide sequence consists of a single-stranded antisense nucleotide fragment of 100 nt or less, for example, 15 nt to 100 nt, for example, 80 nt or less, for example, 50 nt or less, for example, 22 nt to 30 nt. In any one of the disclosed embodiments, the guide nucleotide sequences are guide RNA (crRNA) or DNA encoding for the guide RNA, which are capable of binding or hybridizing to the RNA target. In any one of the disclosed embodiments, the RNA target is a coding sequence, preferably mRNA or pre-mRNA, or a non-coding sequence, preferably ncRNA, lncRNA, tRNA, or rRNA. In any one of the disclosed embodiments, the guide nucleotide sequences each bind to a different region of the same RNA target. In any one of the disclosed embodiments, the different regions are not contiguous loci of said RNA target. In any one of the disclosed embodiments, the different regions are contiguous loci on said RNA target. In any one of the disclosed embodiments, the guide nucleotide sequences each bind to a different RNA target In any one of the disclosed embodiments, the constructs can be comprised within one or more expression cassettes, which is preferably a single-stranded cassette. In any one of the disclosed embodiments, the constructs can be comprised within a single expression cassette. In any one of the disclosed embodiments, the two or more distinct guide nucleotide sequences are directly linked on said expression cassette. In any one of the disclosed embodiments, the two or more distinct guide nucleotide sequences are indirectly linked, such that each guide nucleotide sequence is separated by an intervening sequence on said expression cassette. In any one of the disclosed embodiments, the intervening sequences are selected from the group consisting of regulatory elements, direct repeats, and/or non-coding sequences of 30 nt or less.

In any one of the disclosed embodiments, the single expression cassette is a homogenous multimer wherein each of said two or more distinct guide nucleotide sequences consists of the same sequence and has complementarity with the same region of the same RNA target. In any one of the disclosed embodiments, the homogenous multimer comprises up to eight repeats of the same guide nucleotide sequence.

Alternatively, in any one of the disclosed embodiments, the single expression cassette is a heterogenous multimer wherein each of said two or more distinct guide nucleotide sequences consists of different sequences having complementarity with different RNA targets or different regions of the same RNA target.

In any one of the disclosed embodiments, the constructs are located on the expression cassette adjacent at least one regulatory element. In any one of the disclosed embodiments, the constructs are configured for co-expression. In any one of the disclosed embodiments, the constructs are free of nuclease-encoding nucleotide sequences. In any one of the disclosed embodiments, the constructs are free of nuclease protein.

The disclosure also concerns compositions for manipulation of RNA targets which comprise a plurality of short multi-repeat RNA targeting constructs according to any one of the embodiments or combinations of embodiments disclosed herein, dispersed in a carrier or vehicle.

The disclosure also concerns methods of modifying an RNA target, said method comprising delivering to said RNA target short multi-repeat RNA targeting constructs according to any one of the embodiments or combinations of embodiments disclosed herein. In any one of the disclosed embodiments, the method comprises introducing said short multi-repeat RNA targeting construct into a cell, tissue, organ, or organism. In any one of the disclosed embodiments, the cell is a eukaryotic cell. In any one of the disclosed embodiments, the cell is a mammalian, plant, insect, or fungal cell. In any one of the disclosed embodiments, the organism is a mammal, plant, insect, or fungus. In any one of the disclosed embodiments, the modification of the RNA target comprises reduced expression of one or more transcripts of the RNA target. In any one of the disclosed embodiments, the modification of the RNA target comprises degradation of one or more transcripts of the RNA target. In any one of the disclosed embodiments, modifying said RNA target comprises partially or completely silencing trans or endogenous gene expression associated with said RNA target. In any one of the disclosed embodiments, the modification of the RNA target comprises altered transcription or translation of at least one RNA product. In any one of the disclosed embodiments, the expression of the at least one product is decreased. In any one of the disclosed embodiments, the RNA target is an RNA virus. In any one of the disclosed embodiments, the RNA virus has infected a mammalian, plant, insect, or fungal cell, tissue, or organism. In any one of the disclosed embodiments, the method comprises delivering said constructs to said mammalian, plant, insect, or fungal cell, tissue, or organism to treat or prevent said infection.

The disclosure also concerns methods of gene silencing comprising delivering to a cell, tissue, organ, or organism, short multi-repeat RNA targeting constructs according to any one of the embodiments or combinations of embodiments disclosed herein, wherein at least one of said two or more distinct guide nucleotide sequences is complementary to an RNA target associated with said gene.

The disclosure also concerns methods of manipulating a plant characteristic, said method comprising delivering to a plant cell, tissue, or plant short multi-repeat RNA targeting constructs according to any one of the embodiments or combinations of embodiments disclosed herein, wherein at least one of said two or more distinct guide nucleotide sequences is complementary to an RNA target associated with a gene encoding for said plant characteristic. In one or more embodiments, the plant characteristic is vigorous growth, abundant foliage, longer primary roots, yield, height, and/or shoot water potential, pest resistance, drought tolerance, heat tolerance, salt tolerance, cold resistance, herbicide resistance, fungal resistance or reduced fungal susceptibility, viral resistance, or reduced viral susceptibility. In one or more embodiments, the plant is an invasive plant or weed, wherein said plant characteristic is altered to kill said plant or render said plant susceptible to herbicides.

BRIEF DESCRIPTION OF THE DRAWINGS

FIG. 6 shows data demonstrating that CRISPR inhibits TuMV with and without the Cas13 protein. a, Quantification of TuMV accumulation from *N. benthamiana* transient spot expression. Leaves were inoculated with TuMV, and a combination of Cas13 and guide crRNA as indicated to the left of the barplot. Individual samples are shown as black dots and the mean is shown as a bar with standard error. TuMV levels were standardized to the plant endogenous EF1$\alpha$ transcript and normalized to the Cas13 alone sample. Five samples were collected for each treatment. b, Nanostring quantification for using four different probes: TuMV (Coat protein, CP), and three endogenous controls from *N. benthamiana* (EF1$\alpha$, PP2aa2, RPL23a). Samples expressed either the LbuCas13a protein (+) or no transgene (−), along with no-guide (−), a single-guide (s-guide), or a multi-guide crRNA (m-guide). Three independent samples were analyzed per treatment.

FIG. 8 provides data showing guide crRNA design and target sites for endogenous mRNA reduction by GIGS. Schematic of single- and multi-guide crRNA (s-guide and m-guide, respectively), along with control non-targeting guides (NT-guide) and RNAi inducing Hairpin. The approximate location where the respective guides are anti-sense to the PDS transcript (i.e. their target location) are denoted by filled arrows. The region covered by the hairpin construct is shown as a grey bar.

FIG. 9 provides data showing endogenous mRNA reduction mediated by Cas13-dependent and GIGS expression. a, Reduction in PDS mRNA accumulation as measured by northern blot analysis using a PDS probe (PDS panel). Samples expressing the Cas13a transcript are indicated (Cas13+) and correspond to signal from the Cas13 probe (LbuCas13 panel). Samples expressed no guide (−), a non-target guide (NT), one of three single-guides (1,2, or 3), a multi-guide (M), or a hairpin construct (H). The presence of roughly equal RNA amounts was confirmed by the abundance of ribosomal RNA signal (RNA loading panel). b, Quantification directly on RNA samples using nanostring for Cas13 (Cas13 probe) and phytoene desaturase (PDS probe) mRNA. The presence (+) or absence (−) of Cas13 expression is indicated to the left, along with the expression of a single-guide (s-guide) or the multi-guide (m-guide).

FIG. 12 shows data demonstrating that Cas13-dependent and GIGS T1 transformed *A. thaliana* lines and display phenotypes consistent with TTG1 reduction. a, Leaf trichome counts from individual T1 lines shown as black points and the distribution shown as a violin plot. Three single-guides (g1, g2, g3) or a multi-guide (Mg) were transformed into plants with Cas13a (dark blue) or without (light blue). Plants were transformed with a hairpin construct (grey) designed to silence the TTG1 transcript. Statistical comparisons to the non-transformed control (WT, wild-type) were made as one-sided Mann-Whitney U-test with Benjamini-Hochberg (BH) multiple testing correction. Samples with p-values less than 0.05 (*) are indicated. b, Five lines from each transformation group were assessed for TTG1 transcript levels using qPCR. The values were standardized to AtEF1α endogenous control and normalized to the WT control. Individual data points are shown as black points and the mean and standard deviation shown as a barplot. c, Individual T1 plants were self fertilized, and five lots of seed from each plant (technical replicates) were analyzed for seed total flavonoid content. Transformants expressing Cas13a are shown in dark blue while those not expressing Cas13a are shown in light blue. Individual data points are shown as black points and the mean and standard deviation shown as barplots: WT, wild-type; C13, Cas13a expressing; empty, no Cas13a protein; Hairpin, expressing a 197 bp hairpin against TTG1. Numbers indicate the line numbers for the indicated treatments shown below.

FIG. 14 provides data showing guide crRNA design for multi-guide 1 and three corresponding multi-guides with base pair mismatches. Schematic of multi-guide 1 (m-guide 1) expressed as a single RNA transcript from the U6 promoter. The multi-guide crRNA targets the PDS transcript at three locations, shown as three filled arrows indicating the relative position on the PDS transcript. For each of the 28 nt guide targeting sequences (crRNA 1, 2, and 3), the complementary sequence is shown (multi-g1), the guide with mismatches at position 5,6 (multi-g1[mm5,6]) (highlighted in green), the guide with mismatches at position 10,11 (multi-g1[mm10,11]) (highlighted in blue), and the guide with mismatches at position 21,22 (multi-g1[mm21,22]) (highlighted in purple). *, indicates where the four guide crRNA sequence alignments are identical.

b, Representative images of a lower leaf from *N. benthamiana* plants after two-weeks of systemic TRV delivery of transformation control (TRV$_{empty}$) and reduced guides of varying lengths (28-18 nt). c, Chlorophyll content or leaf greenness measured with SPAD meter two-weeks after systemic delivery of crRNA. d, Relative PDS levels quantified using qPCR. Statistical comparisons were made using one-way ANOVA in R, multiple comparisons of treatments by means of Tukey were performed using HSD.test function from the agricolae R package. Treatments with the same letter are not significantly different.

Figure 19:
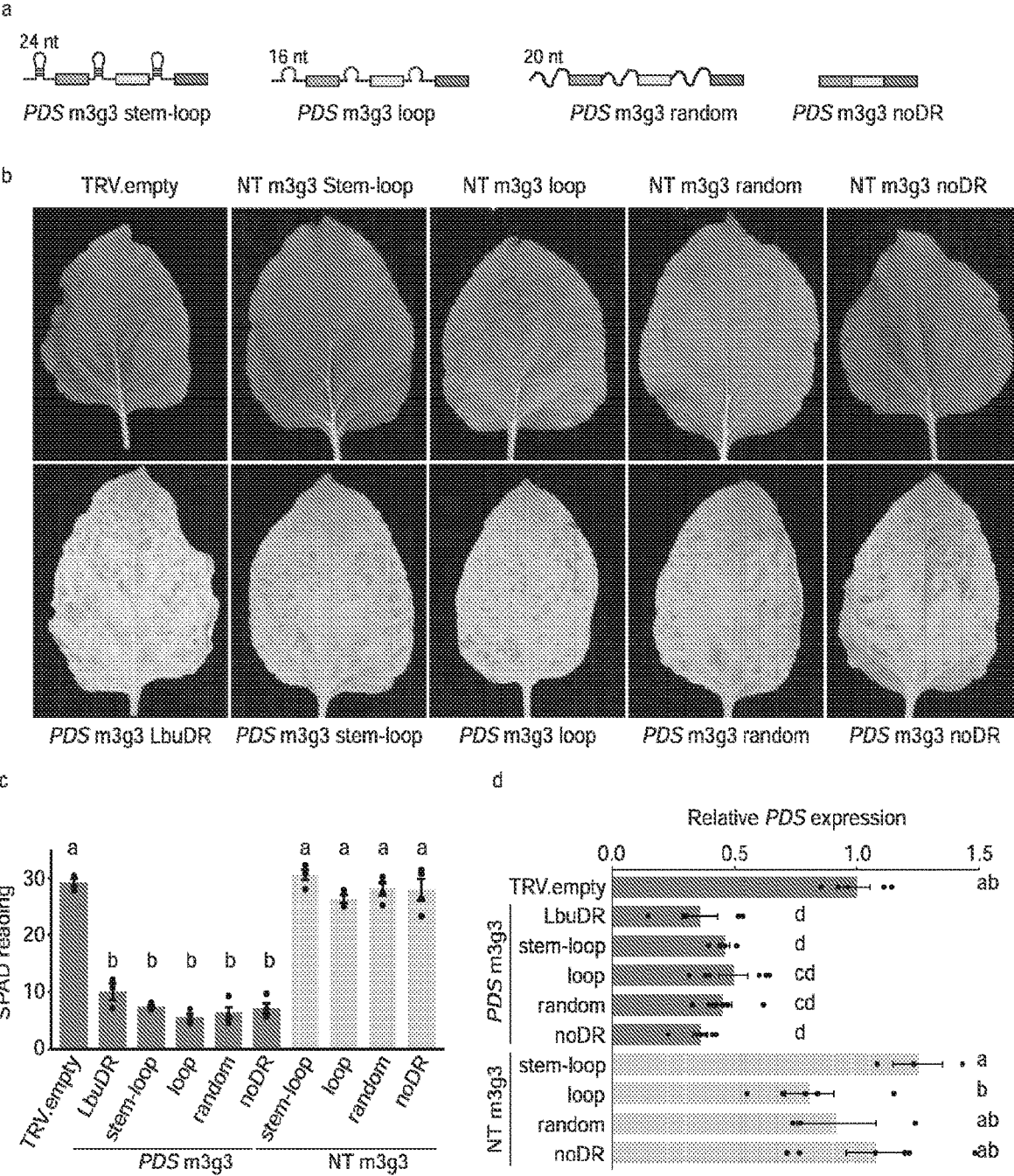

FIG. 19 shows data demonstrating that multi-guide crRNA design does not require a direct repeat. a, Schematic representation of PDS m3g3 crRNA with LbuCas13a direct repeat (LbuDR) was replaced with *Arabidopsis* miR170 stem-loop (stem-loop, 24 nt), without four-base-pair stem (loop, 16 nt), a random sequence of 20 nt (random), and without DR (noDR). b, Representative images of a lower leaf from *N. benthamiana* plants after two-weeks of TRV systemic delivery with TRV$_{empty}$, PDS m3g3 and NT m3g3 stem-loop, loop, random, and noDR crRNA constructs. c, Chlorophyll content or leaf greenness measured with SPAD meter two-weeks after systemic delivery of crRNA. d, Relative PDS expression, quantified using qRT-PCR, compared between the transformation control (TRV$_{empty}$) and each treatment. Statistical comparisons were made using one-way ANOVA in R, multiple comparisons of treatments by means of Tukey were performed using HSD.test function from the agricolae R package. Treatments with the same letter are not significantly different.

Figure 20:
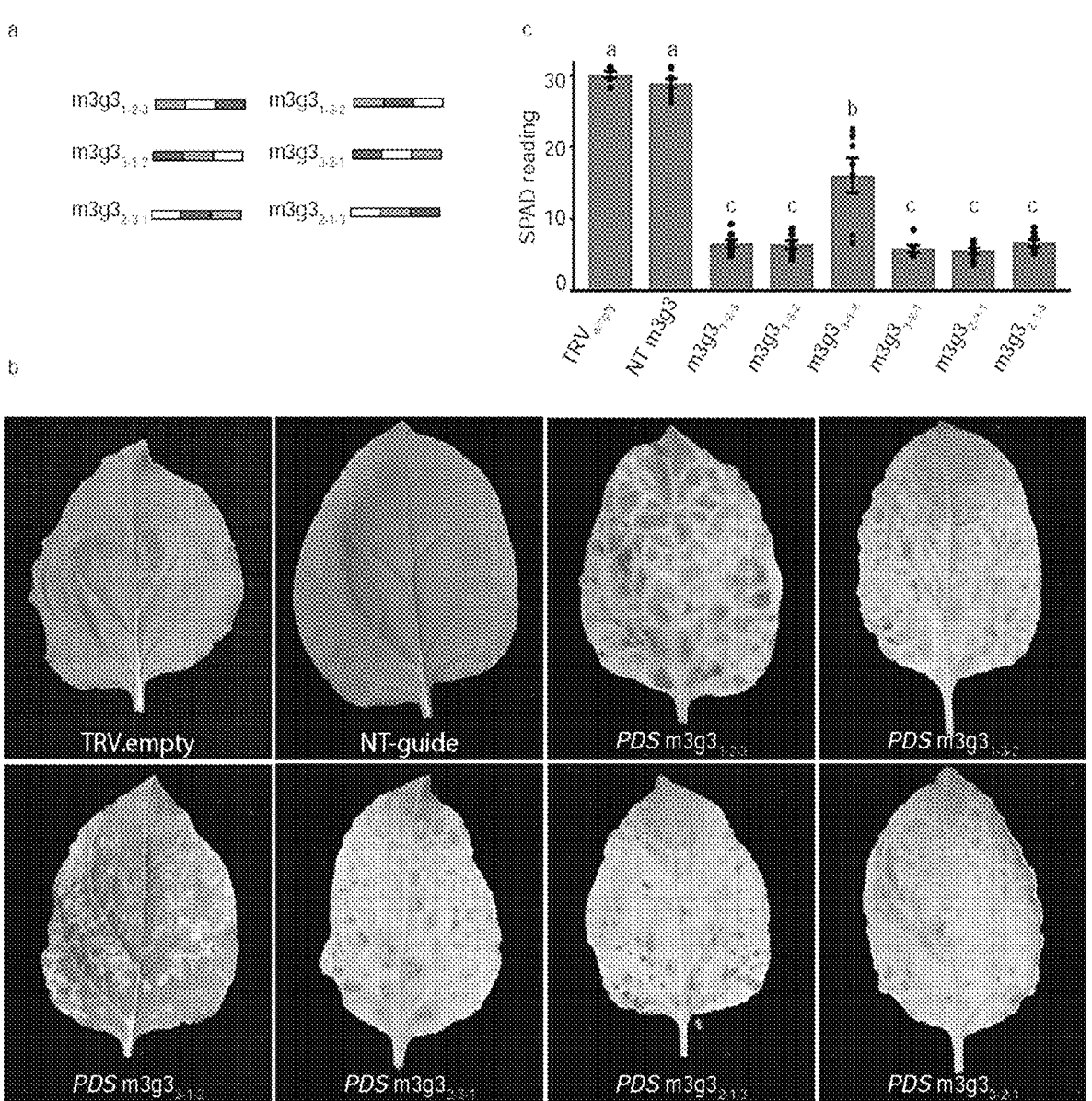

FIG. 20 shows data demonstrating that altering guide order in a PDS multi-guide did not impact visual photobleaching. a, Schematic of guide order crRNA constructs generated for determining the effect of guide order on GIGS. b, Representative images of a lower leaf from *N. benthamiana* plants after two-weeks of TRV systemic movement of TRV$_{empty}$, NT m3g3, and PDS m3g3 constructs with rearranged guide order. c, Chlorophyll content or leaf greenness measured with SPAD meter two-weeks after systemic delivery of crRNA.

Figure 21:
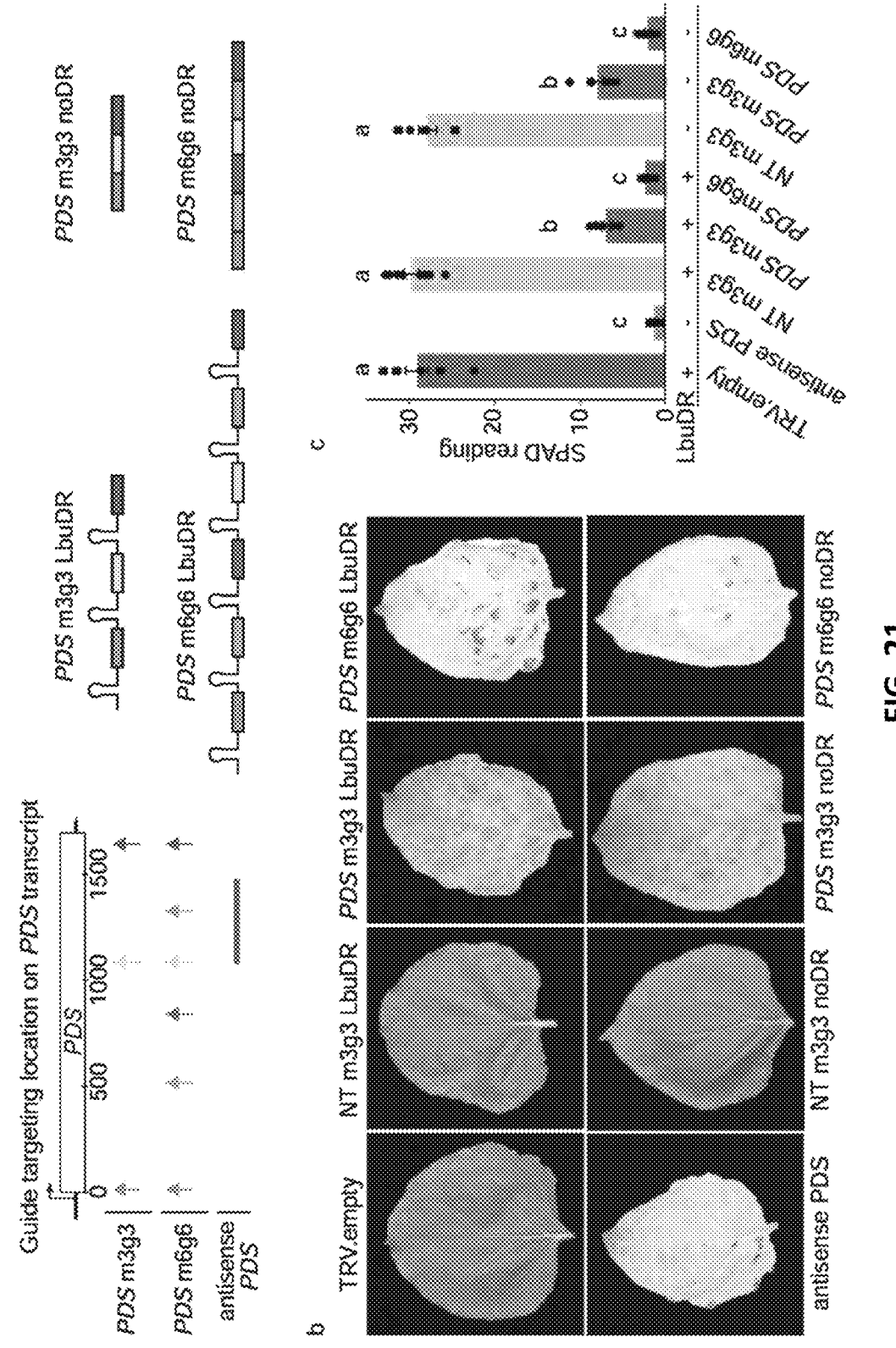

FIG. 21 shows data demonstrating that increasing PDS multi-guide crRNA number affected GIGS strength. a, Schematic of PDS m3g3 and m6g6 crRNA, and antisense PDS construct locations on PDS transcript. b, Representative images of a lower leaf from *N. benthamiana* plants after two-weeks of TRV systemic movement with m3g3 and m6g6 crRNA with or without direct repeat (LbuDR and noDR). c, Chlorophyll content measured with SPAD meter two-weeks after systemic delivery of crRNA. Statistical comparisons were made using one-way ANOVA in R, multiple comparisons of treatments by means of Tukey were performed using HSD.test function from the agricolae R package. Treatments with the same letter are not significantly different.

Figure 22:
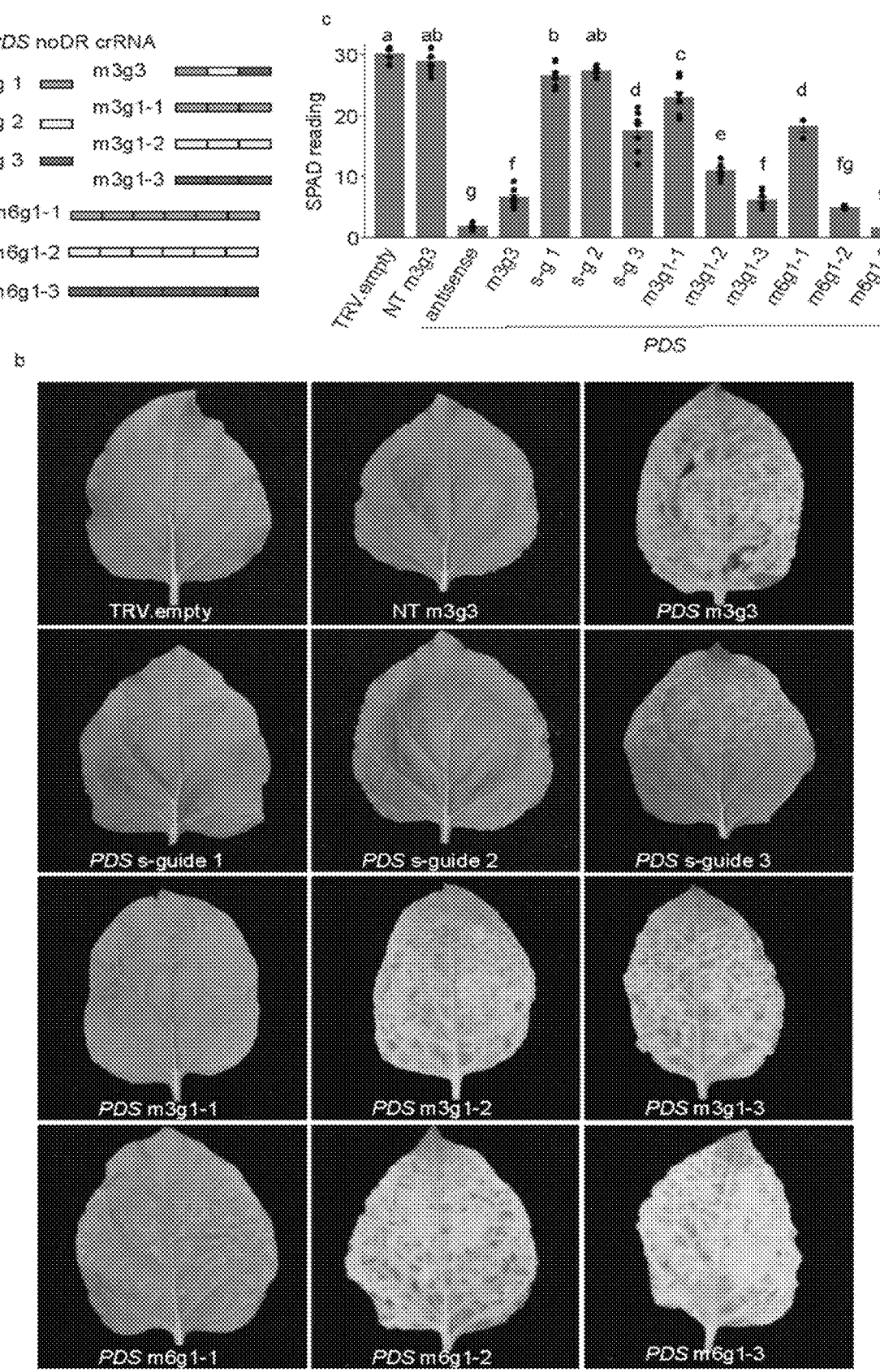

FIG. 22 shows data demonstrating that increased guide dosage elicited an increase in visible photobleaching phenotype. a, Schematic of PDS s-guides, m3g1, and m6g1 crRNA for silencing PDS expression. b, Representative images of a lower leaf from *N. benthamiana* plants after two-weeks of TRV systemic movement with three s-guides, three m3g1, and three m6g1 crRNA for targeting PDS expression. c, Chlorophyll content measured with SPAD meter two-weeks after systemic delivery of crRNA. Statistical comparisons were made using one-way ANOVA in R, multiple comparisons of treatments by means of Tukey were performed using HSD.test function from the agricolae R package. Treatments with the same letter are not significantly different.

Figure 23:

FIG. 23 shows images of plants showing systemic TRV movement of reduced guide length PDS m3g3 crRNA.

Figure 24:
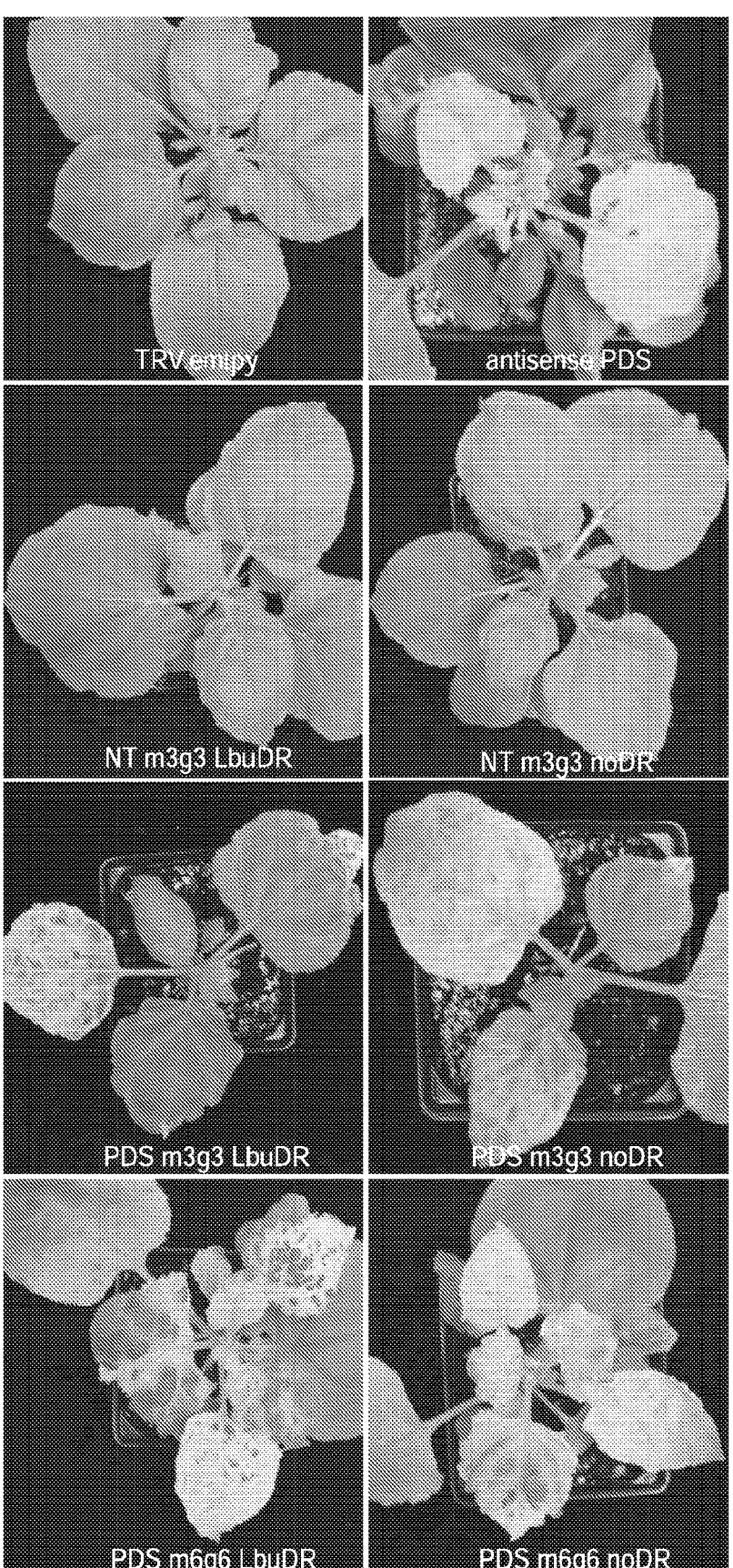

FIG. 24 shows images of plants demonstrating that increasing the number of crRNA in a PDS multi-guide elicited a strong photobleaching phenotype.

Figure 25:
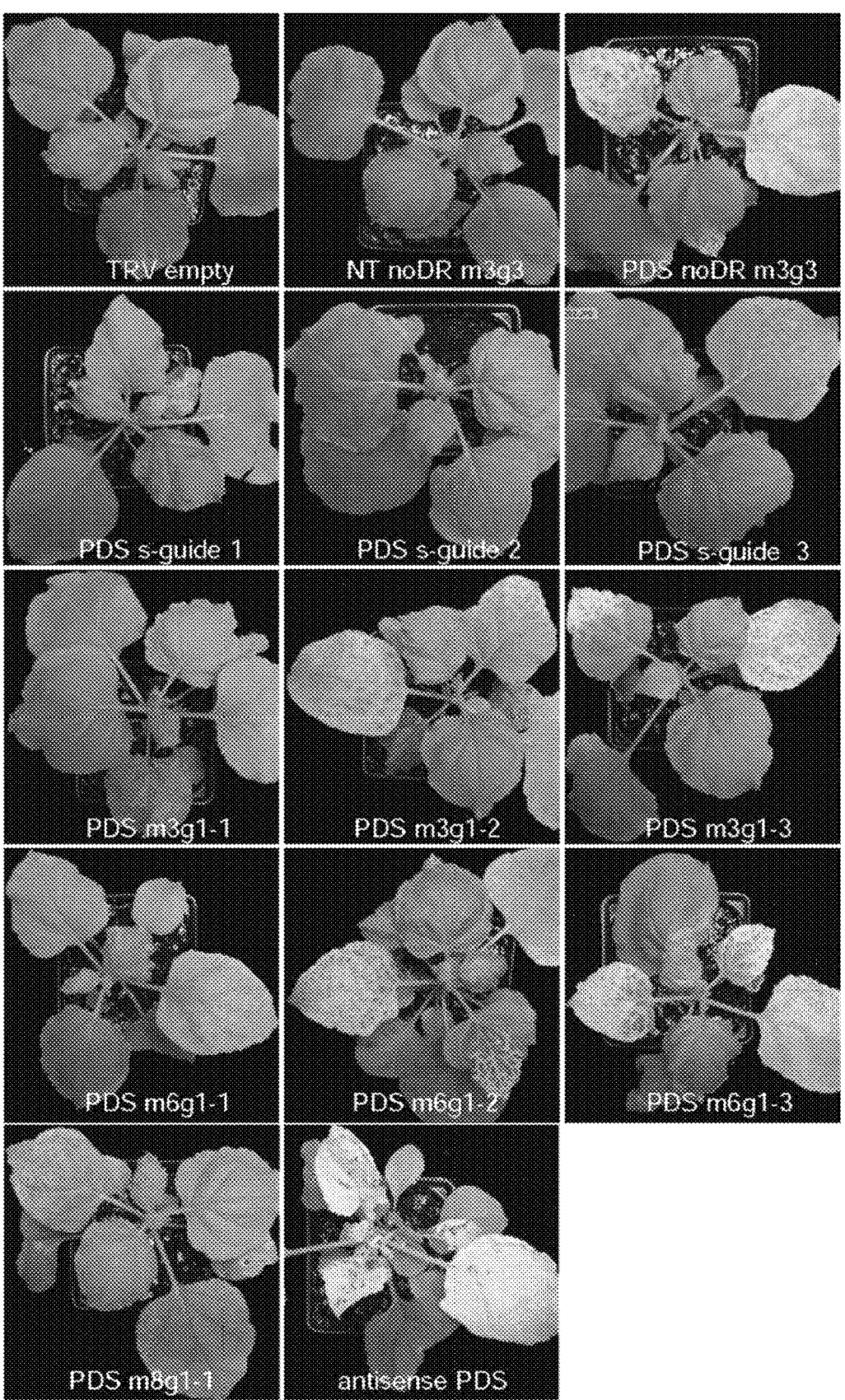

FIG. 25 shows images of plants demonstrating that the strength of GIGS elicited by increased guide dosage is RNA target dependent and that increased guide dosage resulted in stronger photobleaching.

Figure 26A:
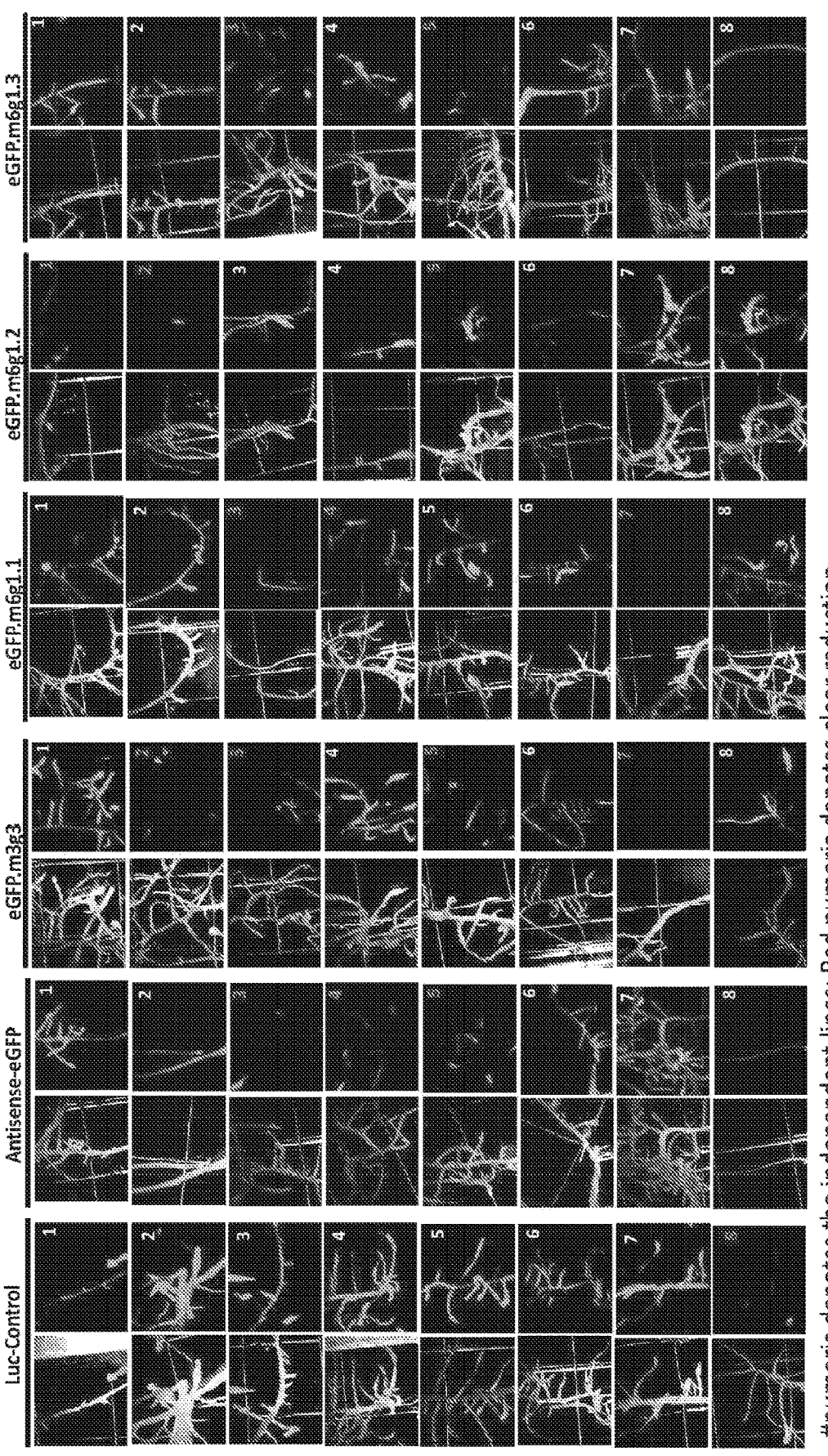

FIG. 26(A) shows images of soybean hairy roots treated with the SMRRT silencing constructs from Example 3.

Figure 26B:
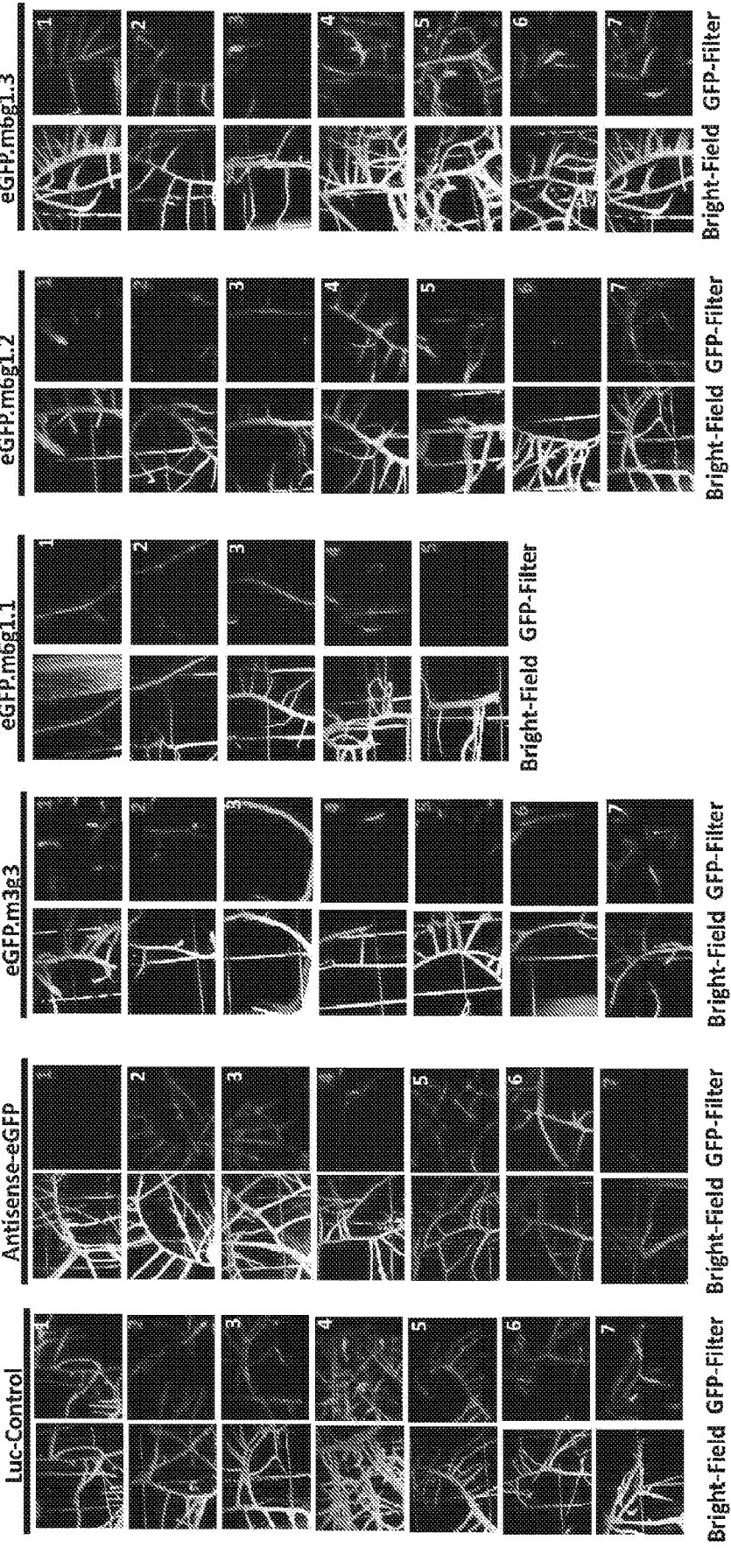

FIG. 26(B) shows images of soybean hairy roots treated with the SMRRT silencing constructs, from Example 3.

DETAILED DESCRIPTION

The present invention is concerned with new oligonucleotide constructs for manipulation of RNA targets, and their downstream products, e.g., for modification of endogenous or transgenic cellular dynamics, genotype-phenotype, and/or protein expression, as well as for targeting RNA viruses and fungi for pathogen inhibition, and engineered antiviral or antifungal activity and immunity. These new constructs are derivatives of conventional CRISPR-Cas RNA editing platforms, but function in the absence of any Cas nuclease protein. Moreover, silencing appears to be mediated by RNA endonuclease reduction and not translational inhibition of target mRNA. Further, the level of silencing can be titrated or adjusted based upon the dosage (e.g., number) of the constructs delivered to the cells, including the number of guide sequences expressed that are antisense to the target RNA. Thus, an advantage of the construct design is that it is not a binary "on" or "off" silencing approach, but rather since it targets transcript levels, the level of reduced transcripts and/or silencing of the downstream gene products can be controlled based upon the dosage of guide sequences delivered, to only partially reduce the target, and further that gradations or gradients of reduction may be achieved from significant or near complete reduction of target transcripts to minor or minimal reduction of target transcripts (and reduction levels in between, e.g., moderate reduction). Thus, the reduction of target transcript (and thus amount of silencing) is adjustable or variable along a gradient, e.g., from about 1% reduction up to near 100% reduction, and any integer between 1 and 100% reduction of the target transcript, preferably about 10%, 20%, 30%, 40%, 50%, 60%, 70%, 80%, or 90% reduction. Moreover, through the use of tissue specific promoters in the constructs, the targeting can be even more precise to selectively suppress the gene targets (not only selectively suppress the levels along a gradient, but also suppress only in certain tissues).

The constructs generally comprise short multiple repeat fragments (SMRFs) that target one or more loci of interest for silencing via targeting of complementary RNA, thus giving rise to short multi-repeat RNA targeting (SMRRT) gene silencing. The constructs comprise or encode for single-stranded, short antisense nucleotide fragments that are complementary to a target RNA sequence (e.g., in an mRNA), such that the corresponding transcripts (and their downstream products) will herein be inhibited or reduced. Thus, embodiments described herein include methods and compositions for modulating (e.g., reducing) gene, transcripts, and/or protein expression in cells. The term gene "expression" refers to any stage in the process of converting genetic information encoded in a DNA sequence or gene into RNA (e.g., mRNA, IRNA, tRNA, or snRNA) through transcription of the DNA sequence or gene (i.e., via the enzymatic action of an RNA polymerase), and into protein, through translation of mRNA. DNA sequence or gene expression can be regulated at many stages in the process.

The SMRFs are derived from CRISPR Cas guides and typically comprise, consist essentially, or consist of a CRISPR-type guide RNA (crRNA) sequence (or nucleotide sequence encoding for the crRNA sequence), which is capable of binding or hybridizing to the target RNA.

In the context of formation of a conventional CRISPR RNA-targeting complex, the target RNA sequence refers to a sequence to which a guide is designed to have sufficient complementarity, such that the guide will hybridize with the target and promote formation and binding of the CRISPR complex and interaction of the Cas nuclease with the target sequence. The target RNA sequence may be located in the nucleus or cytoplasm of a cell. The target RNA sequence may be a coding (e.g., mRNA or pre-mRNA) sequence or a non-coding (e.g., ncRNA, lncRNA, tRNA, rRNA) sequence.

Various guides are known for the different CRISPR platforms and/or can be determined manually or using a number of online tools or software programs. For example, target RNA can be selected by based on the target trait of interest such as from published experiments, unpublished experiments linking RNA expression and resulting protein function to a trait of interest, sequences present in a viral or fungal pathogen of interest, or other endogenously transcribed RNA in an organism the user wishes to target, taking into account the conserved nature of the target as well as any structural considerations for secondary structures of the target transcripts. From this information, guide sequences can be designed (and then synthetized) as respective antisense sequences to the target RNA, specifically with complementarity to one or more positions, locations, or regions along the target RNA sequence, which can be contiguous target sequences or non-contiguous target regions in the target RNA. The SMRFs can target any region from the 5' start to the 3' end of the target RNA, including sequences that do or do not contain protein translation sequences. Target regions can be further refined by modeling target RNA secondary structure, which could be based on commercially available software and online tools such as, but not limited to, RNAfold (rna.tbi.univie.ac.at//cgi-bin/RNAWebSuite/RNAfold.cgi). Regions with less secondary structure interpreted through less self-pairing and higher disorder or entropy are considered as better regions for targeting with guides. Target regions can be further refined by modeling RNA-RNA interactions, which could be based on commercially available software and online tools such as, but not limited to, RNAup (rna.tbi.univie.ac.at//cgi-bin/RNAWebSuite/RNAfold.cgi). Here, potential or candidate antisense sequences are checked against the target sequence to model the energy of guide-target pairing and energy to open the target sequence. Better guides have a more negative free energy of binding, that is they are energetically more favorable, and require a lower opening energy for the target sequence. Preferably, off target effects are reduced in the system, such that the desired degree of complementarity between a guide sequence and its corresponding target sequence is greater than 95%, more preferably greater than 98%, more preferably greater than 99%, and even about 100% (+/−0.5%).

In the present disclosure, the construct is free of CRISPR-associated (Cas) nucleases or proteins (or nucleic acids encoding such nucleases or proteins), and any other sequence derived from the CRISPR-Cas system. Thus, while the conventional nomenclature of "guide" or crRNA sequence is used herein, it will be appreciated that the targeting constructs used herein no longer "guide" a CRISPR enzyme to the target, and no longer contain characteristic bacterial or archaea derived sequences. Nevertheless, the technology can leverage the existing libraries of CRISPR RNA guides which have been identified for various systems and conditions, and can be used in the constructs described herein to target the desired RNA.

This technology is currently demonstrated in four different plant systems using numerous multi-guide constructs, but can be applied in various eukaryotic systems including animals, insects, fungi, and plants, as well as for inhibition of RNA viruses. In one or more embodiments, each guide segment or fragment consists of a sequence length of 15 nucleotides (nt) up to 100 nt, preferably from 20 nt to 80 nt, and preferably from 20 nt to 50 nt, more preferably from 22 nt to 30 nt. Notably, the guide construct does not need to target a contiguous piece of target RNA.

Figure 1:
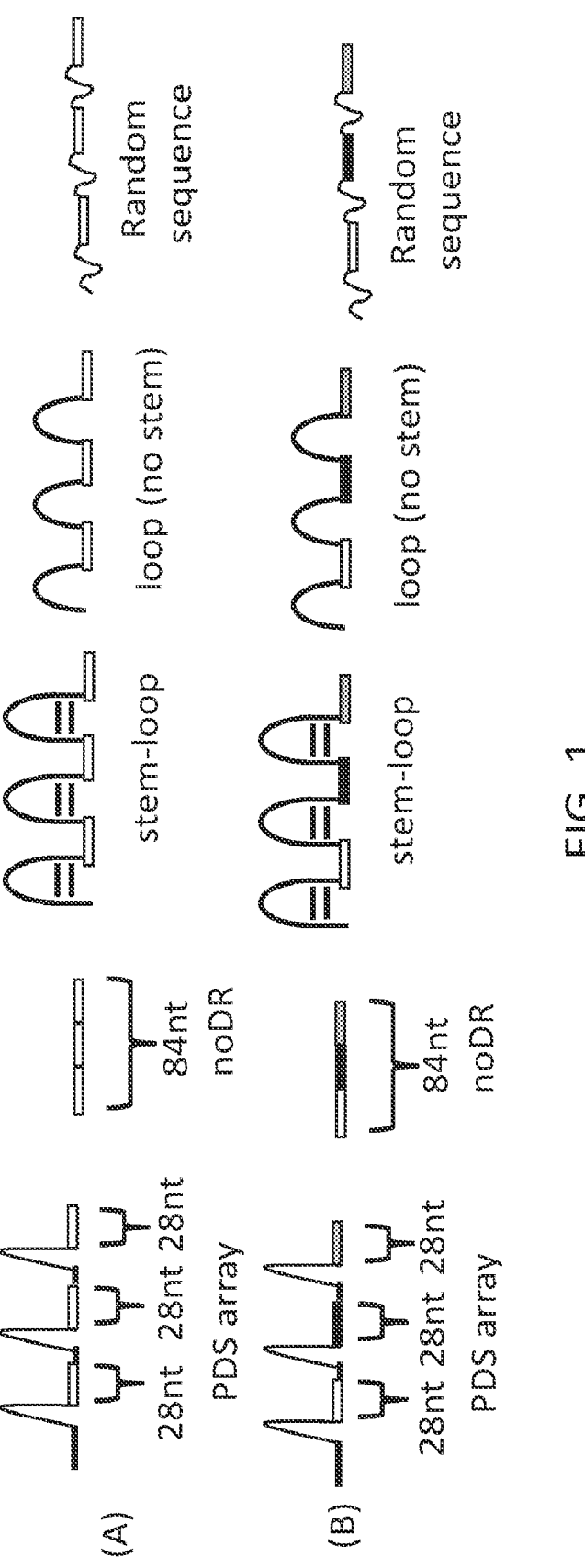
FIG. 1 is a cartoon illustration of various SMRRT silencing constructs in accordance with embodiments of the invention, showing (A) homogenous multimers; and (B) heterogenous multimers.

The architecture of the SMRFs for SMRRT silencing can be arranged in numerous ways as illustrated in FIGS. 1(A) and 1(B), subject to certain design constraints, namely that the constructs comprise two or more guide fragments targeting one or more RNA targets (i.e., short anti-sense fragments complementary to a region of one or more RNA targets). As illustrated in FIG. 1(A), in one or more embodiments, the SMRF construct can comprise a homogeneous multimer comprising two or more copies of the same guide sequence on the same construct (expression cassette). In such homogenous multimers, the two or more guide sequences can be directly linked (e.g., immediately adjacent on the cassette without any intervening sequences or nt). In such homogenous multimers, the two or more guide sequences can be indirectly linked, such that each guide fragment is separated by an intervening sequence. In the homogenous multimer, the individual guide fragment repeats, each have complementarity with the same region of the same RNA target. In the homogenous multimer, the individual guide fragment repeats could also have complementarity with similar (homologous) regions of different RNA targets. In one or more embodiments, as illustrated in FIG. 1(B), the SMRF construct can comprise a heterogenous multimer comprising two or more different guide sequences on the same construct (expression cassette). In such heterogenous multimers, the two or more different guide sequences can be directly linked (e.g., without any intervening sequences or nts). In such heterogenous multimers, the two or more different guide sequences can be indirectly linked, such that each guide fragment is separated by an intervening sequence. In the heterogenous multimer, the different guide fragments can each target the same RNA target, but have complementarity with a different region of the target. In one or more embodiments, the different guide fragments target loci that are spaced apart from one another on the target RNA (e.g., opposite ends, or beginning and middle, or middle and end of the target region, etc.). In one or more embodiments, the different guide fragments target contiguous loci on the target RNA (e.g., different sequentially located sequence segments). In the heterogenous multimer, the different guide fragments can each target a different RNA target entirely (e.g., a first guide fragment with complementarity to a first RNA target and a second guide fragment with complementarity to a second RNA target that is a different RNA molecule from the first RNA target).

The intervening sequences, if present, in the homogenous or heterogenous multimers can comprise (consist essentially or even consist of) direct repeat sequences (typically included with CRISPR guides), as well as random short intervening sequences (e.g., less than 30 nts). The direct repeat sequences can comprise a stem loop or other secondary structures (e.g., loop only, lacking the stem). In one or more embodiments, the intervening sequences, if present, are each located upstream (i.e., 5') from each respective guide fragment. In one or more embodiments, the intervening sequences, if present, are each located downstream (i.e., 3') from each respective guide fragment. With the exception of small loops or stem loops, the guide fragments are not designed to form any other secondary structures and are free of hairpin loops-they are not self-complementary and do not form double-stranded structures with themselves. Each fragment in the multimer can be driven by the same single promoter 5' to the entire expression cassette or respective promoters 5' to each fragment. Thus, intervening sequences in the multimers can include promoters or other regulatory sequences between the sequences.

In one or more embodiments, the present disclosure contemplates expression cassettes comprising 2 or more guide fragments directly or indirectly connected. In one or more embodiments, the present disclosure contemplates expression cassettes comprising 3 or more guide fragments directly or indirectly connected. In one or more embodiments, the present disclosure contemplates expression cassettes comprising 4 or more guide fragments directly or indirectly connected. In one or more embodiments, the present disclosure contemplates expression cassettes comprising 5 or more guide fragments directly or indirectly connected. In one or more embodiments, the present disclosure contemplates expression cassettes comprising 6 or more guide fragments directly or indirectly connected. In one or more embodiments, the present disclosure contemplates expression cassettes comprising 7 or more guide fragments directly or indirectly connected. In one or more embodiments, the present disclosure contemplates expression cassettes comprising 8 or more guide fragments directly or indirectly connected. In such embodiments, the multiple guide fragments are expressed as a single transcript (same sequence on a single transcript) for SMRRT silencing.

In one or more embodiments, compositions are contemplated herein which comprise multiple guide fragments, each expressed as multiple independent transcripts of their respective expression cassettes for SMRRT silencing (see FIG. 17a). Such single-guide constructs may comprise respective promoter sequences, as well as direct repeats, stem loops or other secondary structures. These single-guide constructs are co-expressed in the system.

Thus, embodiments described herein contemplate inhibition or reduced expression of target RNA transcripts and/or proteins via delivery the SMRFs, which may be located on the same vector or co-expressed on different vectors of the system. In one or more embodiments, the guide fragments are designed and combined in the expression cassette(s) so as to target multiple regions of a target RNA. In one or more embodiments, the guide fragments are designed and combined in the expression cassette(s) so as to target multiple RNA targets. The SMRF constructs can comprise DNA that encodes for the guide fragments (and is transcribed in vitro or in vivo into the corresponding RNA). The SMRF constructs can comprise transcribed crRNA. The SMRF constructs can comprise chemically synthesized RNA. The SMRF constructs can be further modified to improve stability (e.g., with 5' or 3' capping), addition of a detectable label (e.g., fluorescent moiety) and the like. For ease of reference herein, the terms crRNA or guide fragments are used interchangeably and may be referred to as "RNA guides" inclusive of either the RNA molecule itself or a DNA molecule which encodes for the RNA guide fragment. Thus, although the DNA sequence may be depicted, it is conventional in the art to still refer to this construct as an "RNA" guide or "crRNA guide."

Embodiments described herein encompasses methods for delivering multiple guide fragments, wherein each guide fragment is specific for a different target locus of interest thereby modifying multiple target loci of interest. Alternatively, multiple repeats of the same fragment can be delivered, which appears to provide the best balance of robust silencing with fewer off-target effects. As demonstrated in the data, a stronger reduction in target mRNA can be observed using multi-guide cassettes. The approaches described herein can be applied to improve emerging as well as existing CRISPR-based gene editing systems, and SMRRT silencing approach can be used with new CRISPR-Cas guides as they are developed or identified.

In one or more embodiments, described herein are methods of modifying a target locus of interest, in particular in eukaryotic or prokaryotic cells, tissues, organs, or organisms, in particular in animal, plant, bacterial, or fungal cells, tissues, organs, or organisms. In one or more embodiments, described herein are methods of reducing the expression of one or more transcripts of a target locus in an organism. In one or more embodiments, described herein are methods of reducing the expression of one or more genes "associated with" the RNA target (e.g., genes encoding for the RNA target that is ultimately translated into the gene product, typically having a detectable phenotype). In other words, the target RNA transcripts are associated with the target gene whose expression is desired to be altered. Degradation of the target RNA transcripts prevent translation of the gene product, which can be detected as reduced protein expression and/or altered phenotype.

In one or more embodiments, the SMRF constructs can be used in methods for partially or completely silencing trans or endogenous genes in plants. As such, this technology offers a potential solution to bypass antagonistic pleiotropy by silencing targeted genes in a tissue-, age-, or inducible-specific manner. The construct or vector can be introduced by any suitable method, including, without limitation, agroinfiltration, biolistic particle delivery system, microprojectile bombardment, viral infection, *Agrobacterium*-mediated transformation (*Agrobacterium tumefaciens*), PEG- or electroporation-mediated uptake, particle bombardment-mediated delivery, microinjection, nanoparticle delivery, or liposomal delivery, to produce modified plant cells, tissues, or plants. The term "bombardment" with respect to transformation refers to the process of accelerating particles towards a target biological sample (e.g., cell, tissue, seedling, etc.) to effect wounding of the cell membrane of a cell in the target biological sample and/or entry of the particles into the target biological sample. In some embodiments, the constructs can be formulated in delivery vehicles that facilitate uptake of the constructs through the root system, leaves, or other tissues of the plants. The constructs may be applied to the leaves or other tissue of the plants. The constructs may be applied to the roots or in the vicinity of the roots (e.g., to the growth medium, soil, sand, dirt, etc.) in which the plant is rooted. The constructs can also be delivered to the meristematic tissue of developing or developed plants.

In any case, introduction of the constructs results in altered levels of expression of the target in the plant. References to altered "levels" of expression refers to the production of gene product(s) in modified plants in amounts or proportions that differ from that of normal, control, or non-modified plants. The modifications can result in plants having favorable or improved morphological or phenotypical characteristics, such as: vigorous growth, abundant foliage, longer primary roots, yield, height, and/or shoot water potential, pest resistance, drought tolerance, heat tolerance, salt tolerance, cold resistance, herbicide resistance, fungal resistance or reduced fungal susceptibility (e.g., by targeting RNA transcripts of a susceptibility gene), viral resistance, or reduced viral susceptibility (e.g., by targeting RNA transcripts of a susceptibility gene), water-use efficiency, nutrient uptake, or altered chemical profiles such as in the leaf, shoot, stem, seed, flower, tuber, hypocotyl, root, or lateral root. Altered chemical profiles could include changes in the relative amount of a chemical, or could include changes in the structure of the chemical, or could include changes in the spatial partitioning of the chemical compared to a normal, or control, or non-modified plants. Alternatively, the constructs can be used as herbicides to result in plants having impaired morphological or phenotypical characteristics, such as heat, drought, salt susceptibility, shortened root systems, photo-sensitivity, and the like. The constructs can be used to target critical pathways, such as photosynthesis, or derived photosynthetic carbon utilization or movement, to cause death of unwanted plants, or to render the plant susceptible to herbicides.

The methods can be used for monocotyledonous as well as dicotyledonous plants. Examples of suitable plants include, without limitation, wheat (*Triticum* sp.), barley (*Hordeum* sp.), rice (*Oryza* sp.), maize (*Zea* sp.), rye (*Secale* sp.), corn (maize), cassava, sorghum (*Sorghum bicolor*), and cereal crops (grasses in monocot family Poaceae including annual and perennial grasses), as well as soybeans (*Glycine* sp.), tomato (*Solanum* sp.), cotton (*Gossypium* sp.), tobacco (*Nicotiana tabacum*), potato (*Solanum tuberosum*), strawberry (*Fragaria* spp.), olive trees, grape vines, other embodiments of fruit and nut trees, poplar trees, as well as research plants such as *Arabidopsis, Brachapodium* spp., *Nicotiana benthamiana*, as well as photosynthetic algae. The methods can also be used for weeds or other invasive plant species, such as common waterhemp, palmer amaranth, giant/common ragweed, common lambsquarters, velvetleaf, giant foxtail, woolly cupgrass, burcucumber, morning glory, horseweed, marestail, sunflower, bluegrass, canada thistle, foxtail spp., johnsongrass, cheat grass, crabgrass, nutsedge, purple deadnettle, kochia, nightshade, pigweed, and kudzu vine.

The methods can be used to establish stable trans- or cis-genic plants expressing guide RNA constructs against an RNA target. In one or more embodiments, the SMRRT silencing constructs are inheritable, giving rise to inheritable phenotypes in progeny. Thus, embodiments herein contemplate seeds, seedlings, and progeny of modified plants, wherein the SMRRT silencing constructs are expressed in the seeds, seedlings, or progeny. Further, embodiments herein contemplate progeny with multiple traits targeted for modification, for example by using traditional breeding techniques to cross two or more plants that have been modified using the SMRRT silencing constructs, thus yielding seeds, seedlings, or progeny, expressing both of the inherited guide RNA constructs. It will be appreciated that these stably incorporated constructs can thus be used to achieve any combination of modified characteristics or traits in plants.

In one or more embodiments, the SMRF constructs can be used in methods for partially or completely silencing endogenous genes in fungi or reducing target RNA levels, such as components of cell wall synthesis including but not limited to glucan synthases, synthesis of membrane components such as ergosterol, components of primary metabolism or other components of primary growth.

In one or more embodiments, the SMRF constructs can be used in methods for partially or completely silencing endogenous genes in bacteria or reducing target RNA levels, such as by targeting bacterial small RNA or other RNA transcripts in critical pathways for bacterial growth and/or metabolism. Thus, the SMRF constructs may be used as antibacterial compounds, and can be used to inhibit bacterial growth and/or infection.

In one or more embodiments, the SMRF constructs can be used in methods for partially or completely silencing endogenous genes in an animal, such as insects, reptiles, amphibians, fish (e.g., zebrafish), poultry, and mammals, such as rodents (e.g., mouse, rat, rabbit), dogs, cats, pigs, horses, cows, goats, sheep, monkeys, primates, and humans. The SMRF constructs can be formulated for administration using pharmaceutically-acceptable vehicles or excipients. Nucleic acid constructs are particularly suited for delivery via various nanoparticles, liposomes, viral vectors, or vesicles as the delivery vehicles for encapsulating the constructs. In general, a plurality of the SMRF constructs are dispersed in a pharmaceutically-acceptable carrier. The term carrier is used herein to refer to diluents, excipients, vehicles, and the like, in which the constructs may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would be selected to minimize any degradation of the constructs or other agents and to minimize any adverse side effects in the subject. Pharmaceutically-acceptable ingredients include those acceptable for veterinary use as well as human pharmaceutical use and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), various oil-in-water or water-in-oil emulsions, as well as dimethyl sulfoxide (DMSO), other acceptable vehicles, and the like.

The composition can comprise a therapeutically effective amount of the SMRRT silencing constructs dispersed in the carrier. As used herein, a "therapeutically effective" amount refers to the amount that will elicit the biological or medical response of a tissue, system, or subject that is being sought by a researcher or clinician, and in particular elicit some desired therapeutic effect as against the condition such as by reducing the target RNA transcripts. One of skill in the art recognizes that an amount may be considered therapeutically "effective" even if the condition is not totally eradicated or prevented, but it or its symptoms and/or effects are improved or alleviated partially in the subject. In some embodiments, the composition will comprise from about 5% to about 95% by weight of the SMRRT silencing constructs described herein, and preferably from about 30% to about 90% by weight of the SMRRT silencing constructs, based upon the total weight of the composition taken as 100% by weight. Encapsulation techniques can also be used to facilitate delivery of the SMRRT silencing constructs. Other ingredients may be included in the composition, such as adjuvants, other active agents, preservatives, buffering agents, salts, other pharmaceutically-acceptable ingredients.

In use, a therapeutically-effective amount of the SMRRT silencing constructs is administered to a subject. In some embodiments, a composition comprising a therapeutically-effective amount of constructs are administered to a subject. The disclosed embodiments are suitable for various routes of administration, depending upon the particular carrier and other ingredients used. For example, the SMRRT silencing constructs can be injected intramuscularly, intraperitoneally, subcutaneously, intradermally, or intravenously. They can also be administered via mucosa such as intranasally or orally. The compounds or compositions can also be administered through the skin via a transdermal patch, or topically applied to dermal and epidermal-based cancers or viral infections. A researcher, clinician, or medical practitioner can determine the appropriate dosage amount and timing regimen depending upon various factors such as the age, weight, and overall health of the subject, as well as the severity and stage of the condition to be treated. The SMRRT silencing constructs can be administered, daily, ever other day, weekly, monthly, and the like.

In some embodiments, the SMRRT silencing constructs (or compositions) can be provided in unit dosage form in a suitable container. The term "unit dosage form" refers to a physically discrete unit suitable as a unitary dosage for human or animal use. Each unit dosage form may contain a predetermined amount of the SMRRT silencing constructs (and/or other active agents) in the carrier calculated to produce a desired effect. A kit comprising the SMRRT silencing constructs is also disclosed herein. The kit further comprises instructions for administering the SMRRT silencing constructs to a subject. The SMRRT silencing constructs can be provided as part of a dosage unit, already dispersed in a pharmaceutically-acceptable carrier, or provided separately from the carrier. The kit can further comprise instructions for preparing the SMRRT silencing constructs for administration to a subject, including for example, instructions for dispersing the SMRRT silencing constructs in a suitable carrier.

It will be appreciated that therapeutic and prophylactic methods described herein are applicable to humans as well as for veterinary use for any suitable animal, including, without limitation, dogs, cats, and other companion animals, as well as, rodents, primates, horses, cattle, pigs, etc. The methods can be also applied for clinical research and/or study.

The method comprises delivering to the target locus a SMRRT silencing construct according to the various embodiments herein, wherein binding between the complementary guide fragments from the SMRRT silencing construct and the target locus induces the modification of the target locus of interest. In particular, binding of the guide crRNA fragment with its complementary target yields double-stranded RNA which triggers the endogenous RNA processing machinery of the host cell or organisms. This leads to degradation of the RNA target and thus reduction in downstream gene products.

The RNA-targeting constructs can also be used for inhibition of RNA viruses. For example, the SMRRT silencing constructs can also be used to inhibit RNA viral replication and infection in plants. It is readily appreciated that the antisense silencing RNAs are capable of hybridizing directly to the genomic RNA ((+) RNA strand) of the target virus by base pairing, and so of inhibiting the genomic RNA either prior to or during replication, whereas the sense silencing RNAs are capable of hybridizing to the (−) replicative strand of the target virus which is produced during replication of the target virus, and thereby are capable of inhibiting replication of RNA viruses during viral replication, or subgenomic RNAs, thereby capable of degrading viral messenger RNA, i.e., post-transcriptional degradation. The constructs can be introduced into plant cells or tissues to inhibit viral replication in the plants.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein "regulatory sequences" refers to promoters, enhancers, and other expression control signals that direct constitutive expression of a nucleotide sequence. Such elements may be host-specific or may drive expression broadly across various host cell types. Such elements may also be inducible and direct expression only under certain conditions (e.g., active or "on" only under an external stimulus, tissue-specific, or developmentally determined parameter). Advantageously, regulatory sequences can be selected to achieve targeted expression of the constructs. That is, a native promoter can be identified for the host organism that has a specific expression pattern (e.g., time or tissue specific expression). Using this promoter in the constructs ensures that the construct is thus, only expressed in the desired tissue or at the desired time. That way, you only get target mRNA silencing in that tissue (e.g., only in the roots, or root hairs, or only in the root epidermis in the elongation zone, etc.) or at the particular time of development. In this way, the constructs can be selectively activated.

A "host cell" or "target cell" as used herein, refers to the cell into which the constructs have been introduced, include the progeny of the original modified cell. A "host" or "subject" as used herein refers to an individual organism targeted for altered gene expression via SMRF manipulation of RNA targets. Likewise, a "host" or "target" population refers to a plurality of individual host organisms which may be targeted for altered gene expression through SMRF manipulation of RNA targets.

The term "control" when used with respect to control plants or other organisms includes wild-type (native) plants or organisms, as well as cultivars and genetically altered plants that otherwise contain a wild-type, non-modified, or native (endogenous) gene targeted for silencing (inhibition) according to the invention. Such control plants or organisms are compared to "modified" plants or organisms which have been treated with the SMRF constructs according to the invention.

The "inhibition," "silencing," or "knock down" of the expression, activity, or function of a gene, as used herein, is intended to refer to any suitable method of reducing or even completely suppressing protein expression from a gene or a coding sequence, including methods of reducing the levels of protein produced as a result of gene transcription to mRNA and subsequent translation of the mRNA. Gene inhibition may be effective against a native gene associated with a trait, e.g., to provide the organism with a diminished level of a protein encoded by the native gene or with reduced levels of an affected metabolite.

The terms "vector" or "expression cassette" refer to nucleic acid molecules that transfer DNA or RNA segment(s) from one cell to another. The term includes recombinant DNA or RNA molecules containing a desired coding sequence(s) and appropriate nucleic acid sequences (e.g., promoters) necessary for the expression of the operably linked coding sequence in a particular host organism. In one or more embodiments, the vector is a plasmid. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell.

A "sense" strand of nucleic acid construct refers to a strand that is transcribed by a cell in its natural state into a "sense" mRNA. The term "antisense" refers to a DNA sequence whose sequence of deoxyribonucleotide residues is complementary to all or part of the sequence of deoxyribonucleotide residues in a sense strand. Thus, an "antisense" sequence is a sequence having the same sequence as the non-coding strand in a DNA duplex. With respect to RNA, the term "antisense" refers to an RNA transcript that is complementary to all or part of a target primary transcript or mRNA and that blocks the expression of a target gene by interfering with the processing, transport and/or translation of its primary transcript or mRNA. The complementarity of an antisense RNA or DNA may be with any part of the specific gene or transcript, i.e., at the 5' non-coding sequence, 3' non-coding sequence, introns, or the coding sequence.

The present description uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

Finally, as used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

EXAMPLES

The following examples set forth methods in accordance with the invention. It is to be understood, however, that these examples are provided by way of illustration and nothing therein should be taken as a limitation upon the overall scope of the invention.

Introduction

The development of RNA-targeting CRISPR provides potential advantages over DNA editing, such as avoiding pleiotropic effects of genome editing and expanded function including anti-viral immunity. Here, we report the use of CRISPR-Cas13 in plants to reduce both viral and endogenous RNA. Unexpectedly, we discovered that crRNA designed to guide Cas13 could, in the absence of the Cas13 protein, cause substantial reduction in RNA levels as well. We demonstrate this Cas13-independent silencing in four plant species, including stable transgenic *Arabidopsis*. We determined this was the result of crRNA dependent guide-induced gene silencing (GIGS) and show that GIGS utilizes endogenous RNAi machinery. From this work, we have further explored guide design and re-termed these constructs as "short multiple repeat fragments" (SMRFs) for use in short multi-repeat RNA targeting (SMRRT), since the designed RNA constructs are no longer "guiding" anything to the target. Our results demonstrate that SMRRT silencing is active across a range of plant species and provides a novel and flexible approach to RNA reduction. These findings, along with similar evidence in mosquitoes, suggests that GIGS is potentially active across many eukaryotes.

Example 1

An alternative approach to targeting DNA is the manipulation of RNA. RNA plays a central role in cellular dynamics, mediating phenotype and trait development across eukaryotes. Manipulating RNA does not require editing the DNA of multi-copy sequences, and could be developed to overcome negative pleiotropy. As such, we initially sought to develop the class II type VI CRISPR-Cas13 system, where the Cas13 nuclease specifically binds target single-stranded (ss)RNA in a CRISPR RNA (crRNA) guided manner, to function as an introduced anti-viral immune system and more generally as a platform to manipulate endogenous plant mRNA. Cas13a (formerly C2c2), first characterized by Abudayyeh et al. (2016), Cas13d, first characterized by Konermann et. al. (2018).

Programmable CRISPR-Cas13 machinery requires a CRISPR-Cas13 protein, and CRISPR-RNA (crRNA) containing a 37 nucleotide (nt) direct repeat (DR), followed by a 28 nt spacer/guide to direct the Cas13 protein towards a specific mRNA sequence.

Figure 5:
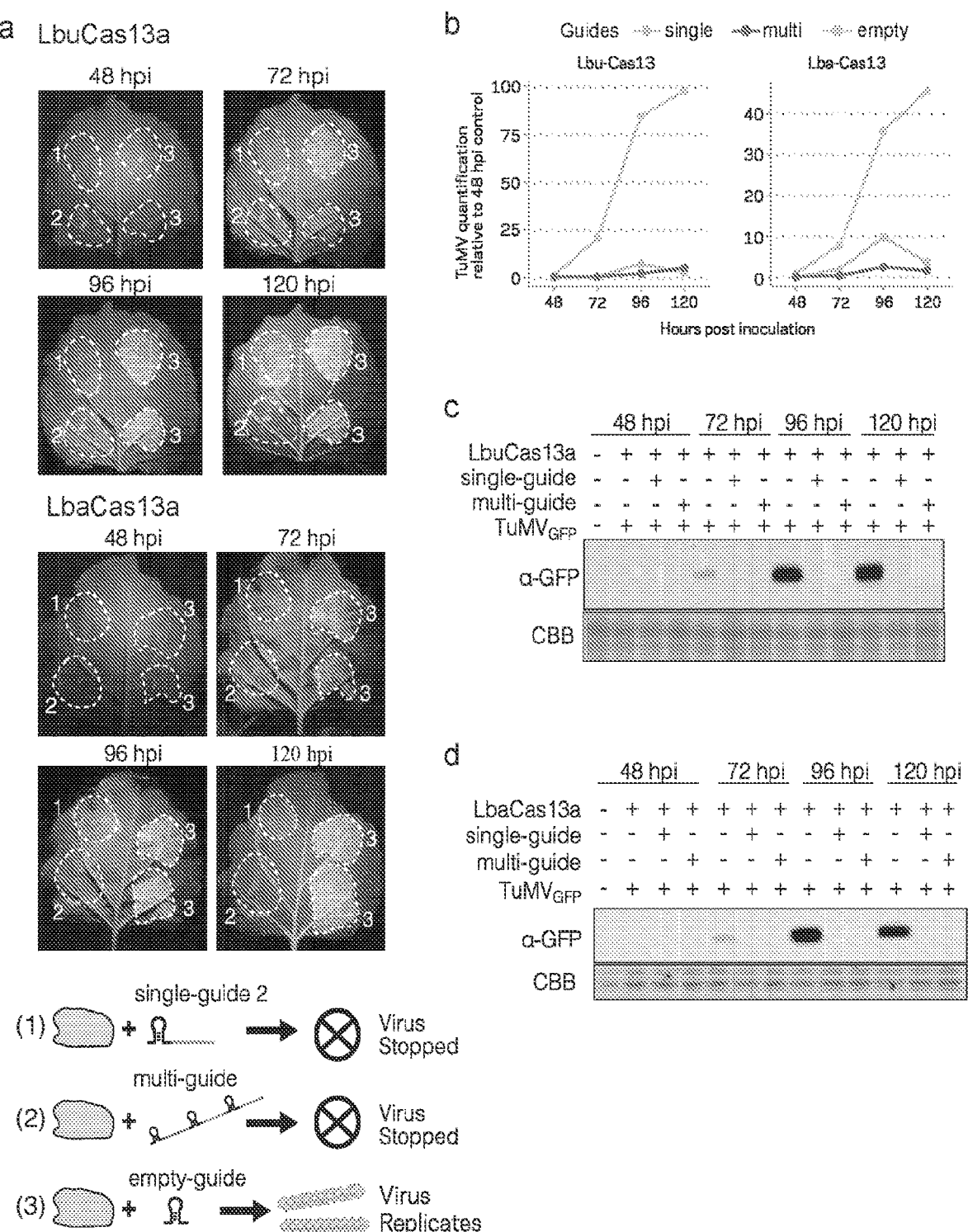
FIG. 5 shows data demonstrating that Cas13a mediated efficient virus interference. (a) Images of *N. benthamiana* leaves from 48 hours post inoculation (hpi) to 120 hpi shown under UV light to visualize GFP fluorescence. The Cas13 protein (either LbuCas13 or LbaCas13) were expressed with a guide and the TuMV expressing GFP virus as indicated by the schematic diagram and numbering. The areas of agroinfiltration are indicated with white dashed circles. Higher GFP signal results from increased virus accumulation (b) Quantification of viral genome accumulation using qPCR. TuMV levels were standardized to a plant endogenous transcript and three samples were collected per time point. c,d, GFP protein accumulation over the time series of inoculated leaves expressing LbuCas13a (c) or LbaCas13a (d). The lanes are labeled above the images for each time point, while the anti-GFP ($\alpha$-GFP) panel shows signal from western blot, and the commassie brilliant blue (CBB) stained gel panel shows the loading control.

Two Cas13a proteins (from *Lachnospiraceae bacterium* (LbaCas13a) or *Leptotrichia buccalis* (LbuCas13a)) were co-expressed with Turnip mosaic virus (TuMV) expressing GFP in *Nicotiana benthamiana* leaves using *Agrobacterium*-mediated transient expression. The Cas13 proteins were expressed either with a single-guide crRNA containing antisense sequence to one region of the TuMV genome (single-guide), a multi-guide crRNA containing sequences against three regions of the genome (multi-guide), or an empty-guide, which contained the direct repeat (DR) crRNA sequence alone (FIG. 2a). Expression of either Cas13a protein with the single- or multi-guide crRNA reduced viral accumulation by 72 hours post inoculation (hpi) (FIG. 5a). Virus accumulation was reduced by approximately 90% at 120 hpi, and TuMV interference by Cas13a was dependent on the expression of a crRNA with complementary sequence (FIG. 5b-d).

In traditional CRISPR-Cas experiments, the negative controls characterizing cells expressing the sgRNA or crRNA alone, without Cas, are generally omitted due to the assumption of Cas-dependence. Unexpectedly, we observed that expression of a single-guide or multi-guide crRNA alone, in the absence of the Cas13a protein, nonetheless inhibited viral accumulation (FIG. 2b and FIG. 6a). This was evidenced by reduced viral genome and derived protein accumulation. Viral RNA was also directly quantified using two independent NanoString nCounter probes, which allowed direct RNA quantification without the creation of complementary (c)DNA. Probes against two different regions of the TuMV genome confirmed that the single-guide and multi-guide caused virus interference when expressed with Cas13a, but also when expressed alone, in the absence of Cas13a (FIG. 2c and FIG. 6b). The NanoString quantification indicated that LbuCas13a plus guides provided greater viral interference compared to the single- or multi-guide alone. Among the samples expressing guide crRNA alone, the multi-guide consistently caused the greatest TuMV reduction compared to the single-guides (FIG. 2b,c and FIG. 6a,b)

Figure 7:
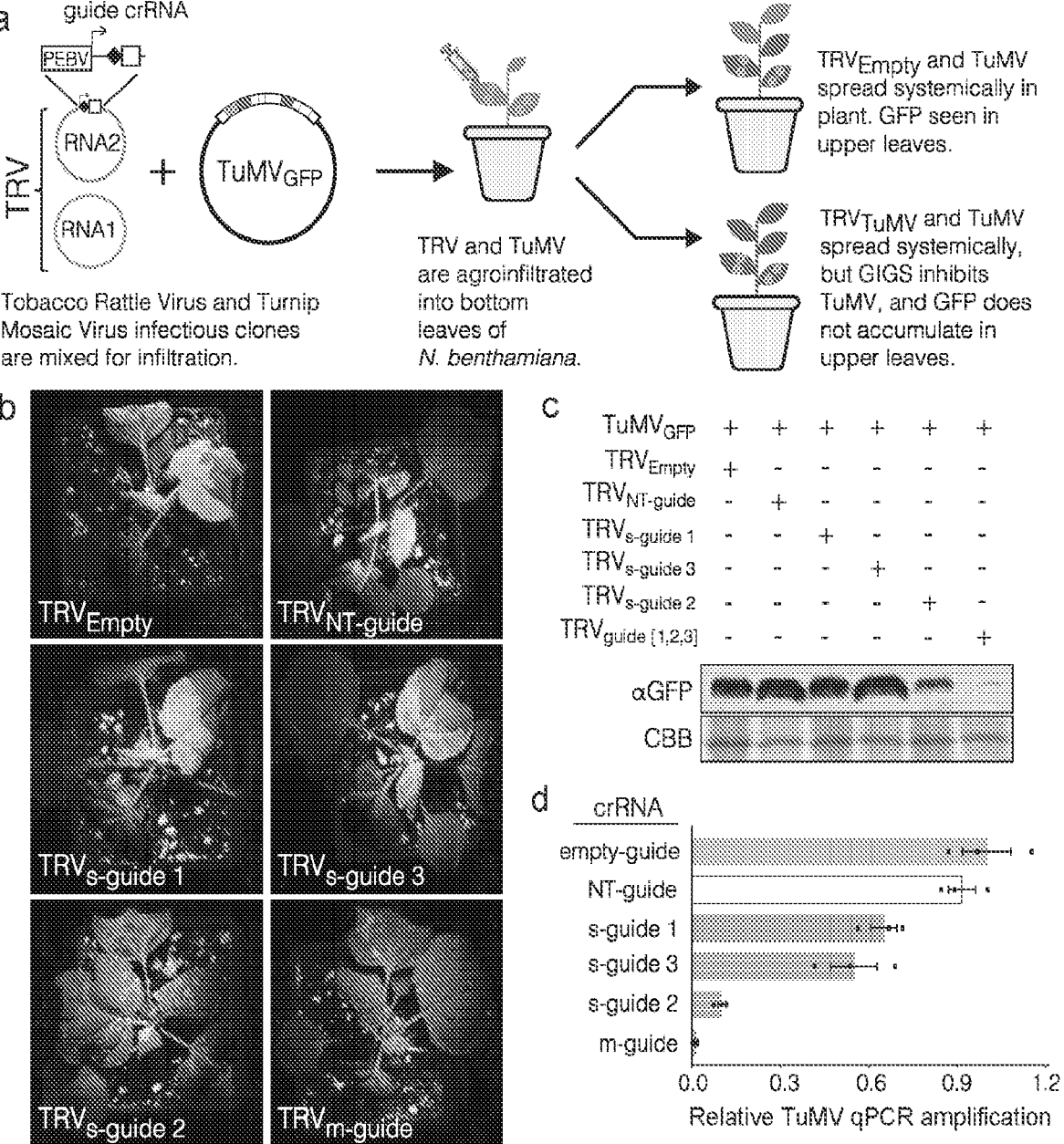
FIG. 7 shows data demonstrating that GIGS can function systemically to achieve virus interference. a, Schematic diagram of the TRV expressing guide crRNAs and TuMV expressing GFP. The two infectious clones are mixed and agroinfiltrated into *N. benthamiana*. At 7 days post inoculation, plants are visualized under a GFP lamp. TRV expressing an empty or NT-guide does not target TuMV and GFP accumulates in upper leaves. TRV expressing crRNA targeting TuMV results in GIGS and they fail to accumulate GFP. b, Representative images of *N. benthamiana* plants under UV light at 7 days post inoculation. The systemic movement of TuMV is evident based on the accumulation of GFP flourescence. The single-guide 2 (s-guide 2) and multi-guide (m-guide) stopped systemic TuMV infection. c, Upper leaves were checked for GFP accumulation by western blot corresponding to images shown in (b). The GFP antibody panel ($\alpha$GFP) shows GFP signal while commassie brilliant blue panel (CBB) shows protein loading. d, The TuMV genome was quantified from three independent plants (shown as black points) using qPCR. The mean and standard deviation are shown as barplots. Samples were standardized to the EF1$\alpha$ endogenous transcript and normalized to the empty-guide control levels.

To determine whether the guide crRNA alone can function systemically, GIGS-mediated TuMV interference was tested using the tobacco rattle virus (TRV) expression system. Plants were co-inoculated with TuMV expressing GFP and TRV, which systemically produced single- and multi-guide crRNA in the absence of Cas13 (FIG. 7a). At 7 days post inoculation (dpi), GFP-fluorescent from TuMV was observed in the upper systemic leaves of plants co-inoculated with either TRV expressing an empty-guide or a non-targeting (NT)-guide, which showed that systemic TRV delivery alone did not interfere with TuMV replication, movement, or translation (FIG. 7b-d). Samples expressing the two single-guides, guide 1 and 3, also accumulated visible GFP fluorescence in upper, non-inoculated leaves, indicating the spread of TuMV. Unexpectedly, TRV expressing either single-guide 2 or the multi-guide caused a significant reduction in GFP-fluorescence in the upper systemic leaves (FIG. 7b,c). Quantitative assessment of TuMV accumulation by qPCR showed an approximately 90% reduction in TuMV accumulation in samples expressing single-guide 2 and the multi-guide (i.e., GIGS) (FIG. 7d). Moreover, qPCR revealed an approximate 30% to 40% reduction in TuMV levels when TRV expressed single-guide 1 or -guide 3, which was not obvious from visual inspection of GFP fluorescence. This may reflect complicated translation mechanisms viruses employ, such as internal ribosome entry, in which the viral molecule was targeted by GIGS and partially interfered with, while intact GFP open reading frame sequence was still translated. These results indicate that GIGS can cause systemic TuMV interference, but that not all crRNA target sequences work as effectively. Variation for crRNA effectiveness has been reported for Cas13-dependent RNA targeting, likely caused by secondary structure and accessibility of the target RNA.

Viruses manipulate host physiology and have unique features unlike host derived RNAs, making it possible that the observation of guide crRNA alone silencing was a phenomena strictly related to viral RNA. To test this hypothesis, we targeted endogenous phytoene desaturase (PDS) mRNA with single-guide and multi-guide crRNA with and without LbuCas13a (FIG. 8). Agrobacterium-mediated expression of single- and multi-guide crRNA with and without LbuCas13 caused a significant reduction in PDS transcript levels compared to expressing LbuCas13a alone or with a NT-guide (FIG. 2d). The resulting mRNA reduction (75-85%) was consistent across the tested samples, comparable to a PDS-hairpin construct known to induce RNAi (FIG. 2d). The reduction in PDS mRNA was confirmed by northern blot, which showed a clear reduction for PDS signal for both LbuCas13a-depenedent and GIGS compared to expressing LbuCas13a alone, with a NT-guide, or from an untreated leaf (FIG. 9a). Direct RNA quantification by NanoString further confirmed a significant reduction for the PDS transcript for samples expressing the PDS targeting guides with or without the expression of Cas13a (FIG. 9b). These results show the phenomena is not specific for viral RNA and extend the observation of guide crRNA alone silencing to endogenous genes.

Figure 10:
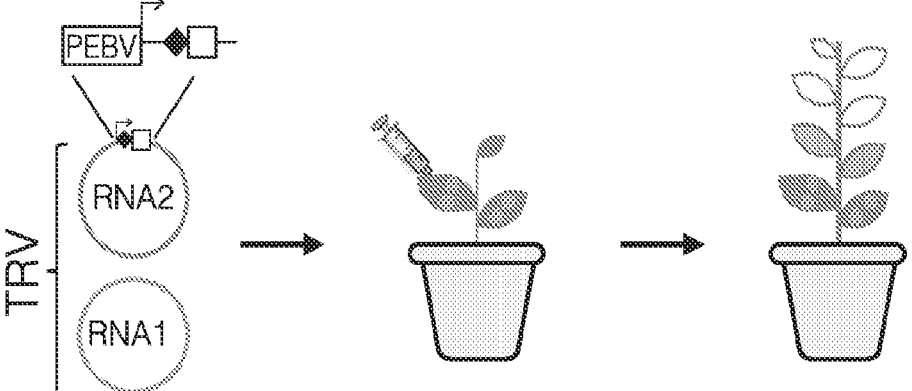
FIG. 10 is an illustration of the experimental design for systemic endogenous mRNA reduction by GIGS. Schematic of the TRV expression vector system (RNA1 and 2). RNA2 was engineered to contain the pea early browning virus (PEBV) promoter to express single-, multi-, and NT-guides. An antisense fragment (371 bp) to PDS was also inserted into the RNA2 cloning sight to induce RNAi against PDS. Infectious clones are agroinfiltrated. TRV moves systemically in the plant, delivering the respective guide crRNA. Those that cause PDS mRNA silencing result in a bleaching phenotype (i.e. white sectors) seen on upper leaves.
Figure 11:
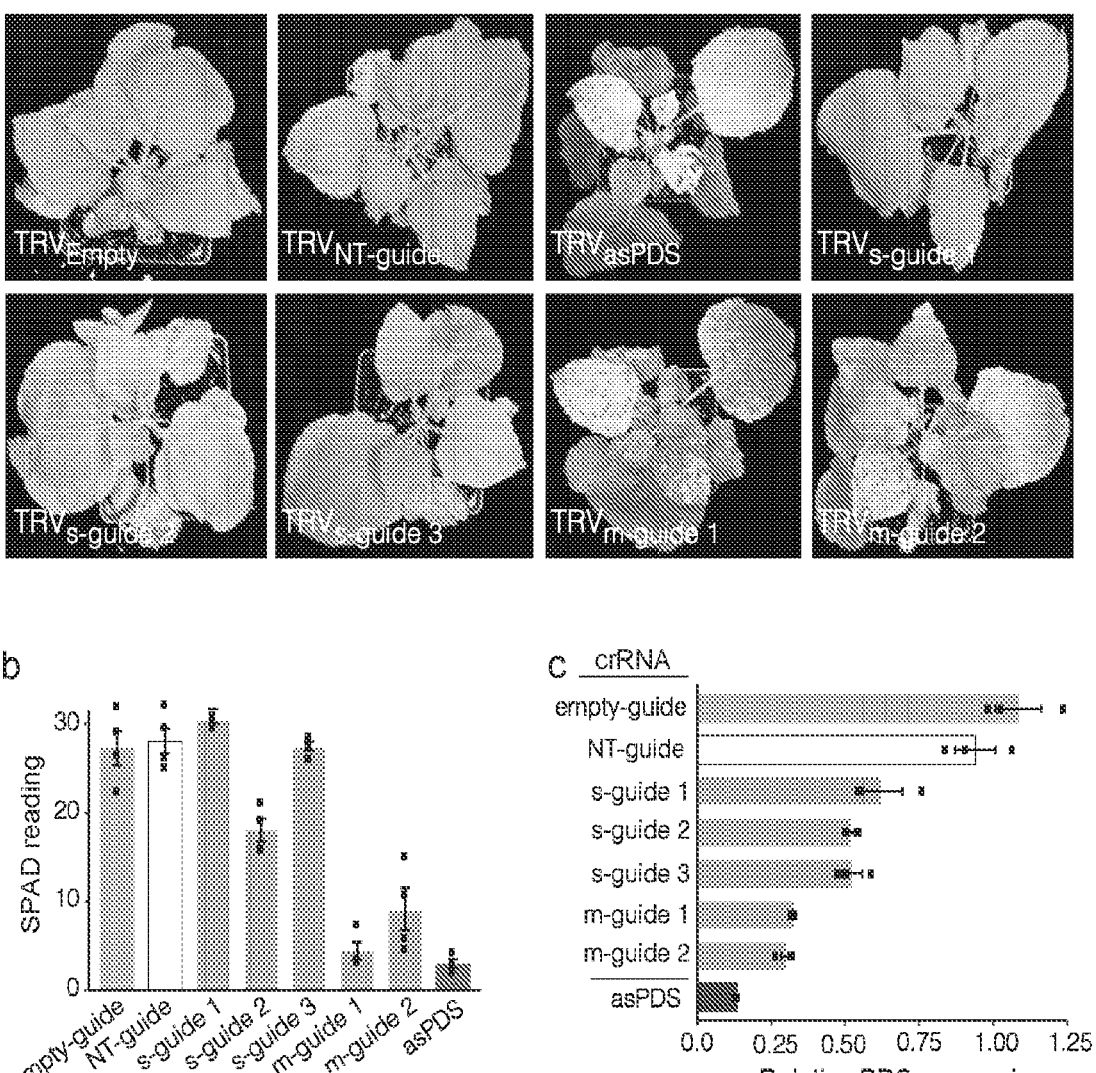
FIG. 11 provides data showing systemic endogenous mRNA reduction by GIGS. a, Representative images of *N. benthamiana* plants two weeks post TRV inoculation. TRV moved systemically to the top portion of the plant and expressed guide crRNAs targeting PDS or controls. Photobleaching caused by PDS mRNA reduction is visible as white or yellow sectors in the upper leaves. Each image is labeled with the guide delivered by TRV. b, SPAD meter readings from photobleached areas of leaves. One reading was taken per infiltrated plant. Three independent plants were infiltrated. c, The PDS transcript was quantified using qPCR from three independent leaves. Data from each sample is shown as a black point with the mean and standard deviation shown as a boxplot. Samples were standardized to the EF1α endogenous transcript and normalized to the empty-guide control levels.

To test if guide crRNA alone silencing acts systemically on endogenous genes, TRV expressing guides targeting endogenous PDS mRNA were infiltrated into N. benthamiana (FIG. 10). Under the hypothesis that GIGS can act systemically on endogenous genes, the hope was that TRV-delivered guides would result in photobleaching in TRV-infected tissues. Three single-guide crRNA, targeting different regions of PDS, did not exhibit significant photobleaching (FIG. 2e). However, two multi-guide constructs targeting different PDS regions displayed substantial photobleaching in systemic leaf tissue (FIG. 2e and FIG. 11a). Interestingly, the visible photobleaching pattern induced by the anti-sense hairpin fragment (i.e. RNAi) and that induced by GIGS were not the same (FIG. 2e and FIG. 11a). While the antisense RNAi photobleaching was strong in the upper, youngest leaves, GIGS induced photobleaching was not visible in the upper most leaves, and the photobleaching occurred in more distinct segments causing a patchy appearance. Quantifying the photobleaching to confirm the phenomena, SPAD meter readings showed a significant reduction in chlorophyll content for samples expressing the multi-guide crRNAs and the antisense PDS fragment (FIG. 11b). Plants that expressed single-guide 2 were yellow and also showed a reduced SPAD reading (FIG. 11a,b). Quantifying PDS transcripts with qPCR showed that the PDS transcript level was reduced (30-45%) for the three single-guides, and to a greater extent by the multi-guides (65-70%) and the antisense construct (85%) (FIG. 11c). It is not clear why single-guide 1 and 3 caused a reduction in PDS mRNA levels, but did not result in visible photobleaching or SPAD meter reductions, but we note that the reduced PDS mRNA levels are consistent with that seen using Agrobacterium-mediated spot infiltration (e.g., FIG. 2d and FIG. 9). Also, the results clearly showed that GIGS induced by multi-guide constructs caused the greatest reduction in target transcript levels for both virus and endogenous RNA targeting.

Figure 3:
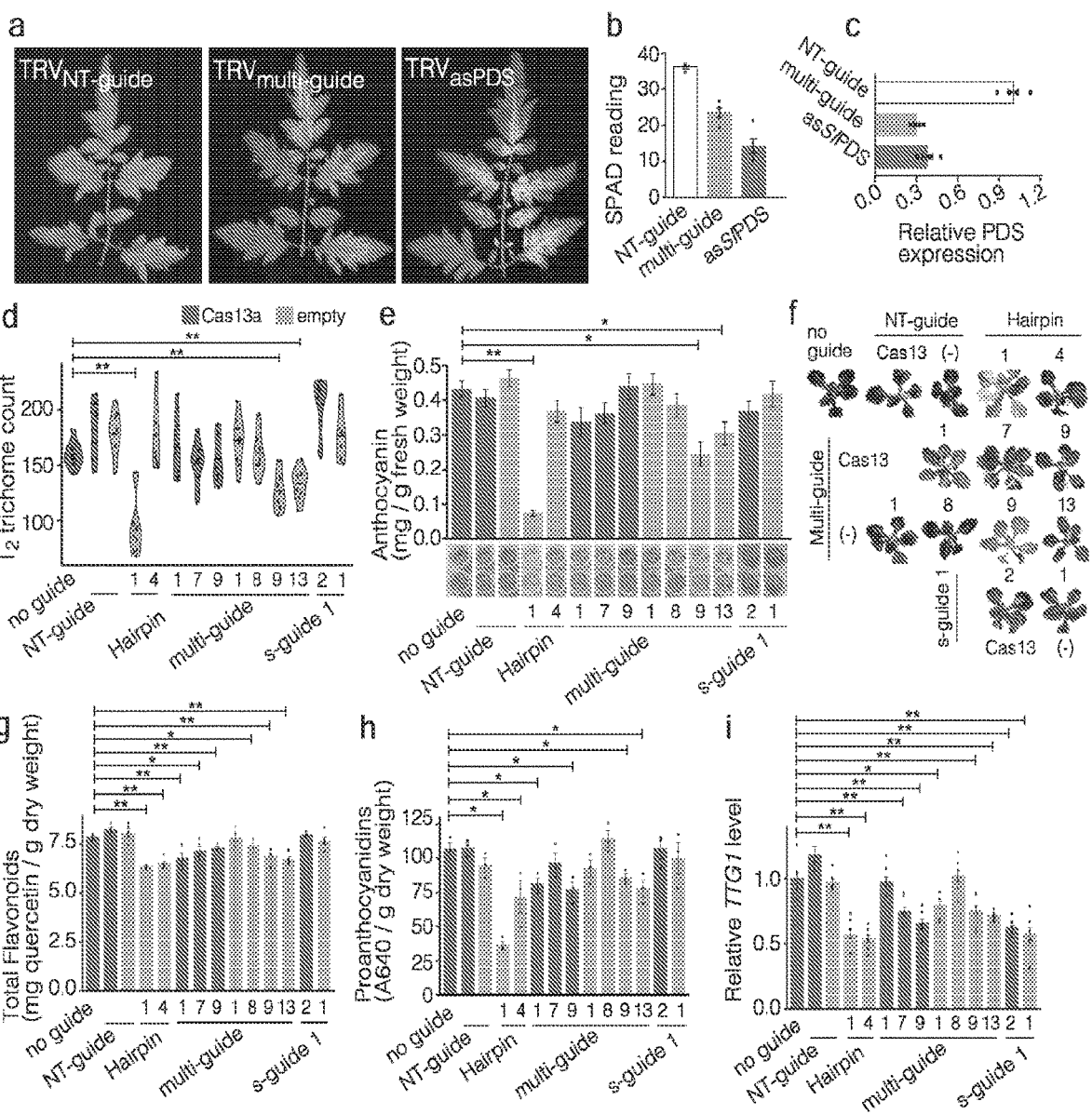
FIG. 3 shows data demonstrating that Cas13 and GIGS function across plant species and are heritable. a, Representative images of tomato leaves following TRV systemic movement and photobleaching induced by GIGS ($TRV_{m\text{-}guide}$) and an antisense transcript ($TRV_{asPDS}$). TRV expressing a non-targeting guide crRNA ($TRV_{NT\text{-}guide}$) does not induce photobleaching. b, Measurements of chlorophyll content from SPAD meter readings for three independent plants. SPAD meter reading where taken from leaf sections showing photobleaching, and individual reading are shown as black points with the mean and standard deviation shown as a bar plot. c, qPCR measurement of the PDS transcript standardized to the EF1a transcript and relative to the NT-guide sample. Three independent samples were analyzed and individual data are shown as black points with the mean and standard deviation shown as bar plots. (d-i), Data for independent transgenic *Arabidopsis* lines. Data for plants expressing LbuCas13a are shown in dark blue and plants not expressing the protein are shown in light blue. Control lines expressing a hairpin construct against the TTG1 transcript are shown in grey. d, Trichome counts from the seventh leaf of T2 *Arabidopsis* lines. Ten plants were counted per independent line, listed below graph, with the individual counts shown as black points and the distribution represented as a violin plot. e, Leaf anthocyanin quantification from $T_3$ seedlings following sucrose treatment. Representative wells follow extraction shown below each bar plot. f, Representative plantlets following sucrose treatment showing anthocyanin pigmentation (i.e. purple color). g, Total flavonoids extracted from seeds collected from $T_2$ plants. Five independent seeds lots were analyzed per line, shown as black points. h, Seed proanthocyandin quantification from the same plants analyzed in (g). i, Quantification of the TTG1 transcript from three $T_2$ and three $T_3$ plants per line, individual data shown as black points. Statistical comparisons were made between the transformation control (no guide) and each treatment using a one-sided Mann-Whitney U-test with Benjamini-Hochberg (BH) multiple testing correction. Samples with p-values less than 0.05 (*), and 0.01 (**) are indicated.

An important question is whether GIGS is specific to N. benthamiana or is more broadly active in plants. To test this, multi-guide crRNA constructs were developed to target PDS in tomato (Solanum lycopersicum), which were delivered using TRV, along with a NT-guide and an antisense PDS control. We observed visible photobleaching in upper leaves of S. lycopersicum plants following systemic movement of TRV expressing a multi-guide targeting S. lycopersicum PDS, although the photobleaching was not as widespread as that produced by the antisense PDS construct (FIG. 3a). Quantifying chlorophyll levels and the PDS transcript indicated that photobleached tissue from GIGS and antisense expressing TRV both had substantially lower levels compared to the control (FIG. 3b,c). These results show that GIGS is active outside of N. benthamiana, possibly extending to other plants in the Solanaceae family.

Another important question is whether GIGS requires bacterial or viral machinery (i.e., proteins) introduced during transient expression or if GIGS functions in stable transgenics through plant endogenous machinery. To test this, we transformed Arabidopsis thaliana (Col-0) with single-guide and multi-guide crRNA targeting the pleiotropic regulator TRANSPARENT TESTA GLABRA1 (TTG1), both with and without LbuCas13a. The TTG1 gene encodes a WD40 repeat protein, which interacts with MYB and bHLH transcription factors required for normal trichome and root hair development, along with seed proanthocyanidin and veg-etative anthocyanin production. The average trichome counts for multiple independent $T_1$ plants that expressed LbuCas13a with either single-guide or multi-guide crRNA had significantly fewer trichomes compared to wild-type, and importantly, plants expressing single-guides and the multi-guide crRNA, without Cas13, also had significantly fewer trichomes on average (FIG. 12a). The TTG1 transcript was quantified in $T_1$ plants and was highly variable across the transformed lines (FIG. 12b). Individual plants were selected, self-fertilized and seeds from $T_1$ plants showed reduced total flavonoids in both Cas13 and GIGS lines, consistent with reduced TTG1 (FIG. 12c).

We assessed whether GIGS would function in progeny inheriting guides by characterizing individual lines in the $T_2$ and $T_3$ generations for altered TTG1 phenotypes. Trichome counts of the seventh leaf (from ten plants per line) indicated that two GIGS lines (i.e., expressing only a multi-guide crRNA targeting TTG1), and one of the hairpin expressing lines had significantly fewer trichomes compared to the transformation control expressing Cas13a alone (FIG. 3d). Individual transformed lines were subjected to sucrose and light stress to induce leaf anthocyanin production, and we again observed that two lines expressing multi-guide crRNA targeting TTG1 (i.e., GIGS) displayed significantly reduced leaf anthocyanin levels, along with a hairpin expressing line (FIG. 3e,f). Quantification of total seed flavonoids showed a significant but modest reduction compared to the control line, for both Cas13 expressing and GIGS lines along with both hairpin expressing lines (FIG. 3g). As total flavonoid quantification measures products of both TTG1-dependent and -independent pathways, we measured seed proantho-cyanidins to more accurately measure the impact of TTG1 reduction. This analysis identified the same transformed lines as having significantly lower proanthocyanidins as overall reduced flavonoids, but the level of reduction was more substantial (FIG. 3h).

Figure 13:
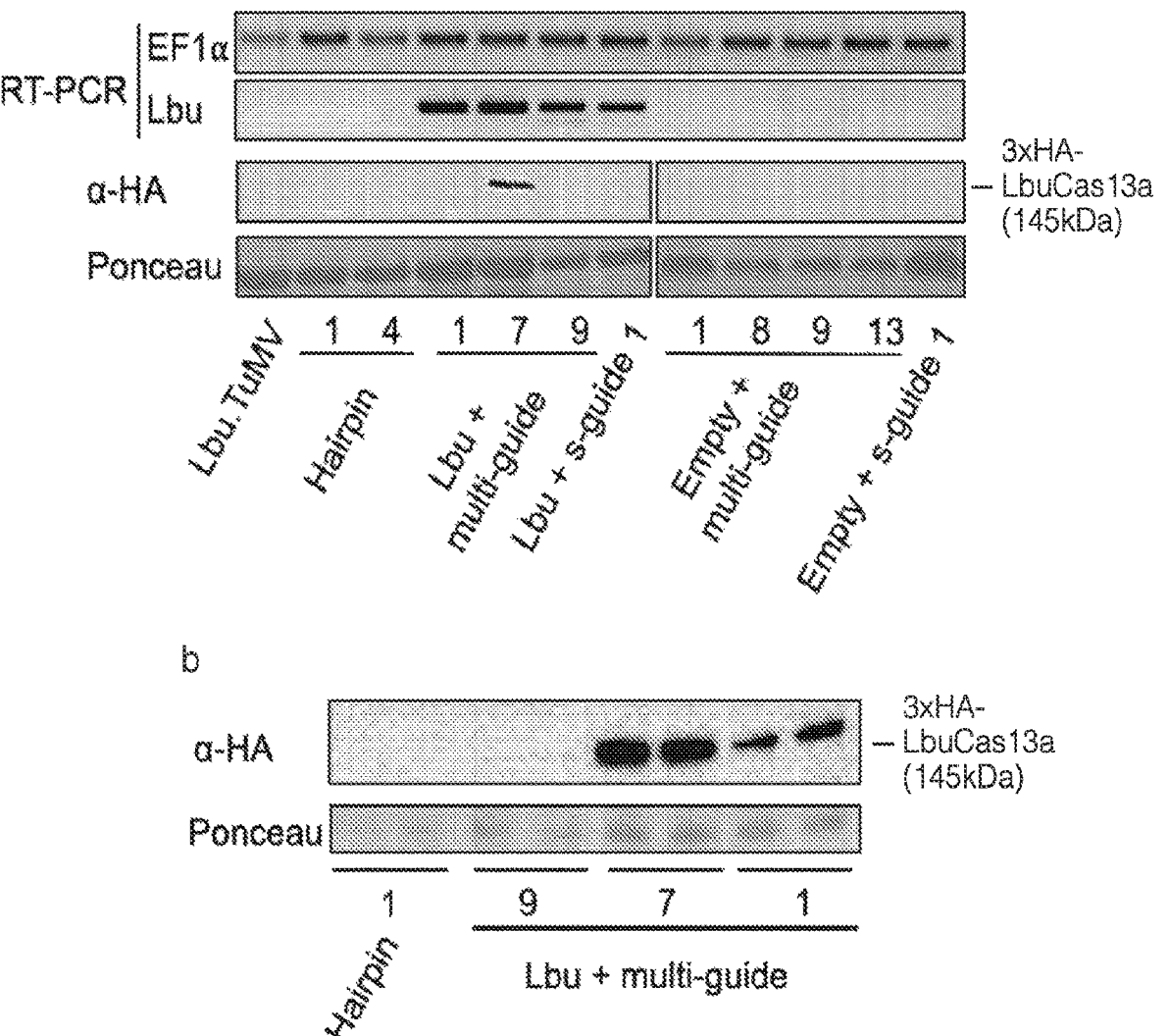
FIG. 13 provides data showing expression and translation products of Cas13 transgenic *Arabidopsis*. a, The Cas13 transcript is only detected using reverse-transcription PCR (RT-PCR) in lines transformed with the LbuCas13a transgene (Lbu, top panel). The endogenous transcript coding for Elongation factor 1 alpha (EF1α) is shown as a control. The western blot panel using an anti-HA antibody (α-HA) detected a single band corresponding to the size of the 3×HA-LbuCas13a protein (145 kDa). Ponceau strain was used a protein loading control. b, Protein was isolated from the same lines used in (a) and re-analyzed by western blot. Higher exposure time detected a single band corresponding to 3×HA-LbuCas13a in line #1 as well as line #7. The results indicate likely differences in protein translation or possibly stability between the different transgenic lines.

These results indicate heritable phenotypes for multiple traits mediated by both Cas13 and GIGS in stable transgenic *Arabidopsis* when targeting the pleiotropic regulator TTG1. We do note there was substantial phenotypic variation among lines with the same construct, despite significant reduction in TTG1 levels (FIG. 3i). This is in part explained by variation in transgene expression and translation (FIG. 13). In addition, more complicated mechanisms such as asynchronous TTG1 expression and Cas13 or GIGS expres-sion at the individual cell level, or the effect of incomplete TTG1 silencing on trait manifestation (i.e., kinetics of silencing to produce a phenotype). Optimizing Cas13 and GIGS approaches will be an important step to deliver robust biotechnology platforms for plant research and crop improvement, particularly for tissue- or temporal-specific expression that is difficult to manipulate precisely with CRISPR-Cas9.

Figure 4:
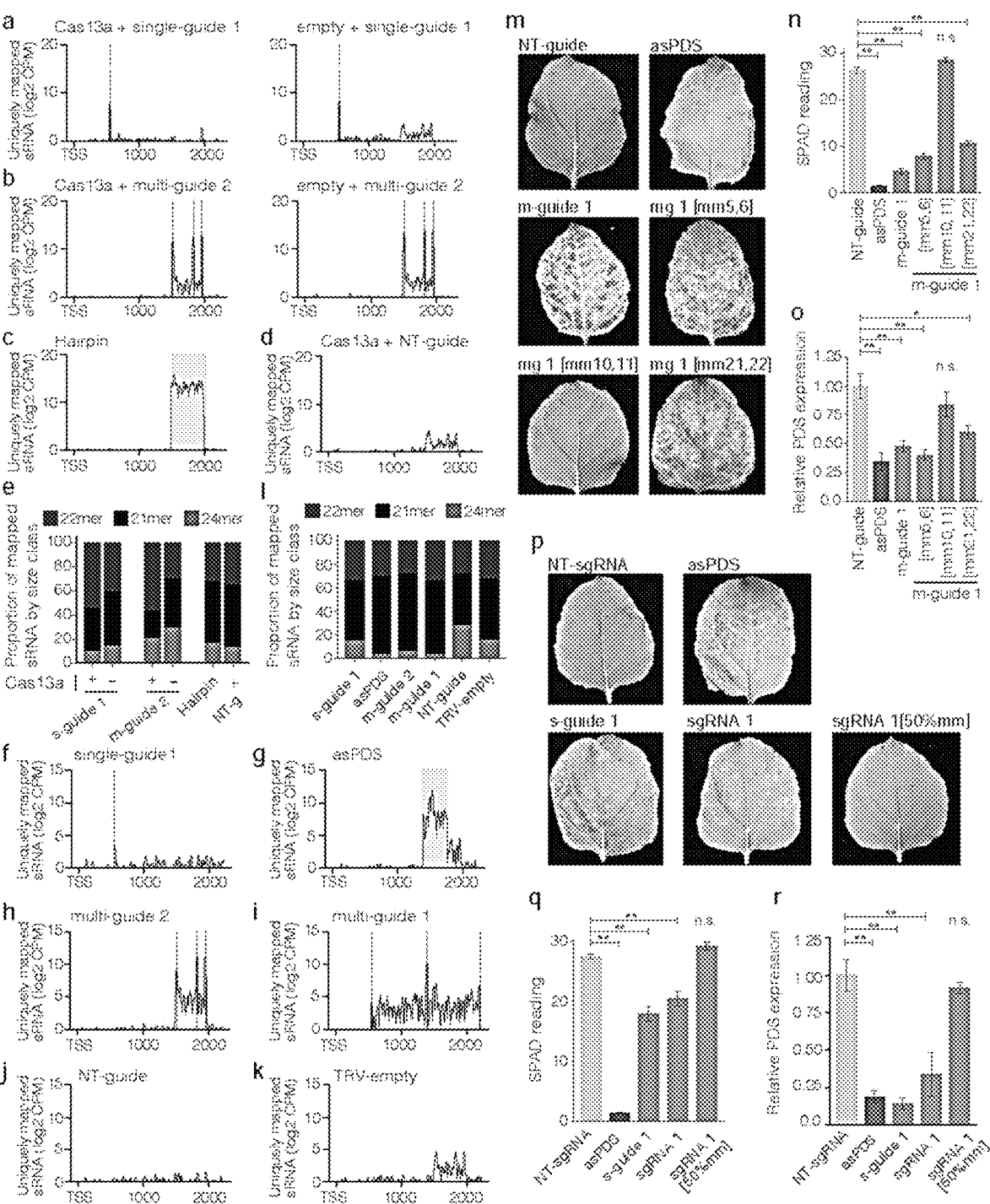
FIG. 4 shows data demonstrating that GIGS is mediated by components of RNAi. (a-d), Uniquely mapped read counts to the PDS transcript collected from agroinfiltrated spots. The summary of read mapping is shown relative to the transcription start site (TSS) till the end of the predicted mRNA (2216 bp). Reads counts are shown as log 2 of counts per million+1 (CPM) averaged between the two replicates per treatment, which are listed above the plots. The position of the expressed single- and multi-guide crRNA are shown as vertical dashed line(s). The region spanning the hairpin construct is shown as a grey window. (e), Proportion of 21, 22, and 24 nt mapped sRNA to the PDS transcript averaged from two replicates. (f-l), similar to (a-e) but data collected from systemic leaves following TRV expression. (m), Representative images of leaves following TRV systemic delivery of multi-guide 1 (m-guide 1) targeting PDS, in addition to three variants of m-guide 1 that contained two base pair mismatches at each of the three guide crRNA. The mismatches were at positions 5,6 (mg 1[mm5,6]), positions 10,11 (mg 1[mm10,11]), and positions 21,22 (mg 1[21,22]). Controls include expressing TRV with a non-targeting guide (NT-guide) and TRV with a region of antisense sequence to PDS (asPDS). Photobleaching is seen as a loss of green color. (n), SPAD meter readings from photobleached leaf samples as described for (m). Data collected from a total of six independent leaves from two experiments. (o), Quantification of the PDS transcript using qPCR for the same samples as measured in (n). Data standardized to an endogenous transcript and normalized to the TRV expressing the NT-guide. (p), Representative images of leaves following TRV systemic delivery of single-guide 1 (s-guide 1) targeting PDS, and a Cas9 designed sgRNA designed to contain the same 28 bp targeting PDS as in s-guide 1. An sgRNA 1 control was expressed that contained the sequence in sgRNA 1, but with 50% mismatches to the PDS transcript (sgRNA 1[50% mm]). Control sgRNA were expressed with non-targeting guide sequence (NT-sgRNA). Photobleaching is seen as a loss of green color in the asPDS sample, while interveinal yellowing is visible in the samples expressing s-guide 1 and sgRNA 1. (q), SPAD meter readings from photobleached leaf samples as described for (p). Data collected from a total of six independent leaves from two experiments. (r), Quantification of the PDS transcript using qPCR for the same samples as measured in (q). Data standardized to an endogenous transcript and normalized to TRV expressing NT-sgRNA. Statistical comparisons were made between the NT-guide or NT-sgRNA and each treatment using a one-sided Mann-Whitney U-test with Benjamini-Hochberg (BH) multiple testing correction. Samples with p-values less than 0.05 (*), and 0.01 (**) are indicated. n.s., non-significant difference (p>0.05) as measured by Mann-Whitney U-test.

We sought to understand the mechanism giving rise to guide crRNA alone reducing viral and endogenous RNA levels. Given that crRNA are composed of short antisense sequences, it is possible that GIGS functions through com-ponents of the endogenous RNA interference (RNAi) path-way. However, the structure of crRNA used here are very different from the hairpin RNA, small interfering RNA (siRNA), or micro RNA (miRNA) used for traditional RNAi, therefore it is not obvious how crRNA might enter or induce RNAi. Alternatively, it is possible that GIGS elicits other endogenous endo- or exonucleolytic RNA degradation pathways. Since small RNA (sRNA) usually in the range of 21- to 24-nucleotides (nt) are a hallmark for RNAi, we reasoned that if GIGS functions through RNAi, abundant sRNA could be identified. To assess this, we conducted small (s)RNA-seq from *N. benthamiana* samples expressing single and multi-guide crRNA against the endogenous PDS transcript. Mapped sRNA for the single-guide samples showed a single sharp peak at the PDS transcript, which corresponds to the location of the crRNA guide sequence, regardless of Cas13 expression (FIG. 4a). Likewise, the samples expressing the multi-guide crRNA had three distinct peaks of mapped sRNA, each corresponding to the location of the targeting guide sequence. Expectedly, in these samples we also identified many sRNA mapping to the PDS transcript that were independent from the multi-guide target sequence (FIG. 4b). Interestingly, these sRNA were identi-fied only between the 5' and 3' boundaries of crRNA targeting sites and do not appear to extend past this region (FIG. 4b). This was similar to the sRNA mapping from the samples expressing the PDS hairpin, which produced ample sRNA between the two ends of the hairpin fragment (FIG. 4c). While the most abundant peaks for the multi-guide crRNA samples corresponded to the guide targets them-selves, the identification of thousands of sRNA reads between these target regions suggest the production of secondary sRNA using the GIGS constructs. We do note the presence of background sRNA in the samples where Cas13 was expressed with a NT-guide, which may indicate back-ground read mapping or potentially RNA contamination during library preparation, but regardless, the signal was low (FIG. 4d). Supporting the idea that GIGS results in the production of secondary sRNA through RNAi, we identified more 21 nt sRNA (i.e., siRNA) mapped to the PDS transcript during GIGS (i.e. without the Cas13 protein) than when Cas13 was expressed with the guide (FIG. 4e). To further determine sRNA production during GIGS, a second sRNA-seq experiment was conducted by expressing either a single-guide or one of two multi-guide crRNA in the absence of Cas13 using the TRV vector in *N. benthamiana*. The mapped sRNA from the single-guide had a clear but small peak corresponding to the guide target sequence, along with other background mapped sRNA (FIG. 4f). In contrast, mapped sRNA from the sample expressing a PDS antisense fragment produced many sRNA, which mapped between the ends of the antisense fragment (FIG. 4g). Both multi-guide crRNAs showed three sharp peaks of mapped sRNA, with each peak corresponding to a guide targeting region (FIG. 4h,i). Impor-tantly, these samples clearly have many mapped sRNA that are independent of the expressed multi-guide sequences, which are not present in the controls, and intervene the regions targeted by the multi-guide crRNA (FIG. 4h-i). We interpret these sRNA to represent secondary sRNA gener-ated in response to multi-guide GIGS. Consistent with these secondary sRNA being generated via components of the RNAi pathway, the length of sRNA mapped to the PDS transcript are predominantly 21 nt for the two multi-guide and antisense fragment samples (FIG. 4l). These results suggest that siRNA and RNAi could be involved in medi-ating GIGS.

Figure 15:
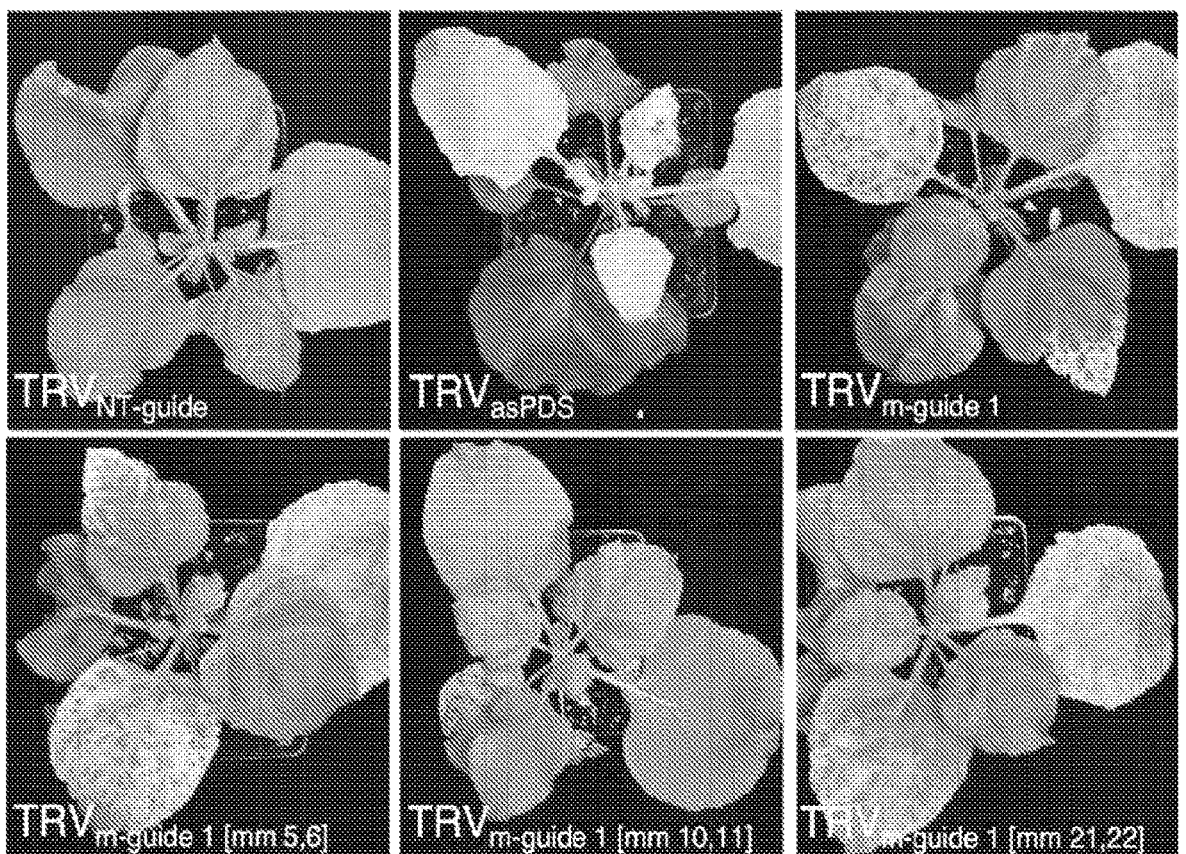
FIG. 15 shows data demonstrating that guide crRNA with mismatches at base pairs 10,11 do not elicit GIGS. Representative images of plants following Tobacco Rattle Virus (TRV) systemic movement. Plants infected with TRV expressing a non-targeting guide crRNA (NT-guide) have a normal green leaf appearance. Plants infected with TRV containing an antisense phytoene desaturase (asPDS) fragment display photobleaching in upper leaves following TRV systemic movement and the triggering of RNAi PDS silencing. TRV expressing multi-guide 1 (m-guide 1), multi-guide 1 with mismatches between the target and guide at positions 5 and 6 (m-guide 1[mm 5,6]), or multi-guide 1 with mismatches at positions 21 and 22 (m-guide 1[mm 21,22]) also display photobleaching in upper leaves. Plants inoculated with TRV expressing multi-guide 1 with mismatches between the target and guide at positions 10 and 11 (m-guide 1[mm 10,11]) have the same normal green appearance as the NT-guide samples.

Under the hypothesis that GIGS requires endogenous RNAi machinery, target mRNA reduction would be depen-dent on ARGONAUTE (AGO) RNA-binding protein(s). AGO proteins are required to form the RNA Induced Silenc-ing Complex (RISC), which carries out the biochemical slicing or translational inhibition of target mRNA. To achieve AGO mediated endonuclease activity, perfect complementary base pairing is required at positions 10 and 11 between AGO-bound siRNA and the target mRNA (i.e., central duplex region). Therefore, if GIGS is dependent on AGO, we predicted that multi-guide crRNA designed to have mismatches at base-pairs 10 and 11 would be blocked for GIGS (i.e., no target mRNA reduction). To test this, multi-guide crRNA that contained specific two base pair mismatches to the PDS mRNA were delivered to *N. ben-* *thamiana* using TRV (FIG. 14). The results show that multi-guide crRNA against PDS with mismatches at the critical region for AGO endonuclease activity (i.e., base pairs 10,11) do not cause photobleaching, while negative control mismatches (i.e., positions 5,6 or 21,22) still elicit photobleaching (FIG. 4*m*, FIG. 15). Indeed, SPAD meter readings and PDS transcript quantification showed that the multi-guide with mismatches 10,11 were not reduced for the two traits when compared to the controls expressing TRV alone or a NT-guide crRNA (FIG. 4*n,o*). We note that the mismatches at 5,6 and 21,22 did affect silencing, as the perfectly complementary multi-guide crRNA gave the strongest photobleaching. These mismatches may interfere with other RISC functions, such as target recognition and target mRNA turnover. However, it is clear that mismatches at 10,11 abolish GIGS, while the other mismatches diminish it, suggesting that GIGS functions through one or more endogenous AGO proteins. Additionally, these results suggest that GIGS is mediated by RNA endonuclease reduction and not translational inhibition of target mRNA.

Figure 16:
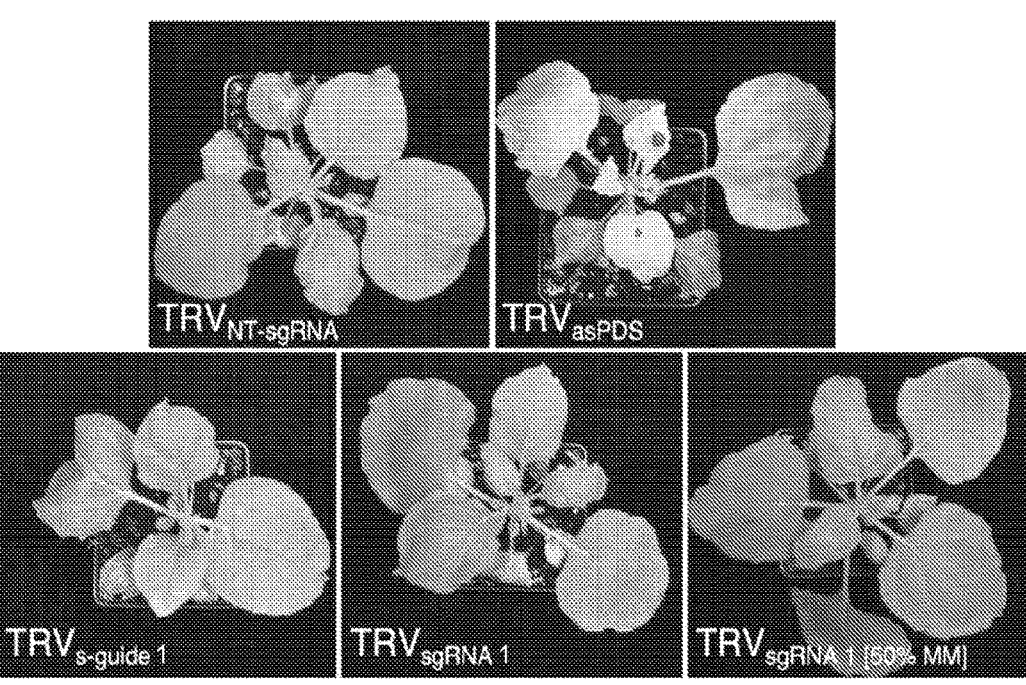
FIG. 16 shows data demonstrating that Cas9 sgRNA can elicit GIGS photobleaching in *N. benthamiana*. a, Schematic of guide designs targeting PDS transcript for Cas9 (single guide RNA, sgRNA) and Cas13 (single-guide, s-guide). Each guide contains 28 nt antisense to the PDS transcript (PDS spacer, grey window) at the 5' end. The Cas9 sgRNA control contained 50% mismatch sequence to the PDS transcript (sgRNA 1 [50% mm]). Mismatch nucleotides highlighted in red, while shared nucleotides are designated with an (*) under the alignment. The 3' end of the Cas9 crRNA contains the 78 base pair trans-activating crRNA (tracrRNA, green). The Cas13 crRNA contains the 37 bp direct repeat (DR, beige). Total length for each crRNA is shown to the right of each crRNA. b, Representative whole plant images showing GIGS induced photobleaching. Plants expressing the control non-targeting single guide RNA (NT-sgRNA) from TRV do not display any abnormal leaf color. Strong photobleaching is seen from plants expressing TRV containing an antisense PDS fragment (asPDS). Clear phenotypic differences in leaf greenness are seen when TRV expressed Cas13 (s-guide 1) or Cas9 (sgRNA 1) designed crRNA against PDS. These plants show interveinal yellowing. The control Cas9 crRNA with 50% mismatches to the PDS transcript (sgRNA 1[50% mm]) does not display any visible alteration in leaf greenness.

During preparation of this work, it was reported in a mosquito system that crRNA guides from the Cas13b system cause target mRNA reduction in the absence of Cas13b, termed Cas13b-independent silencing. That report does not provide functional data that elucidate the mechanism, but the authors postulate that Cas13b-independent silencing is related to RNAi. We posit that the findings described in mosquito suggest that GIGS functions broadly across eukaryotes. If this is true, we were interested to address if GIGS is active for other guide crRNA, such as for the CRISPR-Cas9 system. To this end, we tested if a single-guide that elicited PDS mRNA reduction when designed as a Cas13 crRNA could additionally reduce target mRNA when designed as a 28 nt Cas9 sgRNA (FIG. 16*a*). When the Cas9 designed sgRNA was delivered by TRV, we observed subtle yellowing in the leaves compared to TRV expressing a NT-guide, similar to that produced by the Cas13 crRNA design (FIG. 4*p*). Importantly, a control Cas9 designed sgRNA containing 50% mismatches to the PDS sequence shows no yellowing, indicating that this subtle phenotype is specific (FIG. 4*p* and FIG. 12*b*). Quantifying these results, we saw that the sgRNA designed against PDS resulted in approximately 28% reduction in SPAD meter readings, and variable PDS transcript reduction (25-90%) compared to the NT-guide and the 50% mismatch sgRNA controls (FIG. 4*q,r*).

In summary, we report that Cas13a can effectively reduce targeted viral and endogenous RNA levels. Unexpectedly, we also discovered that the guide crRNA designed for the Cas13a system can also reduce viral and endogenous RNA in the absence of the Cas13 protein (i.e., guide crRNA alone) in the three plant species tested. We also provide evidence that GIGS elicits small RNA and is dependent on AGO for target mRNA reduction, strongly implicating that GIGS functions via endogenous RNAi machinery. Further research is needed to understand how crRNA guides enter or elicit the RNAi pathway, the interplay between RNAi and Cas13-mediated silencing, and how broadly GIGS functions across eukaryotes. The work presented here suggests that GIGS can achieve target RNA silencing using a guide sequence that is shorter than conventional hairpin and anti-sense constructs used in plants, which could be particularly important for targeting multigene families. Additionally, this could afford a higher target specificity compared to RNAi, while avoiding the need to express a Cas13 transgene, which could facilitate crop biotechnology.

Materials and Methods

Designing CRISPR-Cas13a Machinery for in Planta Expression

To develop prokaryotic CRISPR-Cas13a machinery as a platform for in planta transcript-silencing, sequences of LbuCas13a and LbaCas13a effectors were *N. benthamiana* codon optimized along with 3× FLAG tag at the N-terminal were custom synthesized from Genscript (Piscataway, NJ).

TABLE

Plasmids and gene sequences

| Name of sequence | SEQ ID NO: |
| --- | --- |
| 3x-HA-LbuCas13a | 1 |
| 3X-FLAG-tagged LbaCas13a | 2 |
| *Nicotiana benthamiana* PDS cDNA | 3 |
| *Solanum lycopersicum* PDS cDNA | 4 |
| *Arabidopsis* TTG1 cDNA | 5 |
| PDS-hairpin | 6 |
| pGWB413 | 7 |
| pTRV1 | 8 |
| pTRV2 | 9 |
| TuMV-GFP | 10 |
| pENTR-AtU6:LbuDR:BsaI | 11 |
| pENTR-AtU6:LbaDR:BsaI | 12 |
| pCR8:PEBV:LbuDR:BsaI | 13 |

These fragments were assembled using HiFi DNA assembly (New England Biolabs, Ipswich, MA). The integrity of the constructs was confirmed by Sanger sequencing (Genewiz, South Plainfield, NJ).

Turnip mosaic virus engineered to express GFP (TuMV-GFP) and the endogenous phytoene desaturase (PDS) gene were selected as targets for CRISPR-Cas13a interference. For crRNA designs, Lba- or LbuCas13a specific direct repeats with 28 nucleotide spacer sequences complementary to the target were expressed by the *Arabidopsis thaliana* U6 promoter.

TABLE

Backbones for cRNA cloning and expression

| Name of sequence | Sequence (5'-3') | Purpose | SEQ ID NO |
| --- | --- | --- | --- |
| AtU6 promoter | TGATCAAAAGTCCCACATCGAT CAGGTGATATATAGCAGCTTAG TTTATATAATGATAGAGTCGAC ATAGCGATT | Express crRNA | 14 |
| PEBV promoter | AATTCGAGCATCTTGTTCTGGG GTTTCACACTATCTTTAGAGAA AGTGTTAAGTTAATTAAGTTAT CTTAATTAAGAGCATAATTATA CTGATTTGTCTCTCGTTGATAG AGTCTATCATTCTGTTACTAAA AATTTGACAACTCGGTTTGCTG ACCTACTGGTTACTGTATCACT TACCCGAGTTAACGAG | Express crRNA using pTRV2 | 15 |
| Lbu crRNA cloning backbone | GATTTAGACCACCCCAAAAATG AAGGGGACTAAAACAaGAGACC TTTTTTTTTTGAGACC | Cloning crRNA | 16 |
| Lba crRNA cloning backbone | GCTGGAGAAGATAGCCCAAGAA AGAGGGCAATAACGGTCTCGTA ACTTTTTGAGACC | Cloning crRNA | 17 |

Figure 2:
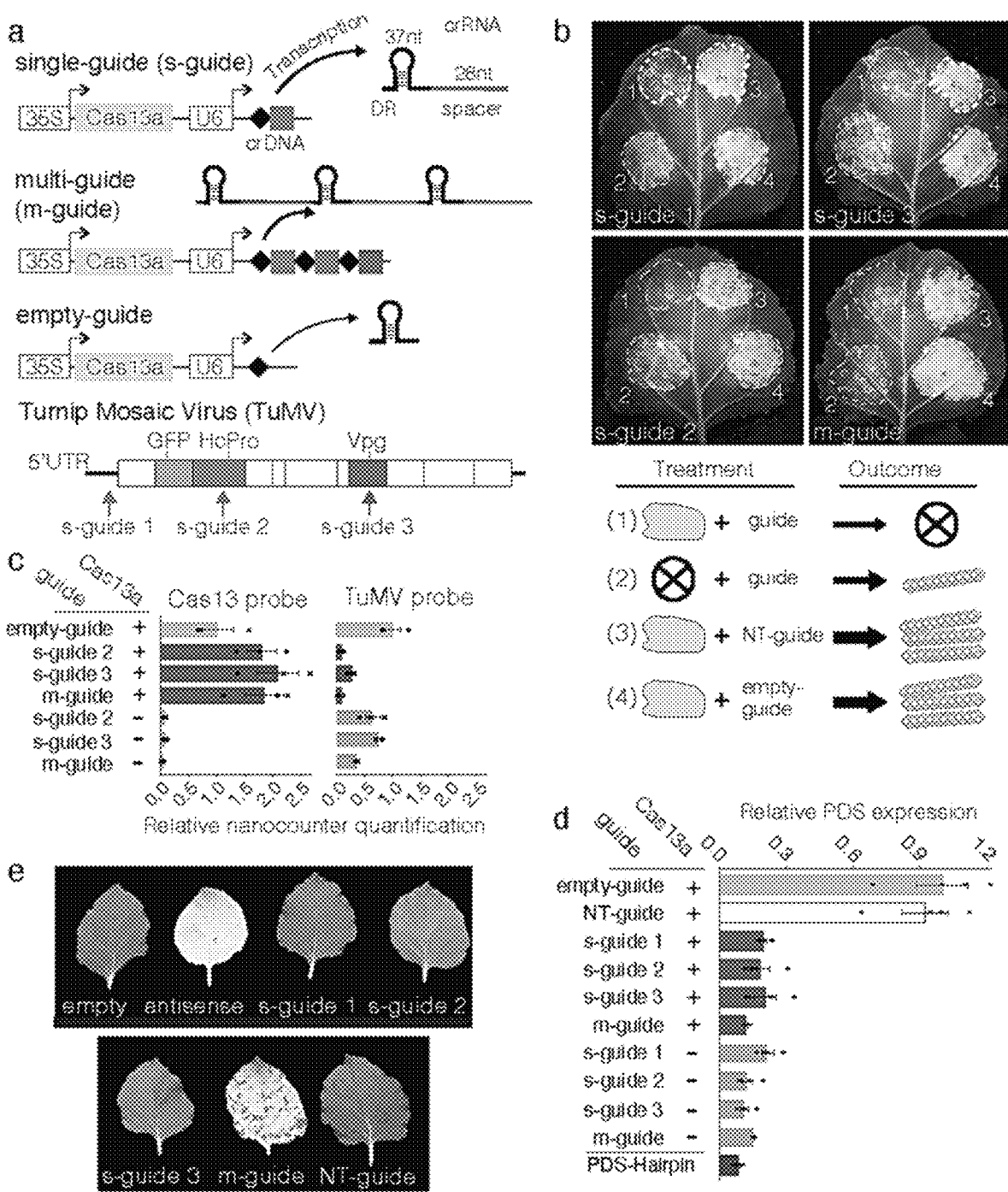
FIG. 2 shows data demonstrating that Cas13 and GIGS reduce viral and endogenous target RNA in *N. benthamiana*. a, Schematic overview of the Cas13 transgene system. Guide crRNA responsible for RNA target specificity contain a single 28 nucleotide (nt) spacer antisense to the target RNA (single-guide, s-guide), multiple 28 nt spacers (multi-guide, m-guide), or lack the spacer (empty-guide). A diagram showing the genome of turnip mosaic virus (TuMV) expressing GFP and indicating the location the three targeting sites for the guide crRNA. b, The accumulation of GFP accumulation was assessed at 120 hours post inoculation based on GFP fluorescence. Areas of agroinfiltration are shown in dashed white circles. Individual treatments are labeled with numbers and shown schematically below the photographs. c, Nanostring RNA quantification for Cas13 and TuMV levels corresponding to labeled treatments for *N. benthamiana* spot infiltration. Samples expressed Cas13 (+) or not (−). d, Quantitative PCR for the endogenous transcript PDS following *N. benthamiana* leaf spot infiltration. e, Representative single leaf images of *N. benthamiana* following TRV systemic delivery of guide crRNA targeting the PDS transcript. Empty and non-target guides (NT-guide) did not cause photobleaching (white sectors), while the antisense and multi-guide (m-guide) did induce visible photobleaching.

For TuMV targeting, three single crRNAs targeting different regions of TuMV namely 5' untranslated region (5' UTR), Helper component Proteinase (HcPro), viral genome linked protein (Vpg), and a poly crRNA containing aforementioned individual crRNAs in an array were designed and constructed (FIG. 2).

TABLE crRNA for targeting of TuMV

| Name of crRNA | Sequence of crRNA | Purpose | SEQ ID NO: |
|---|---|---|---|
| UTR-crRNA | GTTTCTGCCTTTGCCTCTTAC CTTTCGC | Targeting TuMV | 18 |
| HcPro-crRNA | CTGGGAAATCTTGTTGCGAAA GGACTTC | Targeting TuMV | 19 |
| Vpg-crRNA | TTGTGTTTGCTTTAATCGTTT TGTGTAT | Targeting TuMV | 20 |
| TuMV Array (Lba) | TAACGTTTCTGCCTTTGCCTC TTACCTTTCGCGCTGGAGAAG ATAGCCCAAGAAAGAGGGCAA TAACCTGGGAAATCTTGTTGC | Targeting TuMV | 21 |

TABLE-continued crRNA for targeting of TuMV

| Name of crRNA | Sequence of crRNA | Purpose | SEQ ID NO: |
|---|---|---|---|
| | GAAAGGACTTCGCTGGAGAAG ATAGCCCAAGAAAGAGGGCAA TAACTTGTGTTTGCTTTAATC GTTTTGTGTATTTTTTT | | |
| TuMV Array (Lbu) | AACAGTTTCTGCCTTTGCCTC TTACCTTTCGCGATTTAGACC ACCCCAAAAATGAAGGGGACT AAAACACTGGGAAATCTTGTT GCGAAAGGACTTCGATTTAGA CCACCCCAAAAATGAAGGGGA CTAAAACATTGTGTTTGCTTT AATCGTTTTGTGTATTTTTTT | Targeting TuMV | 22 |
| NS-crRNA | CCTTTCGGTACTTCGTCCACA AACACAA | Non-targeting | 23 |

Similar to TuMV, the PDS transcript was targeted using three single crRNAs namely, s-guide 1, s-guide 2, and s-guide 3 and a multi-guide crRNA containing the three single guides.

TABLE crRNA sequences for targeting of *Nicotiana benthamiana* PDS

| Name of crRNA | Sequence (5'-3') | Purpose | SEQ ID NO: |
|---|---|---|---|
| PDS-crRNA1 | GTCCAATTTGGGGCATTTTATTGAACAA | Targeting PDS | 24 |
| PDS-crRNA2 | TCGAAAGCTCGTCAGGGTTTATGAAGTT | Targeting PDS | 25 |
| PDS-crRNA3 | GAAGTAACTCGTAATCCTGTACAATAGC | Targeting PDS | 26 |
| NbPDS-Array1 | AACAGTCCAATTTGGGGCATTTTATTGAA CAAGATTTAGACCACCCCAAAAATGAAGG GGACTAAAACATCGAAAGCTCGTCAGGGT TTATGAAGTTGATTTAGACCACCCCAAAA TGAAGGGGACTAAAACAGAAGTAACTCGT AATCCTGTACAATAGCTTTTTTT | Targeting PDS | 27 |
| NbPDS-Array2 | AACACCTTTTGACTCAATATGTTCCACAAT CGGATTTAGACCACCCCAAAAATGAAGGG GACTAAAACAACAGACATGTCAGCGTACA CACTGAGCAGATTTAGACCACCCCAAAAA TGAAGGGGACTAAAACAGGGAAAAGCTT CGCTAGTTCCTTCATTGTTTTTTT | Targeting PDS | 28 |
| NS-crRNA | CCTTTCGGTACTTCGTCCACAAACACAA | Non-targeting | 29 |
| Multi-g1[mm5,6] | AACAGTCCgcTTTGGGGCATTTTATTGA ACAAGATTTAGACCACCCCAAAAATGA AGGGGACTAAAACATCGAgcGCTCGTC AGGGTTTATGAAGTTGATTTAGACCAC CCCAAAAATGAAGGGGACTAAAACAG AAGcgACTCGTAATCCTGTACAATAGCtttt | PDS-poly-crRNA with mismatches at 5 and 6 nucleotides | 30 |
| Multi-g1[mm10,11] | AACAGTCCAATTTtaGGCATTTTATTGAAC AAGATTTAGACCACCCCAAAAATGAAGGG GACTAAAACATCGAAAGCTatTCAGGGTTT ATGAAGTTGATTTAGACCACCCCAAAAAT GAAGGGGACTAAAACAGAAGTAACTtaTAA TCCTGTACAATAGCtttt | PDS-poly-crRNA with mismatches at 10 and 11 nucleotides | 31 |

TABLE-continued crRNA sequences for
targeting of *Nicotiana benthamiana* PDS

| Name of crRNA | Sequence (5'-3') | Purpose | SEQ ID NO: |
|---|---|---|---|
| multi-g1[mm21,22] | AACAGTCCAATTTGGGGCATTTTAgcGAACA AGATTTAGACCACCCCAAAAATGAAGGGGA CTAAAACATCGAAGCTCGTCAGGGTTTTcgG AAGTTGATTTAGACCACCCCAAAAATGAAGG GGACTAAAACAGAAGTAACTCGTAATCCTGT tgAATAGCtttt | PDS-poly-crRNA with mismatches at 21 and 22 nucleotides | 32 |
| NT-sgRNA | AACACCTTTCGGTACTTCGTCCACAAACACAA CGggaaccattcaaaacagcatagcaagtta aaataaggctagtccgttatcaacttgaaaa agtggcaccgagtcggtgctttt | Non-targeting | 33 |
| sgRNA1 | AACAGAAGTAACTCGTAATCCTGTACAATAG CCGggaaccattcaaaacagcatagcaagtta aaataaggctagtccgttatcaacttgaaaa agtggcaccgagtcggtgcTTTT | | 34 |
| SgRNA1 [50%mm] | AACAGTACTTAGTGGAATTGCAGAAGATTTG GCGggaaccattcaaaacagcatagcaagtta aaataaggctagtccgttatcaacttgaaa aagtggcaccgagtcggtgcTTTT | | 35 |

To create mismatch guides corresponding to PDS multi-guide crRNA, the nucleotide sequence was altered at positions 5-6 bp, 10-11 bp, and 21-22 bp from the 5' end of each crRNA. A non-targeting crRNA was designed as a negative control. To create the sgRNA1 construct, we assembled the single-guide 3 target sequence with the transactivating crRNA (tracrRNA). The same strategy was used to construct sgRNA1 [50% mm] in which single-guide 3 crRNA had mismatches at every-other nucleotide. The NT-sgRNA negative control contained the Cas9 tracrRNA sequence and a non-plant target sequence.

TABLE crRNA sequences for targeting of tomato PDS

| Name of crRNA | Sequence (5'-3') | Purpose | SEQ ID NO: |
|---|---|---|---|
| SIPDS-Array | AACATAAGCTGAACTACCTTGGACTTTargeting CTCAAGTGATTTAGACCACCCCAAAtomato AATGAAGGGGACTAAAACATTGAA PDS AGTTCGTCAGGGTTTATAAAGTTGA TTTAGACACCCCAAAAATGAAGGGG ACTAAAACACAAGTAACTCATAATC CTGTACAATAGCTTTT | Targeting tomato PDS | 36 |
| NS-crRNA | CCTTTCGGTACTTCGTCCACAAACANon-CAA | Non-targeting control | 37 |

Cloning of CRISPR-Cas13a Machinery

A backbone harboring AtU6 promoter sequence with one Lbu or Lba specific direct repeat sequence and BsaI Golden Gate site was custom synthesized (IDT, Coralville, IA) for expressing crRNAs. This backbone was cloned into entry vector pENTR (Thermo Scientific, Waltham MA) using Topo cloning. Spacer sequences were ordered as oligos and cloned using BsaI Golden Gate site. Gateway assembly (Invitrogen) was used to clone the promoter and crRNA cassette into the destination vector pGWB413 containing or lacking Cas13a effector.

Cloning crRNA for TRV Systemic Delivery

For systemic expression of crRNA using TRV, pea early browning virus (PEBV) promoter sequence with LbuCas13a specific direct repeat and BsaI Golden gate site were custom synthesized (IDT, Coralville, IA) and cloned into Gateway entry vector PCR8. Three single guide and multi-guide crRNA sequences targeting NbPDS, and a multi-guide crRNA targeting SIPDS were ordered as oligos and cloned using Golden gate assembly. The cassette harboring PEBV promoter and TuMV, NbPDS, or SIPDS targeting crRNAs was PCR amplified with primers having EcoRI and MluI restriction sites and cloned into EcoRI and MluI digested pTRV2 vector.

TABLE

Sequences used in study

| Oligo name | Sequence (5'-3') | Purpose | SEQ ID NO: |
|---|---|---|---|
| PDS3for | GGACTGGATGAGAAAGCA AGGTGT | qRT-PCR of PDS | 38 |
| PDS3rev | ATCGAAAGCTCGTCAGGG TTTATG | qRT-PCR of PDS | 39 |
| EF1a-FP | AGCTTTACCTCCCAAGTC ATC | qRT-PCR of EF1a | 40 |
| EF1a-RP | AGAACGCCTGTCAATCTT GG | qRT-PCR of EF1a | 41 |
| qPCR-CP-FP | GAAGGAGAAGAAGGAGAG AGAGA | qRT-PCR of TuMV-CP | 42 |
| qPCR-CP-RP | CAGAGGTTCCAGCGTTTA CTT | qRT-PCR of TuMV-CP | 43 |
| qPCR-P1-FP | TGAGGACGAGAAGGTTGT AATG | qRT-PCR of TuMV-P1 | 44 |

TABLE-continued

Sequences used in study

| Oligo name | Sequence (5'-3') | Purpose | SEQ ID NO: |
|---|---|---|---|
| qPCR-P1-RP | ATTGGTTGCTGCGCTCTA | qRT-PCR of TuMV-P1 | 45 |
| AtEF1α FP | CCGAACAAGGAACAAGTGAAAG | qRT-PCR of EF1α | 46 |
| AtEF1α RP | GTCCTCATCTTCAATGCCAGTA | qRT-PCR of EF1α | 47 |
| AtTTG1 qPCR FP | CGCCTCAGAGCTGTAAACATA | qRT-PCR of TTG1 | 48 |
| AtTTG1 qPCR RP | CTCCGAACCAGCCGAATAAA | qRT-PCR of TTG1 | 49 |
| PDS-Probe-FP | GGTCACAAACCGATATTGCTGGAGG | PDS northern | 50 |
| PDS-Probe-RP | ACAGACATGTCAGCGTACACACTGAGCA | PDS northern | 51 |
| Lbu-Probe-FP | GCTGAAAATATTTAGGCAGTTGAACTC | Lbu northern | 52 |
| Lbu-Probe-RP | GGAACCCTTTAAGTTCGTCAGCT | Lbu northern | 53 |
| LbuCas13a FP | GTTCGGGATTATGCGAAAGTGACC | Lbu RT-PCR in Arabidopsis | 54 |
| LbuCas13a RP | ACGGAAAACCTCCAGTTCCTCGC | Lbu RT-PCR in Arabidopsis | 55 |
| MluI-PCR8-RP | GACTAGCGAATTCAATTCGAGCATCTTGTTCTGG | Amplification of PEBV-crRNA Cassette | 56 |
| EcoRI-PEBV-FP | CAGTACAACGCGTCTGGGTCGAATTCGCC | Amplification of PEBV-crRNA Cassette | 57 |

Cloning of Intron Hairpin RNAi (hpRNAi) Cassette

For cloning of PDS hpRNAi construct, a 197 bp sequence of PDS gene was custom synthesized as sense and antisense arm along with PDK intron sequence with 25 bp overhang complementarity to pGWB413 vector. All the fragments were assembled using HiFi DNA assembly (New England Biolabs, Ipswich, MA) expressed by the 35S promoter.

Agro-Infiltration of *N. benthamiana* and *Solanum lycopersicum*

*N. benthamiana* plants were grown and maintained in growth chamber at 23° C. with 16-hour day and 8 hour light cycle and 70% humidity. Four week old plants were used for leaf spot agroinfiltration to test Cas13a interference against TuMV-GFP. Binary constructs harboring Cas13a homologs with or without crRNA (targeting TuMV or PDS transcript), TuMV-GFP infectious clone (a gift from Dr. James Carrington) were individually transformed into chemically competent *Agrobacterium tumefaciens* strain GV3101. Single colonies for each construct were inoculated into LB medium with antibiotics and grown overnight at 28° C. Next day, the cultures were centrifuged and suspended in agroinfiltration buffer (10 mM MgCl2, 10 mM MES buffer pH 5.7 and 100 µM acetosyringone), and incubated at ambient temperature for 2-3 hours. For TuMV interference assay, *Agrobacterium* cells harboring Cas13a with crRNA targeting TuMV were infiltrated at an OD600 of 1.0 into adaxial side of four week old *N. benthamiana* leaves using a 1.0 ml needleless syringe. Two days later, *Agrobacterium* cells harboring TuMV-GFP were infiltrated into same areas at an OD600 of 0.3. After five days, interference activity of Cas13a against the TuMV-GFP was assayed by visualizing GFP in infiltrated leaves under UV light using a hand-held UV lamp (Fisher Scientific, Waltham, MA) and a Nikon camera.

For PDS silencing, leaves of four-week-old *N. benthamiana* plants were infiltrated with *Agrobacterium* cultures harboring LbuCas13a with crRNAs targeting PDS and leaf samples were collected at 5 days post inoculation. For TRV mediated crRNA delivery, assays used three-week-old *N. benthamiana* plants. A single colony of *Agrobacterium* harboring crRNAs targeting PDS were inoculated into LB medium with antibiotics and grown overnight at 28° C. Next day, the cultures were centrifuged and resuspended into infiltration buffer at an OD600 of 0.6. The cultures were incubated at ambient temperature for 2-3 hours and infiltrated into *N. benthamiana*. Infiltration of tomato plants was performed similarly to *N. benthamiana* except that *Agrobacterium* cells were resuspended into infiltration buffer at an OD600 Of 2.0. The cultures were incubated at ambient temperature for 2-3 hours and infiltrated into three-week-old tomato plants.

RNA Isolation, cDNA Synthesis, qRT-PCR and Northern Blotting

Total RNA was isolated from Agro-infiltrated leaf samples using Trizol (Ambion) method. For first strand cDNA synthesis, DNase treated 1.0 ug total RNA was reverse transcribed using either random hexamers or oligo (dT20) and SuperScript II reverse transcriptase (Thermo Fisher Scientific) according to the manufacturer's instructions. Quantitative PCR was performed using SYBR Select Master Mix (Applied Biosystem) and gene specific primers for PDS and TuMV. EF1α gene was used as internal house-keeping reference for PDS and TuMV qRT-PCR The experiments were repeated three times with three biological and two technical replicates. Relative expression values were plotted using ggplot2 in R. For detection of PDS transcript, 20 µg of total RNA was separated on a denaturing 1.2% agarose gel and blotted on a Hybond-N+(Roche) membrane. RNA was crosslinked using UV light and hybridized with a DIG labelled probe (PCR DIG probe synthesis kit, Sigma). For detection of LbuCas13a the membrane was stripped and probed with DIG labelled Cas13a specific probe and signals detected on a Licor Odyssey imaging system (LI-COR Bioscience, Lincoln, NE).

Real Time Quantification of PDS and TuMV Transcripts Using Nanocounting Technology For direct RNA quantification of PDS and TuMV transcripts using NanoString technology, we collected sequence data for different *N. benthamiana* genes including PDS, three house-keeping genes for normalization (PP2aa2, EF1α, RPL23a), LbuCas13a, HCPro and coat protein.

TABLE

Probes for Nanocounting

| Probe name | (5'-3') | SEQ ID NO: | Purpose |
|---|---|---|---|
| Tumv-CP A | CGTGTATAGGATTAGATGATCGAGGTTTAGA GCCACTCTTTTCTCGTATCCAACAGCCACTTT TTTTCCAAATTTTGCAAGAGCC | 58 | For TuMV quanti- fication |
| B | CGAAAGCCATGACCTCCGATCACTCCGCGTT GAACGTGTGTTGGATAGATCCGTCTGCTCCG G | 59 | |
| Tumv-HCpro A | CGAAAGGACTTCAGTGAACCCTTCTCAATGT TCTCGGTTCTGTTCTTCAGCACCGTGTGGACG GCAACTCAGAGATAACGCATAT | 60 | For TuMV quanti- fication |
| B | CGAAAGCCATGACCTCCGATCACTCTGTCAC ACATTAGTGTTGGGTTGATGTGCGCTTTCTGG GAAATCTTGTTG | 61 | |
| LbuCas13a A | CGCAGTTACGCACATAGGTGTCCAGCTTGTTT AACAGCTTATTTTCGATACATCCTCTTCTTTT CTTGGTGTTGAGAAGATGCTC | 62 | For LbuCas13a quanti- fication |
| B | CGAAAGCCATGACCTCCGATCACTCGAAGTC TGAAGTGGCTATCTCCCCGTCTTGCAAATAAT AGTTGTACTTGC | 63 | |
| NbPDS A | TTGGGTAAGCCCCAAAGAATATGTGCAACCC AGTCTCGTACCAATCTCCACAAAGACGCCTA TCTTCCAGTTTGATCGGGAAACT | 64 | For PDS quanti- fication |
| B | CGAAAGCCATGACCTCCGATCACTCCCACTG CAACCGATCGTTAATCCCTAGTTCTCCAAAC AGGTTCTGCATAT | 65 | |
| NbEIF1a A | CAGGGACGGTTCCAATGCCACCAATCTTGTA AACATCCTGAAGTGGAAGACCAATTTGGTTT TACTCCCCTCGATTATGCGGAGT | 66 | Internal control |
| B | CGAAAGCCATGACCTCCGATCACTCACCAGG CTTGAGCACACCAGTCTCCACACGACCAA | 67 | |
| NbRPL23A A | TCCCATCAGGCCTAATCAAGGTATTGACTTTC TTTGTCTGGATGCGAACCTAACTCCTCGCTAC ATTCCTATTGTTTTC | 68 | Internal control |
| B | CGAAAGCCATGACCTCCGATCACTCAACGTC CAATGCATCGTAGTCAGGAGTCAACCTCACA TATGCTTTCTTCG | 69 | |
| NbPP2aa2 A | CTTGCCAAGTGCAGCACAACCCTCAACAGCT AATAAACGTACAGAATCCTCAGATAAGGTTG TTATTGTGGAGGATGTTACTACA | 70 | Internal control |
| B | CGAAAGCCATGACCTCCGATCACTCTTGACA ATGACAGGCAGGATGTGTGCAACACAATCCT GTGGCTCCAACAG | 71 | |

The sequence information was utilized to design two probes for each target gene. Total RNA samples (300 ng total RNA) and probe master mix were supplied to the Huntsman Cancer Institute, University of Utah for Nanostring quantification following manufacturer specifications. The nanocounting data was analyzed using the nSolver software.

Western Blotting

For western blotting, total protein was isolated from *Agrobacterium* infiltrated leaves using extraction buffer (50 mM Tris-Cl, 1% β-Mercaptoethanol and protease inhibitor cocktail (Roche, Basel, Switzerland)). Total proteins were boiled with loading buffer (100 mM Tris-Cl, 20% Glycerol, 4% SDS, 10% β-Mercaptoethanol and 0.2 mg/ml bromophenol blue) and resolved on 12% SDS-PAGE gel. The proteins were transferred from SDS-PAGE gel to PVDF membrane (GE healthcare, Chicago, IL). Membrane blocking and antibody incubations were performed using iBind western device (Thermo Fisher Scientific, Waltham, MA) according to the instrument manual. Finally, the membrane was treated with ECL Select western blotting detection reagent (GE healthcare, Chicago, IL) and signal was detected with Licor Odyssey imaging system (LI-COR Bioscience, Lincoln, NE).

Generating Stable Transgenic *Arabidopsis* Plants

TTG1-targeting three single guides (guide-1, -2, -3) and a multi-guide crRNA, and non-targeting (NT) oligos were annealed and ligated into pENTR backbone containing BsaI Golden gate site.

TABLE crRNA sequences for targeting TTG1

| Name of crRNA | Sequence (5'-3') | Purpose | SEQ ID NO: |
|---|---|---|---|
| AtTTG1 s- guide 1 | TAACGAATCTGGAGCTGAATTATC CATG | Targeting TTG1 | 72 |
| AtTTG1 s- guide 2 | CTACAAGTTCCGAGACGTTTCGGC TCTA | Targeting TTG1 | 73 |

TABLE-continued crRNA sequences for targeting TTG1

| Name of crRNA | Sequence (5'-3') | Purpose | SEQ ID NO: |
|---|---|---|---|
| AtTTG1 s-guide 1 | AGGAGCTGCATTTTGTTAGCAAAAGCAA | Targeting TTG1 | 74 |
| TTG1 m-guide | AACATAACGAATCTGGAGCTGAATTATCCATGGATTTAGACCACCCCAAAAATGAAGGGGACTAAAACACTACAAGTTCCGAGACGTTTCGGCTCTAGATTTAGACCACCCCAAAAATGAAGGGGACTAAAACAAGGAGCTGCATTTTGTTAGCAAAAGCAATTTT | Targeting TTG1 | 75 |
| TuMV m-guide | AACAGTTTCTGCCTTTGCCTCTTACCTTTCGCGATTTAGACCACCCCAAAAATGAAGGGGACTAAAACACTGGGAAATCTTGTTGCGAAAGGACTTCGATTTAGACCACCCCAAAAATGAAGGGGACTAAAACATTGTGTTTGCTTTAATCGTTTTGTGTATTTTTTT | Non-targeting control | 76 |

Gateway assembly was used to transfer guide crRNA to pGWB413 destination vector with or without 3×HA-LbuCas13a. Stable transgenic *Arabidopsis* plants expressing TTG1 guides with or without LbuCas13a were generated using *Agrobacterium*-mediated floral dip. Similarly, stable *Arabidopsis* controls with a NT crRNA, a 197 bp hairpin construct against TTG1 (a gift from Dr. Steven Strauss), and no guide transformation control (only 3×FLAG-LbuCas13a) were generated. One month after floral dip, $T_1$ seeds were collected and stored at 4° C.

*Arabidopsis* Phenotyping

Transformed $T_1$ *Arabidopsis* seedlings were identified using rapid selection protocol. Selection was conducted on ½ MS media with a Kanamycin concentration of 100 μg/ml. Positive transformants (n=36) for each TTG1 crRNA with or without LbuCas13a and TTG1 hairpin controls were transferred to soil and grown under optimal conditions. Control *Arabidopsis* Col-0 plants were germinated on ½ MS media without Kanamycin and transferred to soil. Seventh leaf from ten individual plants for each construct was imaged under a dissecting microscope equipped with a Nikon camera and trichomes were counted using multi-point feature in ImageJ software. For each construct, RNA was extracted from $10^{th}$ leaf of five individual plants with varying leaf trichomes to quantify TTG1 expression using qRT-PCR. AtEF1α was used as internal house-keeping control for normalizing TTG1 expression. Selected individual plants for each construct were self-pollinated to collect $T_2$ seed. Five technical replicates of each selected plant/line were used for analyzing total flavonoids, in 5 mg seed, using modified aluminum chloride ($AlCl_3$) colorimetric method. Flavonoids content was estimated using the following formula: flavonoids (mg/g)=concentration obtained through quercetin calibration curve×(volume of extract/seed weight).

To determine the inheritance of GIGS and Cas13-mediated gene silencing, 10 $T_2$ plants from selected $T_1$ lines were transferred to soil after Kanamycin selection. Seventh leaf from 10 individual $T_2$ plants was imaged for counting leaf trichomes. Statistical comparisons between the transformation control (no guide) and each selected line was performed. TTG1 expression in the top rosette leaf from three individual $T_2$ plants was analyzed using qRT-PCR. Five individual $T_2$ plants for each line were self-pollinated to collect $T_3$ seed. Total flavonoid content was analyzed in $T_3$ seeds from five independent seed lots (five biological replicates). Similarly, proanthocyanidins content was measured using DMACA-HCl method from three seed lots. Proanthocyanidins were measured at 640 nm and reported as per gram of seed weight. Total flavonoid and proanthocyanidin analyses were repeated twice, the averaged values for each seed lot were used for statistical comparisons. Absorbance of flavonoids and anthocyanin was measured using Thermo Spectronic 3 UV-Visible Spectrophotometer. While absorbance of proanthocyanidins was measured through Synergy H1 Hybrid Multi-Mode Microplate Reader (Agilent Technologies, Winooski, Vermont).

For leaf anthocyanin quantification, one-week-old $T_3$ seedlings after Kanamycin selection were transferred into ½ MS media+3% sucrose and subjected to light stress (500 μmol m$^{-2}$ s$^{-1}$) for one week. 200 mg of leaf tissue was used for quantifying anthocyanin. Anthocyanin analysis was repeated twice with 5 replicates in each batch. Anthocyanin content was calculated by using following formula (absorbance/35,000×dilution factor×647×1,000 per mg of sample extracted (in mg g−1 fresh weight). Representative plantlets following sucrose treatment showing anthocyanin pigmentation were imaged with a dissecting microscope equipped with a Nikon camera. To test TTG1 expression in $T_3$ generation, seventh leaf from three individual plants was analyzed using qRT-PCR. To determine the expression of LbuCas13a, RT-PCR was conducted on cDNA synthesized for qRT-PCR. Western blot analysis with HA-tag antibody was conducted on one-week-old $T_3$ seedlings post Kanamycin selection.

Example 2

High-Fidelity RNA Silencing Though Improved Design for Short Multiple Repeat Fragment Silencing In our previous CRISPR-Cas13 experiments evaluating their ability for TuMV (Tobacco mosaic virus) interference, we observed strong TuMV interference with guide crRNA alone in the absence of LbuCas13a protein. We determined that multi-guide crRNA (short multiple repeat fragments), that targeted three mRNA regions of a single gene, produced stronger silencing compared to a single-guide crRNA. In addition to virus interference, systemic TRV (tobacco rattle virus) expression of guide crRNA against endogenous phytoene desaturase (PDS) gene reduced PDS expression and elicited leaf photobleaching in *Nicotiana benthamiana* and *Solanum lycopersicum*. In addition to transient assays, stable transgenic *Arabidopsis* plants expressing guide crRNA against TTG1 (TRANSPARENT TESTA GLABRA1) RNA resulted in lower TTG1 expression, seedling anthocyanin, grain tannins, and fewer leaf trichomes, demonstrating heritability of the silencing approach. Expressing these SMRRT silencing constructs in a tissue- or age-specific manner offers a potential cis-genic solution to bypass antagonistic pleiotropy in plants.

In the preliminary work, the phenotype reduction elicited by the SMRRT silencing constructs was weaker compared to a conventional TTG1-haripin (RNAi) construct. To utilize SMRRT silencing technology in transcriptome engineering, SMRRT silencing constructs need to be optimized to elicit a phenotype reduction levels similar as RNAi. However, limited knowledge exists on guide crRNA design parameters, such as optimal guide length, number of crRNA in a multi-guide construct, crRNA order, and crRNA copy number for effective GIGS. To improve our understanding of SMRRT guide design parameters, we evaluated different guide design parameters using Tobacco rattle virus (TRV)

systemic infection in *N. benthamiana*. Our results shed like on optimized crRNA length, sequence flexibility for crRNA design, crRNA copy number, and crRNA dosage that could potentially improve SMRRT silencing technology.

This prior work is extended, improving SMRRT silencing by altering crRNA length, number, and structure for use of the constructs in gene silencing in in plants. The improved construct design for the SMRFs, a cis-genic RNA silencing approach, elicited stronger gene silencing with reduced off-targeting effects.

As limited knowledge exists on crRNA guide design parameters to apply these new silencing constructs for crop improvement, we tested different guide design parameters by systemically expressing PDS guide crRNA through agro-mediated Tobacco rattle virus (TRV) infection of *Nicotiana benthamiana*. Systemic movement of PDS multi-guide for RNA silencing revealed a minimum guide length requirement of 22 nt for SMRRT silencing induction and no additional sequence at the 5' crRNA region. Interestingly, increasing the number of crRNA fragments in a multi-guide from three to six crRNA fragments against PDS mRNA elicited photobleaching patterns observed with the control antisense PDS construct. In addition to testing a six multi-guide construct against PDS mRNA, increasing guide dosage of single crRNA fragments by expressing three or six copies of the same crRNA sequence elicited an increased PDS silencing with an additional guide dosage.

Results

Multi-Guide crRNA Fragments do not Need to be Assembled as a Single RNA Molecule for SMRRT Silencing Our previous research demonstrated that multi-guide crRNA fragments resulted in more viral and endogenous RNA reduction compared to silencing elicited by a single guide. One interpretation is that the more locations an RNA is targeted the greater the RNA degradation. This could be achieved by more DCL-based mRNA-crRNA processing and the generation of more siRNA. An alternate hypothesis however, is that multi-guide crRNA change the targeted RNA's physical conformation upon crRNA-mRNA hybridization that results in target RNA decay. This could be achieved if the crRNA-mRNA duplex was detected as an aberrant RNA structure and triggered non-sense mediated decay (NMD) or possibly de-adenylation or de-capping.

To understand which of these mechanisms explains SMRRT silencing, we modified the structure of our previously tested multi-guide crRNA targeting PDS. Here, the multi-guide crRNA containing three separate crRNA fragments was expressed as a single RNA molecule targeting different mRNA locations (FIG. 17*a*) and driven by a single promoter. To modify this, we split the crRNA guides into three separate RNA molecules driven by individual promoters (FIG. 17*a*) in order to test if simultaneous expression of three separately expressed crRNA fragments caused similar target RNA reduction as a multi-fragment crRNA molecule (containing all 3 fragments).

We developed the following nomenclature to refer to the different constructs: m3g3 where 3 defines how many guides (crRNA fragments) are contained in a single RNA molecule, and 3 represents how many different crRNA sequences are present on that RNA molecule. For instance, a multi-guide crRNA with three guides targeting three different sequences is termed m3g3. We expressed either PDS m3g3 or three separate single-guide (s-g) crRNA corresponding to these same PDS sequences in *N. benthamiana* using agro-mediated TRV infection (FIG. 17*b*).

Two-weeks after infection, we observed similar visible photobleaching in systemic tissue elicited by PDS m3g3 or the simultaneous expression of the three PDS s-guide crRNA (FIG. 17*c*). The non-target (NT)-guide control produced no visible photobleaching as expected (FIG. 17*c*). Supporting the visible photobleaching, chlorophyll content was significantly reduced ~60% with either PDS m3g3 or three PDS s-guides compared to the NT-guide crRNA (FIG. 17*d*). Quantifying PDS transcript levels in photobleached tissue using qPCR showed a significant ~50% reduction in PDS mRNA levels from either PDS m3g3 or three PDS s-guides compared to the NT-guide crRNA (FIG. 17*e*). These results show that three different crRNA fragments targeting different regions of PDS produced significant transcript reduction, regardless if they were expressed as a single crRNA molecule (i.e. multi-guide) or as three separate single guide crRNAs. These results were unexpected and were contrary to our hypothesis that SMRRT silencing involves target RNA conformational change brought about by multiple binding events of a single multi-guide crRNA construct.

Minimum crRNA Length of 22 nt is Required for Silencing of PDS Target

This new technology relies on short crRNA fragments. We sought to understand the thresholds for fragment length. In *N. benthamiana*, the shortest nucleic acid homology of 23 nt against green fluorescent protein (GFP) was shown to silence GFP RNA and a minimum length of 33 nt against PDS to elicit a visible photobleaching phenotype. In our previous experiments, we observed a complementary nucleic acid sequence of 28 nt initiated SMRRT silencing of PDS RNA for eliciting a photobleaching response in *N. benthamiana* and *S. lycopersicum*. However, the minimum guide crRNA length requirement for induction of SMRRT silencing has not been determined. Based on the hypothesis that SMRRT silencing utilizes plant RNAi pathway for altering targeted gene expression, we predicted that short guide crRNA length (<21 nt) is required for initiation of SMRRT silencing by triggering AGO-mediated dsRNA cleavage.

Figure 18:
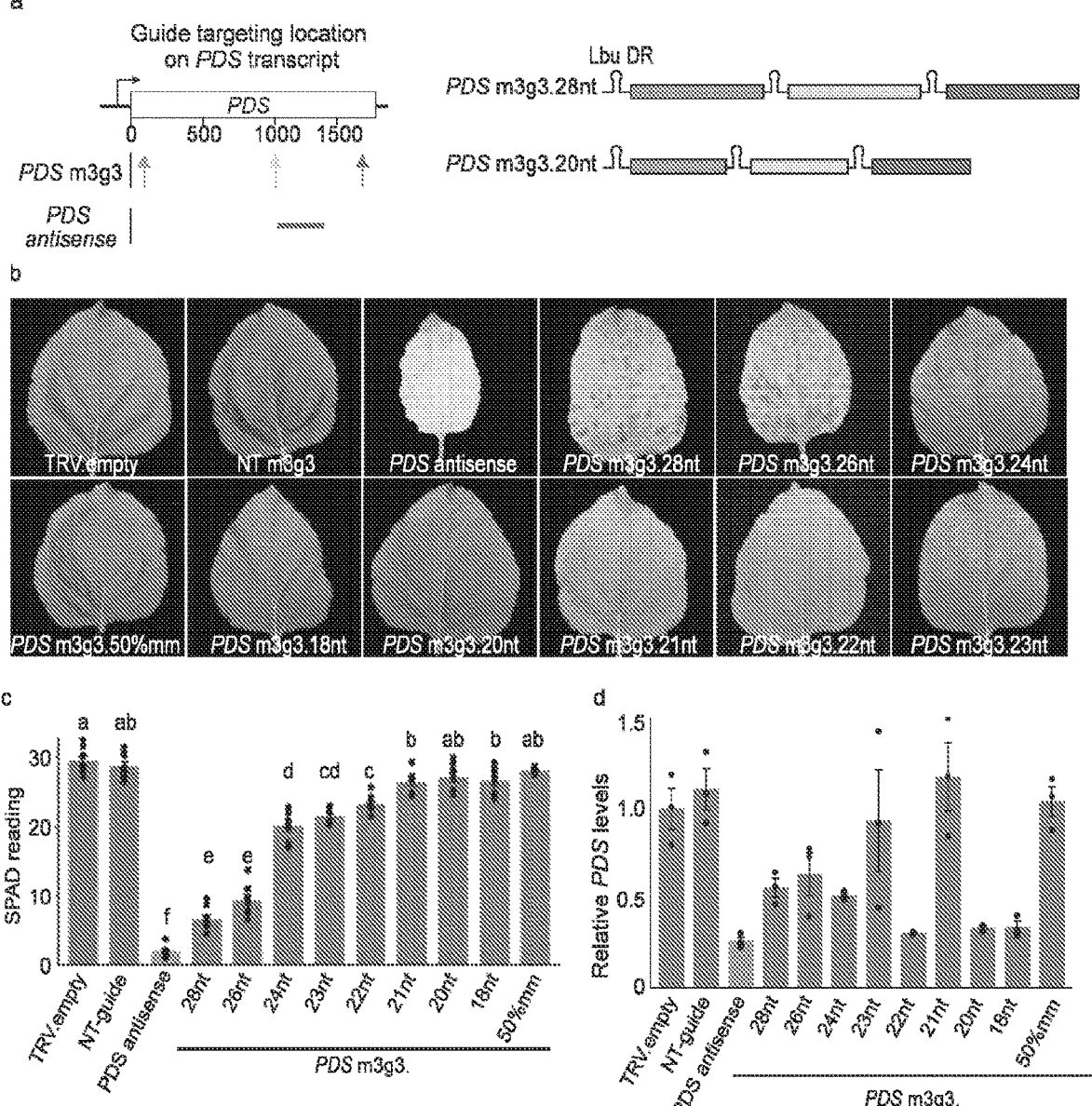
FIG. 18 shows data evaluating minimum multi-guide crRNA length required for GIGS. a, Schematic representation of PDS guide crRNA and antisense PDS construct targeting locations on PDS transcript. Schematic of PDS m3g3.28nt crRNA with 37 bp LbuCas13a direct repeat (LbuDR) and three 28 bp crRNA. PDS m3g3 with varying lengths were generated by reduced crRNA length from the 3' end of each crRNA. For example, PDS m3g3.20nt was generated by removing 8 nt from the 3' end of each crRNA.

To determine the minimum crRNA length required for induction of GIGS, we evaluated varying lengths, from 18 to 28 nt, for a PDS m3g3 crRNA construct, including an Lbu DR (FIG. 18*a*). Following systemic TRV movement, SMRRT silencing elicited by PDS m3g3.28nt crRNA showed a photobleaching appearance in lower leaves. The photobleaching phenotype for PDS m3g3.26nt was similar to that of PDS m3g3.28nt (FIG. 18*b*). Moderate photobleaching was visible around leaf veins in the lower leaves with decreasing visibility for PDS m3g3.24nt, 0.22nt, and 0.23nt crRNA. No visible photobleaching was observed with PDS m3g3.21nt, 20nt, 0.18nt, 50% mismatching (50% mm) crRNA, TRV*empty*, or NT m3g3 treatments (FIG. 18*b*). TRV expressing an antisense PDS construct (RNAi) elicited complete photobleaching in the lower leaves. Measuring chlorophyll content via SPAD meter showed 70-80% chlorophyll reduction with PDS m3g3.28nt and 0.26nt, 20-30% reduction with PDS m3g3.24nt, 23nt, and 0.22nt (FIG. 18*d*). No chlorophyll reduction was seen with PDS m3g3.21nt, 0.20nt, 0.18nt, and 0.50% mm compared to TRV*empty* control. We observed the largest chlorophyll reduction (93%) with antisense PDS. Collectively, these results indicate that a minimum crRNA length for this construct was 22 nt to see chlorophyll reduction. Moreover, the fragment length was directly correlated to the strength of the reduction observed.

Multi-Guide crRNA do not Require Direct Repeat or Other Specific Sequence Arrangement for Silencing The traditional CRISPR-Cas13 mediated RNA-targeting system processes precursor crRNA (pre-crRNA) transcripts into mature crRNAs by cleaving before the DR stem region. As SMRRT silencing is independent of a Cas13 protein, there is no specific constraint that "guide sequences" for SMRRT silencing possess the DR sequence, other than the possibility that it could be required to elicit SMRRT silencing. One hypothesis is that the DR stem-loop mediates DCL processing of crRNA multi-guides, thereby releasing the individual guide sequences to somehow associate with AGO. Another hypothesis is that complementary binding of crRNA-mRNA alone triggers SMRRT silencing, and intervening sequences between the guides does not impact the phenomena.

To test these hypotheses and determine if the Cas13a DR sequence, or the resulting stem-loop structure are required for the induction of SMRRT silencing, we tested modified PDS m3g3 construct designs (FIG. 19a). We evaluated four PDS m3g3 construct designs where the 5' guide sequence was varied (FIG. 19a). Expressing the modified fragments using TRV delivery in *N. benthamiana*, we found that the intervening 5' sequence for PDS m3g3 did not affect visible photobleaching (FIG. 19b). That is, replacing the crRNA DR with either an *Arabidopsis* miR170 stem-loop, an *Arabidopsis* miR170 lacking 4 nt stem (i.e., loop only), a random 20 nt sequence, or no DR all (directly connected) elicited a clearly visible photobleaching phenotype (FIG. 19b). Each of these modified constructs were also tested with a non-target (NT)-guide control, and no design elicited photobleaching alone (FIG. 19b). Chlorophyll content in plants expressing PDS m3g3 LbuDR, stem-loop, loop, random, and no DR was reduced by 65-80%, compared to the TRV$_{empty}$ control, and no significant reduction was observed for the guide design controls expressing the NT m3g3 crRNA (FIG. 19c). The visible photobleaching pattern was supported by PCR transcript quantification, where we observed 35% to 50% reduced PDS transcript levels compared to the TRV$_{empty}$ control (FIG. 19d). Together, these results show m3g3 5' guide sequence does not require a DR or any specific sequence for GIGS initiation.

Figure 17:
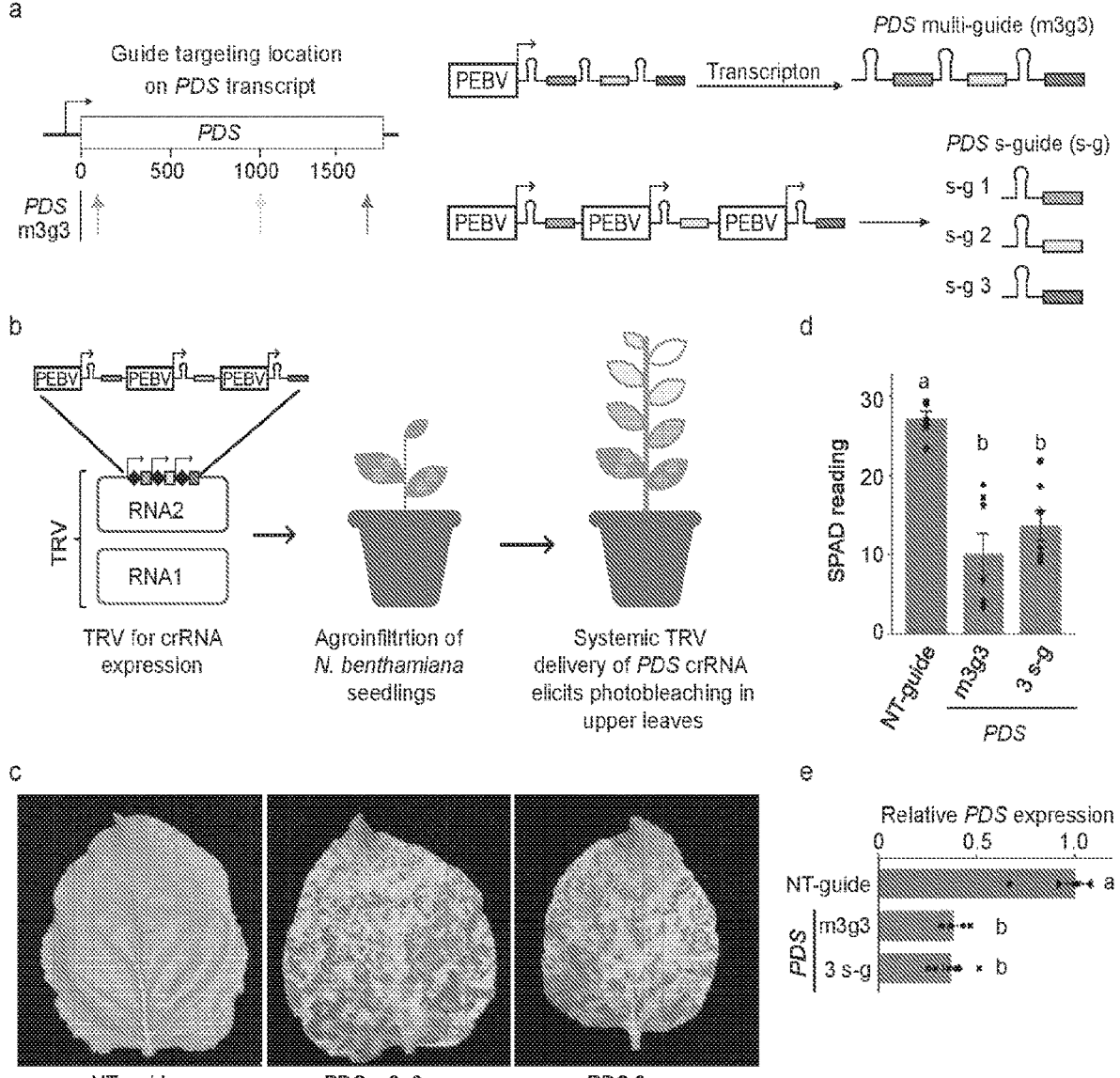
FIG. 17 shows data demonstrating that PDS multi-guide crRNA expressed with three promoters produced strong GIGS. a, Schematic of PDS guide crRNA targeting locations on PDS transcript. PDS multi-guide crRNA was expressed as a single RNA molecule using a single PEBV promotor, and three separate s-guides using three PEBV promotors. b, Two-component Tobacco rattle virus (TRV) system for systemically expressing crRNA through agro-mediated TRV infection, and evaluating targeted gene silencing phenotype after systemic TRV infection. c, Representative images of a lower leaf from *N. benthamiana* plants after two-weeks of TRV systemic delivery with PDS m3g3 and three s-guides. d, Chlorophyll content measured with SPAD meter two-weeks after systemic delivery of crRNA. e, Relative PDS expression, quantified using qRT-PCR, compared between NT-guide and each treatment. Statistical comparisons were made using one-way ANOVA in R, multiple comparisons of treatments by means of Tukey were performed using HSD.test function from the agricolae R package. Treatments with the same letter are not significantly different.

Guide Order of crRNA in PDS Multi-Guide Construct Did not Alter Silencing Strength PDS m3g3 expressed as a single RNA molecule elicited a visible photobleaching response (FIG. 17). When a m3g3 crRNA is expressed as single RNA molecule, it is hypothesized that all three crRNA could hybridize with the targeted mRNA to change its confirmation or only one crRNA hybridizes with RNA while the other two adjacent crRNA in the m3g3 remain unattached. Given our limited knowledge on how many crRNA in a multi-guide hybridizes with RNA or in which order they hybridize with the target RNA, we tested if the guide order in a multi-guide crRNA influences RNA silencing activity. We hypothesized that guide order of individual crRNAs in the m3g3 crRNA does not affect DCL-processing activity. We evaluated six TRV infectious clones generated by rearranging three PDS m3g3 crRNA in six different combinations based on their position in the multi-guide (FIG. 20a). Five of the six crRNA treatments elicited a similar mosaic photobleaching pattern in the lower leaves, and one crRNA construct elicited only a partial photobleaching (FIG. 20b). No photobleaching was observed in plants infected with the TRV$_{empty}$ control. Consistent with the visible photobleaching patterns, we observed similar levels of chlorophyll reduction with five of the six rearranged PDS guide crRNA constructs, and only slightly less for the sixth construct (FIG. 20c).

Increasing crRNA Fragment Number in a Multi-Guide Produced Stronger Photobleaching Previous research identified antisense fragments in the range of ~200 to ~1300 nt silenced RNA more effectively than short inserts (for RNAi). Supporting these findings, the visible photobleaching phenotype elicited by a 397 nt antisense PDS fragment was completely white with almost no chlorophyll in the lower leaves (FIG. 18b, 19c, and FIG. 23). In contrast, PDS m3g3 crRNA elicited a visible photobleaching phenotype in the lower leaves that was more mosaic, less white, and leads to a lesser reduction in chlorophyll content (FIG. 18c). In the newly emerged leaves, antisense PDS caused complete photobleaching while PDS m3g3 elicited no visible photobleaching phenotype (FIG. 23). One possibility for lesser reduction in chlorophyll content with PDS m3g3 could be attributed to differences in the length of the RNA targeted by the crRNA fragments and the and antisense PDS fragments. We hypothesized that SMRFs targeting more locations on an RNA causes greater RNA degradation.

To test this hypothesis, we generated a PDS m6g6 (six guides targeting six different regions of the PDS transcript) by adding three additional crRNA fragments to the PDS m3g3 construct (FIG. 21a). Two weeks after systemic TRV movement, PDS m6g6 crRNA SMRFs elicited a completely clear photobleaching phenotype in the lower and newly emerged leaves (FIG. 21b and FIG. 24). The visual photobleaching phenotype elicited with PDS m6g6 crRNA SMRFs was same as the photobleaching pattern caused by the conventional RNAi antisense PDS fragment. No visible differences were observed in the photobleaching phenotype elicited by PDS m6g6 constructs containing LbuDR or noDR sequence between the guides. Expressing PDS m3g3 crRNA produced a mosaic photobleaching phenotype in lower leaves while the top leaves remained green, and the TRV$_{empty}$ control plants lacked any photobleaching appearance. Supporting the visual photobleaching patterns, ~95% chlorophyll content reduction was elicited with PDS m6g6 with or without DR and antisense PDS, and PDS m3g3 caused a 76% reduction compared to TRV$_{empty}$ (FIG. 21c). We observed a significant difference in chlorophyll content levels between PDS m6g6 and PDS m3g3 crRNA. Collectively, these results demonstrate the strength of photobleaching phenotype, elicited by PDS silencing, increased with an increase in the number of guide crRNA in the PDS multi-guide.

Increasing Guide Dosage of Single-Guides Produced Stronger Silencing

RNAi off-targeting activity stems from sRNA generated through DCL-mediated cleavage of dsRNA and additional sRNA generation by RdRP. Previously, we reported the antisense PDS fragment caused more sRNA production against the PIS transcript compared to a lesser and almost no sRNA elicited by PDS m3g3 and single-guide respectively. We observed the fewer sRNA generated with PDS m3g3 were against the PDS RNA in the intervening space between the three PDS guides. In contrast, s-guide targeting only one region on the PDS RNA caused no silencing but also did not produce any sRNA. One possible explanation for reduced PDS silencing with PDS m3g3 and s-guides results from their fewer sRNA generation compared to the antisense PDS fragment. Based on these findings, we hypothesized the SMRRT silencing construct design that elicits strong RNA degradation while generating fewer sRNA can be used as an RNAi alternative for crop improvement. Our previous SMRRT silencing construct design, PDS m6g6 crRNA elicited a strong visible photobleaching pattern (FIG. 21b), like antisense PDS, but targeting six different RNA regions could lead to an increase in sRNA levels in the intervening space between PDS m6g6 crRNA. Another possible SMRRT silencing construct design for effectively silencing PDS RNA while synthesizing fewer sRNA involves increasing the fragment dosage of s-guides.

We tested the potential of increased s-guides dosage to induce strong photobleaching by assembling PDS m3g1 (3 repeat fragments targeting the same RNA, PDS m3g1-1, -2, and -3) and PDS m6g1 (6 repeat fragments targeting the same RNA, PDS m6g1-1, -2, and -3) TRV constructs (FIG. 22a). Expression of PDS m3g1-3 construct elicited a mosaic, less white, and lower reduction in chlorophyll content in the lower leaves while the top leaves remained green (FIG. 22b, 22c, and FIG. 25). Photobleaching elicited by PDS m3g1-2 was weaker compared to PDS m3g1-3, and PDS m3g1-1 crRNA caused no visible photobleaching. The photobleaching pattern elicited with PDS m3g1-3 was same as the phenotype caused by PDS m3g3. Interestingly, the three PDS m6g1 crRNA treatments elicited an increased photobleaching phenotype and greater chlorophyll reduction compared to PDS m3g1 crRNA (FIG. 22b, 22c, and FIG. 25). Comparing plants infiltrated with PDS m6g1-3 with antisense PDS revealed similar photobleaching pattern in the lower leaves, whereas the newly emerged leaves with PDS m6g1-3 crRNA remained green and antisense PDS fragment elicited a clear photobleaching phenotype (FIG. 25). Among the three PDS s-guides tested, only PDS s-guide 3 caused partial photobleaching and reduced 40% chlorophyll content compared to TRV$_{empty}$ control. The NT m3g3 and TRV$_{empty}$ controls lacked any photobleaching phenotype, as expected. Supporting the visible photobleaching phenotype in the lower leaves, chlorophyll reduction with antisense PDS and PDS m6g1-3 was the highest with 94% lower chlorophyll, ~80% chlorophyll reduction with PDS m6g1-2, PDS m3g1-3, and PDS m3g3, and weak chlorophyll reduction with PDS m3g1-1 and m6g1-1 crRNA compared to the TRV$_{empty}$ control (FIG. 21c). Combined together, these results suggest that silencing elicited by increased fragment dosage is dependent on the RNA region targeted, and increased guide dosage can elicit stronger gene silencing with a possibility of generating fewer sRNA and reduced off-targeting effects. Increasing Guide Dosage of s-Guides Improved Silencing with Less Small RNA Generation We observed a clear photobleaching phenotype and greater chlorophyll reduction with PDS m6g1 crRNA. Despite all our promising observations on improved GIGS guide design with TRV systemic infections in *N. benthamiana*, one possibility for the increased visible photobleaching phenotype elicited by increasing guide dosage could be an artefact of small RNA generated against the viruses.

Materials and Methods

Plant Materials

*Nicotiana benthamiana* plants were grown and maintained at 22° C. under 16 h light and 8 h dark cycles at 70% relative humidity. Seeds were germinated on Berger BM1 peat moss and vermiculite mix (Hummert International, Earth City, MO). One-week after emergence, *N. benthamiana* seedlings were transplanted into individual pots. Two-week-old seedlings were used for launching TRV infectious clones using *Agrobacterium* infiltration. The infiltrated plants were maintained in the growth chambers under optimal growing conditions for two weeks.

Constructing a pTRV2 Vector with AarI Restriction Site

Tobacco rattle virus (TRV) infectious clone, a generous gift from Dr. James Carrington, was used for systemic delivery of PDS and NT multi.guide crRNA. As pTRV2 vector contained a BsaI restriction site, we assembled PEBV (pea early-browning virus) promoter followed by a AarI type-II endonuclease restriction site. Overlapping oligos of PEBV promoter, 37 bp LbuCas13a direct repeat (LbuDR) or without LbuDR (noDR), with AarI restriction site were ordered from IDT (Integrated DNA Technologies, Inc., Coralville, IA). Oligos (1 ul of 100 nm concentration) were pooled and annealed using NEB T4 Polynucleotide Kinase (New England Biolabs, Ipswich, MA). pTRV2 backbone was digested using EcoRI and MluI restriction enzymes, gel electrophoresis was conducted on a 2% agarose gel to resolve the digested fragments. pTRV2 digested backbone was purified using Promega Wizard SV Gel and PCR Clean-Up System (Promega, Madison, WI). The assembled PEBV promoter with EcoRI and MluI overhangs was ligated overnight with the digested pTRV2 backbone using T4 DNA ligase (Promega Corporation, Madison, WI). Ligated pTRV2 was transformed into *E. coli* and selected on LB media with Kanamycin (50 µg/mL). PEBV promoter sequence was confirmed by Sanger sequencing (Genewiz, South Plainfield, NJ).

Constructing TRV Infectious Clones

Reduced Multi.Guide crRNA Length

To generate PDS m.guide with reduced guide length, nucleotides were removed from the 3' end for all three single guides (FIG. 17b, FIG. 23). pTRV2 backbone containing PEBV with LbuDR or noDR and AarI restriction sites were digested using AarI for 4 h. pTRV2 backbone after restriction digestion was purified to remove the fragment between two AarI restriction sites using Promega Wizard SV Gel and PCR Clean-Up System. Golden gate cloning was used to assemble PEBV-AarI digested backbone and reduced PDS m.guide crRNA with 4 bp overhangs, and transformed into *E. coli* for Kanamycin selection. Colony PCR was conducted using PEBV forward and PDS s.guide3 reverse primers to identify positive clones. Sequence of reduced PDS multi.guide crRNA was confirmed using Sanger sequencing with a PEBV promoter primer. Confirmed plasmid was extracted from *E. coli* Top10 competent cells and transformed into *Agrobacterium* GV3101 competent cells. Selection for positive transformants was conducted on Modified DR Between erRNA For LbuCas13a-mediated gene silencing, m.guide crRNA consisted of three 28nt s.guides and a direct repeat of 37 bp at the 5' end of each guide (FIG. 17a). As GIGS does not require Cas13a protein processing of a m-guide crRNA into individual crRNA, we tested the flexibility of sequence required at the 5' end of s.guides for GIGS. We tested PDS m.guide with four constructs (a) NoDR: no direct repeat between three s.guide crRNA, (b) Stem-loop: replaced LbuDR with *Arabidopsis* 24nt miR170 stemloop, (c) Loop: *Arabidopsis* miR170 stemloop without stem (16nt), and (d) Random: a 20nt randomly generated nucleotide sequence. Luciferase m.guide with NoDR, Stem-loop, Loop, and Random sequences were designed for including as nontarget (NT) controls. PDS and NT m.guide oligos were ordered from IDT, annealed using T4PNK ligase, cloned into pTRV2-PEBV backbone, and selected using Kanamycin. Sanger sequence was conducted to confirm PDS and NT m.guide crRNA.

Constructing Reduced PDS Guides with and without LbuCas13a pENTR vector backbone was digested with BsaI restriction enzyme and PDS multi.guide annealed oligos were ligated using T4 DNA ligase. In pGWB413::35SLbuCas13a vector, 35S promoter was used to drive the expression of LbuCas13a.

Measuring Chlorophyll Content

SPAD Chlorophyll Meter which instantly measures chlorophyll content or "greenness" of plants.

Example 3

The prior work exemplified in three plant species (*Nicotiana benthamiana* and *Solanum lycopersicum*, and *Arabidopsis*) is extended to a soybean (*Glycine max*). SMRRT silencing constructs were designed for silencing enhanced green fluorescent protein (EGFP) RNA in soybean hairy roots that were constitutively expressing the fluorescent protein.

Evaluating increased guide dosage in soybean hairy roots against enhanced green fluorescent protein revealed that increased guide dosage confers strong RNA silencing in soybean. Small RNA sequencing from soybean hairy roots showed fewer small RNA production with increased guide dosage and fewer off-target effects compared to RNAi. Our results demonstrate the potential of improved SMRRT silencing for transcriptome engineering to bypass pleiotropic effects in crop improvement.

TABLE

| Summary of optimized guide design in soybean hairy roots | | |
| --- | --- | --- |
| | # of hairy roots | # of roots showing GFP reduction |
| Rep 1 | | |
| Luc-Control | 7 | 1 |
| eGFP.antisense | 7 | 3 |
| eGFP.m3g3 | 7 | 5 |
| eGFP.m6g1.1 | 5 | 1 + 1(?) |
| eGFP.m6g1.2 | 7 | 3 |
| eGFP.m6g1.3 | 7 | 1 |
| Rep 2 | | |
| Luc-Control | 8 | 1 |
| eGFP.antisense | 8 | 3 |
| eGFP.m3g3 | 8 | 4 |
| eGFP.m6g1.1 | 8 | 3 |
| eGFP.m6g1.2 | 8 | 3 |
| eGFP.m6g1.3 | 8 | 2 |

The results are shown in FIG. 26A and FIG. 26B.

SEQUENCE LISTING

```
<160> NUMBER OF SEQ ID NOS: 76

<210> SEQ ID NO 1
<211> LENGTH: 3561
<212> TYPE: DNA
<213> ORGANISM: Leptotrichia bucallis

<400> SEQUENCE: 1
atgtacccgt atgacgtgcc ggattatgcg tacccgtacg acgttccgga ctatgcgtac     60
ccgtatgatg ttccggatta tgcgaaagtg accaaggttg gtggcatcag ccacaagaaa    120
tacaccagcg aaggtcgtct ggttaaaagc gagagcgagg aaaaccgtac cgacgagcgt    180
ctgagcgcgc tgctgaacat gcgtctggat atgtacatta agaacccgag cagcaccgaa    240
accaaagaga accagaagcg tatcggtaaa ctgaagaaat tctttagcaa caaaatggtg    300
tatctgaagg acaacaccct gagcctgaaa aacggcaaga agaaaaacat tgaccgtgaa    360
tacagcgaga ccgatatcct ggagagcgac gtgcgtgata agaaaaactt cgcggttctg    420
aagaaaatct acctgaacga aaacgtgaac agcgaggaac tggaggtttt ccgtaacgat    480
attaagaaaa agctgaacaa aatcaacagc ctgaagtaca gctttgagaa gaacaaggcg    540
aactaccaaa aaattaacga gaacaacatc gaaaaggttg agggcaagag caagcgtaac    600
atcatctacg actactatcg tgaaagcgcg aaacgtgatg cgtatgtgag caacgtgaaa    660
gaggcgttcg acaaactgta caaggaagag gacattgcga aactggtgct ggaaatcgag    720
aacctgacca agctggaaaa atacaagatc cgtgaattct atcacgagat cattggccgt    780
aagaacgaca aggagaactt tgcgaagatc atctacgagg aaattcagaa cgttaacaac    840
atgaaagaac tgatcgagaa ggtgccggat atgagcgagc tgaaaaagag ccaagtgttc    900
tacaagtact atctggacaa agaggagctg aacgataaaa acattaagta tgcgttctgc    960
cactttgttg aaatcgagat gagccagctg ctgaaaaact acgtgtataa gcgtctgagc   1020
aacattagca acgacaaaat caagcgtatc ttcgaatacc aaaacctgaa aaagctgatc   1080
gagaacaagc tgctgaacaa actggatacc tacgtgcgta actgcggtaa atataactac   1140
tatctgcagg acggcgaaat tgcgaccagc gatttcatcg cgcgtaaccg tcaaaacgag   1200
gcgtttctgc gtaacatcat tggtgtgagc agcgttgcgt acttcagcct gcgtaacatt   1260
```

-continued

```
ctggaaaccg agaacgaaaa cgacatcacc ggtcgtatgc gtggcaaaac cgttaagaac    1320
aacaaaggcg aggaaaaata cgtgagcggc gaagttgata agatctataa cgagaacaaa    1380
aagaacgaag tgaaggagaa cctgaaaatg ttctacagct atgactttaa catggataac    1440
aagaacgaga ttgaagactt ctttgcgaac atcgatgaag cgatcagcag cattcgtcac    1500
ggtattgttc acttcaacct ggagctggaa ggcaaagaca tcttcgcgtt taagaacatt    1560
gcgccgagcg agatcagcaa aaagatgttt cagaacgaaa ttaacgagaa aaagctgaaa    1620
ctgaagatct tccgtcaact gaacagcgcg aacgtgtttc gttacctgga aaagtataag    1680
atcctgaact acctgaagcg tacccgtttc gagtttgtga acaagaacat cccgttcgtt    1740
ccgagcttta ccaaactgta tagccgtatt gacgatctga agaacagcct gggtatctac    1800
tggaagaccc cgaaaaccaa cgacgataac aaaaccaagg aaatcattga cgcgcagatc    1860
tacctgctga aaaacatcta ctatggtgaa ttcctgaact actttatgag caacaacggc    1920
aacttctttg agatcagcaa agaaatcatt gagctgaaca agaacgacaa acgtaacctg    1980
aagaccggct tctataagct gcagaagttc gaagatatcc aagagaagat cccgaaagag    2040
tacctggcga acattcagag cctgtatatg atcaacgcgg gtaaccaaga cgaggaagag    2100
aaggacacct acatcgattt cattcaaaag atcttcctga aaggctttat gacctacctg    2160
gcgaacaacg gtcgtctgag cctgatctat attggcagcg acgaagagac caacaccagc    2220
ctggcggaga agaagcagga gttcgataag ttcctgaaaa agtacgaaca aaacaacaac    2280
atcaagattc cgtatgaaat caacgagttc ctgcgtgaaa ttaaactggg taacatcctg    2340
aagtacaccg agcgtctgaa catgttttat ctgatcctga aactgctgaa ccacaaggaa    2400
ctgaccaacc tgaaaggcag cctggagaag taccagagcg cgaacaaaga gagggcgttc    2460
agcgaccaac tggagctgat taacctgctg aacctggata caaccgtgt taccgaagac    2520 tttgagctgg aagcggatga gatcggtaaa ttcctggact ttaacggcaa caaagtgaag    2580
gataacaaag aactgaaaaa gttcgacacc aacaagatct actttgatgg cgagaacatc    2640
attaagcacc gtgcgttcta caacattaaa aagtatggta tgctgaacct gctggagaag    2700
atcgcggaca aagcgggcta caagatcagc attgaagagc tgaaaaagta tagcaacaaa    2760
aagaacgaga tcgaaaagaa ccacaaaatg caggaaaacc tgcaccgtaa atatgcgcgt    2820
ccgcgtaagg atgagaaatt caccgacgaa gattacgaga gctataagca ggcgattgaa    2880
aacatcgaag agtacaccca cctgaaaaac aaggttgagt tcaacgagct gaacctgctg    2940
caaggtctgc tgctgcgtat tctgcaccgt ctggtgggct acaccagcat ctgggagcgt    3000
gacctgcgtt tccgtctgaa gggtgaattt ccggagaacc agtacatcga agagatcttc    3060
aacttcgaaa acaaaagaa cgtgaaatac aagggtggcc agatcgttga gaagtacatc    3120
aaattctata aggaactgca ccaaaacgac gaggttaaaa ttaacaagta cagcagcgcg    3180
aacatcaaag tgctgaagca agagaagaag gatctgtaca ttcgtaacta tatcgcgcac    3240
tttaactaca ttccgcacgc ggagatcagc ctgctggaag ttctggagaa cctgcgtaaa    3300
ctgctgagct atgaccgtaa actgaagaac gcggttatga aaagcgtggt tgatattctg    3360
aaggagtacg gcttcgtggc gacctttaag atcggtgcgg acaaaaagat cggcattcag    3420
accctggaga gcgaaaaaat cgttcacctg aagaacctga aaaagaaaaa gctgatgacc    3480
gatcgtaaca gcaagagct gtgcaaactg gtgaagatta tgttcgaata caagatggag    3540
gagaaaaaga gcgagaacta a                                               3561
```

-continued

```
<210> SEQ ID NO 2
<211> LENGTH: 4431
<212> TYPE: DNA
<213> ORGANISM: Lachnospiraceae bacterium

<400> SEQUENCE: 2
atggactaca aggaccacga cggtgactac aaggaccacg acatcgacta caaggacgac      60
gacgacaaga aaatcagtaa agttcgtgag gaaaatcgag gtgccaagct taccgttaac     120
gctaaaactg cagtcgtttc cgagaacaga tcacaggagg gcattttata caacgatccc     180
tctagatatg ggaaaagtag gaaaaacgac gaggacagag acaggtacat tgagtcaagg     240
ctgaagagta gtggaaaatt atatagaatt ttcaatgagg acaaaaataa gagagaaact     300
gacgaactcc aatggttttt gagcgaaatt gtgaaaaaga tcaaccgtcg taacggcctt     360
gttcttagtg acatgctttc agtggatgat cgtgctttcg aaaaagcctt cgaaaaatac     420
gctgagttgt cttacacgaa cagacgaaat aaagtcagtg gttctcccgc atttgaaaca     480
tgtggggtcg acgcagctac tgcagagcga ctgaagggga taataagtga gacaaacttt     540
attaatcgta ttaaaaataa catagacaat aaggtctcag aagacattat agatcgtata     600
atagcaaagt atttgaagaa aagcctttgc cgtgaaaggg ttaagcgtgg attaaagaag     660
ctcttgatga atgcatttga cttaccgtac agtgatcccg acattgacgt acaacgagat     720
tttatagact atgtccttga agattttttat cacgtgagag caaagagtca agttagtaga     780
agtattaaga atatgaatat gccagtacag cccgaggggg acgggaaatt cgctataacc     840
gtctccaagg gcgggactga atcagggaac aagcgaagcg cagagaagga ggcttttaag     900 aaattttttat cagattacgc atctttagat gagagagtgc gagatgacat gttacgtcga     960
atgagaaggc ttgtcgtact ttatttttac ggttccgacg attctaaatt gtctgatgtt    1020
aatgaaaaat tcgatgtttg ggaagatcat gctgctcgta gggtggataa cagggagttc    1080
ataaagcttc cgctggaaaa caaactggcc aacgggaaga ccgataaaga tgccgagagg    1140
attcgaaaga atacagtaaa ggaactgtac agaaaccaaa atattgggtg ttaccgacaa    1200
gcagtcaagg cagtggaaga ggataataac gggcgatatt ttgacgacaa gatgctcaat    1260 atgttttttta ttcaccgtat cgaatatgga gtcgagaaaa tatacgcaaa cctcaaacag    1320
gttactgaat ttaaagctag gactgggtat ttaagcgaaa aaatttggaa agatctcata    1380
aactacatat ccataaagta tatcgcaatg ggtaaagcag tctacaacta tgcaatggat    1440
gaattaaatg ccagcgacaa gaaggagatc gagctcggga aaatatcaga agaatatttg    1500
tctgggatca gtagtttcga ttacgagctt ataaaggcag aagaaatgtt acagcgtgaa    1560
actgccgtct atgtggcttt cgccgccagg cacctgtcat ctcaaacagt tgagttggat    1620
tcagagaata gcgacttcct tctcttgaaa ccgaagggca caatggataa gaatgataag    1680
aacaaactcg catcaaataa catcctgaat tttctcaaag acaaagaaac cctcagggac    1740
actattttac aatactttgg tgggcacagc ctttggaccg attttccctt tgacaaatat    1800
ctggcagggg gtaaggatga cgttgatttt ctcaccgact tgaaagacgt gatctacagc    1860
atgcgaaacg acagcttcca ttatgctaca gaaaaccata taacggcaa gtggaacaaa    1920 gagcttatct ccgctatgtt cgaacatgaa actgaaagaa tgacagtagt aatgaaggat    1980 aaatttttact ctaacaactt accgatgttt tacaagaacg atgatctgaa gaaactctta    2040
attgaccttt acaaggacaa cgtcgagcga gcctcacagg tcccctcctt taataaggtg    2100
tttgtccgaa agaactttcc cgccttagtc cgtgacaagg acaatcttgg gatagagctg    2160
```

-continued

```
gatctgaagg cagatgcaga taagggcgaa aacgagctga agttttataa cgctctttat    2220
tatatgttca aggaaattta ctataatgca ttcttgaacg ataaaaatgt gagggagagg    2280
ttcatcacta aggccaccaa agtagcagac aattacgacc gaaacaagga gaggaatctt    2340
aaagaccgaa ttaaaagtgc tgggagtgat gaaaaaaaga aacttcgtga gcagttgcag    2400
aattacatag cagaaaacga tttcggacag aggattaaga acatagtaca ggttaaccca    2460
gattatacct tggcacaaat atgtcagctt ataatgactg agtacaacca acaaaacaac    2520
gggtgtatgc agaaaaagag tgcagccaga aaagacatta acaaggattc ataccagcac    2580
tataagatgc ttctgttggt aaacctgaga aaagcattcc tggaattcat caaagaaaac    2640
tatgcatttg tgttgaagcc gtataagcac gatctctgtg acaaagccga tttttgttccc    2700 gatttcgcaa aatatgtgaa accatatgca ggcctcattt cacgagtcgc cgggagcagt    2760
gagctccaaa agtggtatat tgtatcacgt ttcttgtccc cggcacaagc caaccacatg    2820
ttgggattcc tgcatagtta caaacagtac gtatgggaca tctatcgtcg tgctagtgaa    2880
actgggactg agataaatca ttctatagcc gaggataaaa tagcaggtgt cgatattacc    2940
gacgtggatg cagtcattga ccttagcgta aaactctgtg gcacgatttc ttctgaaata    3000
agtgattact tcaaggacga cgaggtttac gccgaatata tttccagcta cctggatttc    3060
gagtacgatg gtggtaacta caaggactct ctgaacaggt tttgtaattc agacgctgta    3120
aacgatcaaa aggtagcatt atattatgat ggcgaacatc caaagttaaa tcgaaacatt    3180
attttatcca agctgtatgg ggagagaagg ttccttgaga agattaccga cagagttagc    3240
aggtccgata tagtggagta ttacaagtta aagaaagaga cgagccaata tcaaactaaa    3300
ggcatctttg acagtgagga cgagcaaaag aacataaaaa aattccaaga aatgaaaaat    3360
atagtagagt ttagagatct tatggattat agtgagattg cagatgagct ccaaggacag    3420
ctgatcaact ggatatatct gagagaacgt gacttgatga acttccagct tggctaccac    3480
tatgcctgtc ttaacaacga ctctaataaa caagccacct acgtgacact tgattaccag    3540
ggtaaaaaaa acaggaagat caatgggggcc atactttacc agatctgtgc tatgtatatt    3600
aacgggctcc cactttacta cgtagataag gattccagcg aatggacagt tagtgacggc    3660
aaggaatcaa cgggtgcaaa gataggtgaa ttttataggt acgctaagtc atttgagaat    3720
acatccgact gttatgcttc tggcttagaa atattcgaga atatatctga acacgataac    3780
ataacggagc ttagaaacta tatcgaacac tttcgatact attcatcctt cgaccgttct    3840 ttttaggaa tttactccga ggtattcgac cgatttttta cgtacgatct gaaatatagg    3900
aaaaacgtcc ccacgatact ctacaatata ttactccaac acttcgttaa cgtcaggttc    3960
gaatttgtct ctggtaaaaa gatgataggg atagacaaaa aggataggaa aatagctaaa    4020
gagaaagagt gcgctaggat tacaatcagg gagaagaatg gcgtatattc tgagcagttt    4080
acatacaaat tgaagaacgg tactgtgtat gtggacgcac gagacaaacg ttacctgcag    4140
tccattatca ggctgttatt ttacccagaa aaggtgaata tggatgagat gatcgaggtg    4200
aaggagaaga agaaaccgag cgataataat accggaaaag ggtatagtaa aagggatcgt    4260
caacaagaca ggaaagaata cgataaatac aaggaaaaaa agaagaaaga gggtaatttt    4320
ctcagcggga tgggagggaa catcaactgg gatgagatta atgctcaatt gaaaaacggc    4380
ggcgggggtt ctggcggagg aggtagcggg gggggggga gccctaggta a              4431
```

<210> SEQ ID NO 3

```
<211> LENGTH: 1761
<212> TYPE: DNA
<213> ORGANISM: Nicotiana benthamiana

<400> SEQUENCE: 3
atgccccaaa ttggacttgt ttctgccgtt aatttgagag tccaaggtaa ttcagcttat      60
ctttggagct cgaggtcttc gttgggaact gaaagtcaag atgtttgctt gcaaaggaat     120
ttgttatgtt ttggtagtag cgactccatg gggcataagt taaggattcg tactccaagt     180
gccacgaccc gaagattgac aaaggacttt aatcctttaa aggtagtctg cattgattat     240
ccaagaccag agctagacaa tacagttaac tatttggagg cggcgttatt atcatcatcg     300
tttcgtactt cctcacgccc aactaaacca ttggagattg ttattgctgg tgcaggtttg     360
ggtggtttgt ctacagcaaa atatctggca gatgctggtc acaaaccgat attgctggag     420
gcaagagatg tcctaggtgg gaaggtagct gcatggaaag atgatgatgg agattggtac     480
gagactgggt tgcacatatt ctttgggggct tacccaaata tgcagaacct gtttggagaa     540
ctagggattg atgatcggtt gcagtggaag gaacattcaa tgatatttgc gatgcctaac     600
aagccagggg agttcagccg ctttgatttt cctgaagctc ttcctgcgcc attaaatgga     660
attttggcca tactaaagaa caacgaaatg cttacgtggc ccgagaaagt caaatttgct     720
attggactct tgccagcaat gcttggaggg caatcttatg ttgaagctca agacggttta     780
agtgttaagg actggatgag aaagcaaggt gtgcctgata gggtgacaga tgaggtgttc     840
attgccatgt caaaggcact taacttcata aaccctgacg agctttcgat gcagtgcatt     900
ttgattgctt tgaacagatt tcttcaggag aaacatggtt caaaaatggc ctttttagat     960
ggtaaccctc ctgagagact ttgcatgccg attgtggaac atattgagtc aaaaggtggc    1020
caagtcagac taaactcacg aataaaaaag atcgagctga atgaggatgg aagtgtcaaa    1080
tgttttatac tgaataatgg cagtacaatt aaaggagatg cttttgtgtt tgccactcca    1140
gtggatatct tgaagcttct tttgcctgaa gactggaaag agatcccata tttccaaaag    1200
ttggagaagc tagtgggagt tcctgtgata aatgtccata tatggtttga cagaaaactg    1260
aagaacacat ctgataatct gctcttcagc agaagcccgt tgctcagtgt gtacgctgac    1320
atgtctgtta catgtaagga atattacaac cccaatcagt ctatgttgga attggtattt    1380
gcacccgcag aagagtggat aaatcgtagt gactcagaaa ttattgatgc tacaatgaag    1440
gaactagcga agcttttccc tgatgaaatt tcggcagatc agagcaaagc aaaaatattg    1500
aagtatcatg ttgtcaaaac cccaaggtct gtttataaaa ctgtgccagg ttgtgaaccc    1560
tgtcggccct tgcaaagatc ccctatagag ggtttttatt tagctggtga ctacacgaaa    1620
cagaagtact tggcttcaat ggaaggtgct gtcttatcag gaaagctttg tgccgaagct    1680
attgtacagg attacgagtt acttcttggc cggagccaga gatgttggc agaagcaagc    1740 gtagttagca tagtgaacta a                                              1761

<210> SEQ ID NO 4
<211> LENGTH: 1752
<212> TYPE: DNA
<213> ORGANISM: Solanum lycopersicum

<400> SEQUENCE: 4
atgcctcaaa ttggacttgt ttctgctgtt aacttgagag tccaaggtag ttcagcttat      60
ctttggagct cgaggtcgtc ttctttggga actgaaagtc gagatggttg cttgcaaagg     120
aattcgttat gttttgctgg tagcgaatca atgggtcata agttaaagat cgtactcccc     180
```

```
catgccacga ccagaagatt ggttaaggac ttggggcctt taaaggtcgt atgcattgat      240
tatccaagac cagagctgga caatacagtt aactatttgg aggctgcatt tttatcatca      300
acgttccgtg cttctccgcg cccaactaaa ccattggaga ttgttattgc tggtgcaggt      360
ttgggtggtt tgtctacagc aaaatatttg gcagatgctg gtcacaaacc gatactgctg      420
gaggcaaggg atgttctagg tggaaaggta gctgcatgga aagatgatga tggagattgg      480
tacgagactg tgtttgcatat attctttggg gcttacccaa atattcagaa cctgtttgga      540
gaattaggga ttaacgatcg attgcaatgg aaggaacatt caatgatatt tgcaatgcca      600
agcaagccag gagaattcag ccgctttgat ttctccgaag ctttacccgc tcctttaaat      660
ggaattttag ccatcttaaa gaataacgaa atgcttacat ggccagagaa agtcaaattt      720
gcaattggac tcttgccagc aatgcttgga gggcaatctt atgttgaagc tcaagatggg      780
ataagtgtta aggactggat gagaaagcaa ggtgtgccgg acagggtgac agatgaggtg      840
ttcattgcta tgtcaaaggc actcaacttt ataaaccctg acgaactttc aatgcagtgc      900
attttgatcg cattgaacag gtttcttcag gagaaacatg gttcaaaaat ggccttttta      960
gatggtaatc ctcctgagag actttgcatg ccgattgttg aacacattga gtcaaaaggt     1020
ggccaagtca gactgaactc acgaataaaa aagattgagc tgaatgagga tggaagtgtc     1080
aagagtttta tactgagtga cggtagtgca atcgagggag atgcttttgt gtttgccgct     1140
ccagtggata ttttcaagct tctattgcct gaagactgga aagagattcc atatttccaa     1200
aagttggaga agttagtcgg agtacctgtg ataaatgtac atatatggtt tgacagaaaa     1260
ctgaagaaca catatgatca tttgctcttc agcagaagct cactgctcag tgtgtatgct     1320
gacatgtctg ttacatgtaa ggaatattac aaccccaatc agtctatgtt ggaattggtt     1380
tttgcacctg cagaagagtg gatatctcgc agcgactcag aaattattga tgcaacgatg     1440
aaggaactag caacgctttt tcctgatgaa atttcagcag atcaaagcaa agcaaaaata     1500
ttgaagtacc atgttgtcaa aactccgagg tctgtttata aaactgtgcc aggttgtgaa     1560
ccctgtcggc ctttacaaag atccccaata gaggggtttt atttagccgg tgactacacg     1620
aaacagaaat acttggcttc aatggaaggc gctgtcttat caggaaagct ttgtgctcaa     1680
gctattgtac aggattatga gttacttgtt ggacgtagcc aaaagaagtt gtcggaagca     1740
agcgtagttt ag                                                        1752

<210> SEQ ID NO 5
<211> LENGTH: 1042
<212> TYPE: DNA
<213> ORGANISM: Arabidopsis thaliana

<400> SEQUENCE: 5
atggataatt cagctccaga ttcgttatcc agatcggaaa ccgccgtcac atacgactca       60
ccatatccac tctacgccat ggctttctct tctctccgct catcctccgg tcacagaatc      120
gccgtcggaa gcttcctcga agattacaac aaccgcatcg acattctctc tttcgattcc      180
gattcaatga ccgttaagcc tctcccgaat ctctccttcg agcatcctta tcctccaaca      240
aagctaatgt tcagtcctcc ttctctccgt cgtccttcct ccggagatct cctcgcttcc      300
tccggcgatt tcctccgtct ttgggaaatt aacgaagatt catcaaccgt cgagccaatc      360
tcggttctca caacagcaa aacgagcgag ttttgtgcgc cgttgacttc cttcgattgg      420
aacgatgtag agccgaaacg tctcggaact tgtagtattg atacgagctc cttagagttt      480
```

-continued

```
gacgtgtacg atttgggata ttgagaagtc tgttgttgag actcagctta tagctcatga      540
taaagaggtt catgacattg cttggggaga agctagggtt ttcgcatcag tctctgctga      600
tggatccgtt aggatctttg atttacgtga taaggaacat tctacaatca tttacgagag      660
tcctcagcct gatacgcctt tgttaagact tgcttggaac aaacaagatc ttagatatat      720
ggctacgatt ttgatggatt ctaataaggt tgtgattctc gatattcgtt cgccgactat      780
gcctgttgct gagcttgaaa gacatcaggc tagtgtgaat gctatagctt gggcgcctca      840
gagctgtaaa catatttgtt ctggtggtga tgatacacag gctcttattt gggagcttcc      900
tactgttgct ggacccaatg ggattgatcc gatgtcggtt tattcggctg gttcggagat      960
taatcagttg cagtggtctt cttcgcagcc tgattggatt ggtattgctt ttgctaacaa     1020
aatgcagctc cttagagttt ga                                              1042
```

<210> SEQ ID NO 6
<211> LENGTH: 1350
<212> TYPE: DNA
<213> ORGANISM: Artificial Sequence
<220> FEATURE:
<223> OTHER INFORMATION: Synthetic RNAi PDS hairpin construct

<400> SEQUENCE: 6

```
gctggaattc tagtatacta aaccaatgga ctttgcatgc cgattgtgga acatattgag       60
tcaaaaggtg gccaagtcag actaaactca cgaataaaaa agatcgagct gaatgaggat      120
ggaagtgtca aatgttttat actgaataat ggcagtacaa ttaaaggaga tgcttttgtg      180
tttgccactc cagtggatat cttgaagctt cttttgcctg aagactggaa agagatccca      240
tatttccaaa agttggagaa gctagtggga gttcctgtga taaatgtcca tatatggttt      300
gacagaaaac tgaagaacac atctgataat ctgctcttca gcagaagccc gttgctcagt      360
gtgtacgctg acatgtctgt tacatgtaag gaatattaca accccaatca gtctatgttg      420
gaattggtat ttgcacccgc agaagagtgg ataaatcgta gtgactcaga aattattgat      480
gctacaatga aggaactagc gaagcttttc cctgatgaaa tttcggcagt actctttctg      540
ggagtttcga attttgttgt ttctagaatt cgaatttgtg attttgcgga actttgaatt      600
gatatttgtg ttggttgatt gtctaagtgt tgttggttct tattagattt ttttggatat      660
tgtagattta atgtaaagtt ggtgtgagat tattatttca agcttctttt aattcaaagg      720 ctttttaaagc taatgctaca gtgaaattga atgcttagaa gattgtttgg aacgaaaaca      780
gattttggca tttttgtgga tgatgtgtta tgttgaaacg ttgtctcatt ttcatgttgt      840
attgtagtgc cgaaatttca tcagggaaaa gcttcgctag ttccttcatt gtagcatcaa      900
taatttctga gtcactacga tttatccact cttctgcggg tgcaaatacc aattccaaca      960
tagactgatt ggggttgtaa tattccttac atgtaacaga catgtcagcg tacacactga     1020
gcaacgggct ctgctgaag agcagattat cagatgtgtt cttcagtttt ctgtcaaacc     1080
atatatggac atttatcaca ggaactccca ctagcttctc caacttttgg aaatatggga     1140
tctctttcca gtcttcaggc aaaagaagct tcaagatatc cactggagtg gcaaacacaa     1200
aagcatctcc tttaattgta ctgccattat tcagtataaa acatttgaca cttccatcct     1260
cattcagctc gatctttttt attcgtgagt ttagtctgac ttggccacct tttgactcaa     1320
tatgttccac aatcggcatg caaagtccat                                      1350
```

<210> SEQ ID NO 7
<211> LENGTH: 10964
```

-continued

```
<212> TYPE: DNA
<213> ORGANISM: Artificial Sequence
<220> FEATURE:
<223> OTHER INFORMATION: Synthetic plasmid pGWB413

<400> SEQUENCE: 7
tttcacgccc ttttaaatat ccgattattc taataaacgc tcttttctct taggtttacc     60
cgccaatata tcctgtcaaa cactgatagt ttaaactgaa ggcgggaaac gacaatctga    120
tccaagctca agctgctcta gcattcgcca ttcaggctgc gcaactgttg ggaagggcga    180
tcggtgcggg cctcttcgct attacgccag ctggcgaaag ggggatgtgc tgcaaggcga    240
ttaagttggg taacgccagg gttttcccag tcacgacgtt gtaaaacgac ggccagtgcc    300
aagcttgcat gcctgcaggt cgactctaga gttatcaaca gtttgtaca aaaaagctga    360 acgagaaacg taaaatgata taaatatcaa tatattaaat tagattttgc ataaaaaaca    420
gactacataa tactgtaaaa cacaacatat ccagtcacta tggcggcccc tcgaggggcc    480
gcattaggca ccccaggctt tacactttat gcttccggct cgtataatgt gtggattttg    540
agttaggatc cggcgagatt ttcaggagct aaggaagcta aaatggagaa aaaaatcact    600
ggatatacca ccgttgatat atcccaatgg catcgtaaag aacattttga ggcatttcag    660
tcagttgctc aatgtaccta taaccagacc gttcagctgg atattacggc cttttttaaag    720 accgtaaaga aaaataagca caagttttat ccggccttta ttcacattct tgcccgcctg    780
atgaatgctc atccggaatt ccgtatggca atgaaagacg gtgagctggt gatatgggat    840
agtgttcacc cttgttacac cgttttccat gagcaaactg aaacgttttc atcgctctgg    900
agtgaatacc acgacgattt ccggcagttt ctacacatat attcgcaaga tgtggcgtgt    960
tacggtgaaa acctggccta tttccctaaa gggtttattg agaatatgtt tttcgtctca   1020
gccaatccct gggtgagttt caccagtttt gatttaaacg tggccaatat ggacaacttc   1080
ttcgcccccg ttttcaccat gggcaaatat tatacgcaag cgacaaggt gctgatgccg   1140 ctggcgattc aggttcatca tgccgtctgt gatggcttcc atgtcggcag aatgcttaat   1200
gaattacaac agtactgcga tgagtggcag ggcggggcgt aaagatctgg atccggctta   1260
ctaaaagcca gataacagta tgcgtatttg cgcgctgatt tttgcggtat aagaatatat   1320
actgatatgt atacccgaag tatgtcaaaa agaggtgtgc tatgaagcag cgtattacag   1380
tgacagttga cagcgacagc tatcagttgc tcaaggcata tatgatgtca atatctccgg   1440
tctggtaagc acaaccatgc agaatgaagc ccgtcgtctg cgtgccgaac gctggaaagc   1500
ggaaaatcag gaagggatgg ctgaggtcgc ccggtttatt gaaatgaacg ctcttttgc   1560 tgacgagaac agggactggt gaaatgcagt ttaaggttta cacctataaa agagagagcc   1620
gttatcgtct gtttgtggat gtacagagt atattattga cacgcccggg cgacggatgg   1680 tgatcccccct ggccagtgca cgtctgctgt cagataaagt ctcccgtgaa ctttacccgg   1740
tggtgcatat cggggatgaa agctggcgca tgatgaccac cgatatggcc agtgtgccgg   1800
tctccgttat cggggaagaa gtggctgatc tcagccaccg cgaaaatgac atcaaaaacg   1860
ccattaacct gatgttctgg ggaatataaa tgtcaggctc ccttatacac agccagtctg   1920
caggtcgacc atagtgactg gatatgttgt gttttacagt attatgtagt ctgttttta   1980 tgcaaaatct aatttaatat attgatattt atatcatttt acgtttctcg ttcagctttc   2040
ttgtacaaag tggttgataa cagcgggtta attaacatct tttacccata cgatgttcct   2100
gactatgcgg gctatccgta tgacgtcccg gactatgcag gatcctatcc atatgacgtt   2160
```

-continued

```
ccagattacg ctgctcagtg cagcgcttag agctcgaatt tccccgatcg ttcaaacatt   2220
tggcaataaa gtttcttaag attgaatcct gttgccggtc ttgcgatgat tatcatataa   2280
tttctgttga attacgttaa gcatgtaata attaacatgt aatgcatgac gttatttatg   2340
agatgggttt ttatgattag agtcccgcaa ttatacattt aatacgcgat agaaaacaaa   2400
atatagcgcg caaactagga taaattatcg cgcgcggtgt catctatgtt actagatcgg   2460
gaattggttc cggaaccaat tcgtaatcat ggtcatagct gtttcctgtg tgaaattgtt   2520
atccgctcac aattccacac aacatacgag ccggaagcat aaagtgtaaa gcctggggtg   2580
cctaatgagt gagctaactc acattaggct gaattaggcg cgcctatttc tgaattcccg   2640
atctagtaac atagatgaca ccgcgcgcga taatttatcc tagtttgcgc gctatatttt   2700
gttttctatc gcgtattaaa tgtataattg cgggactcta atcataaaaa cccatctcat   2760
aaataacgtc atgcattaca tgttaattat tacatgctta acgtaattca acagaaatta   2820
tatgataatc atcgcaagac cggcaacagg attcaatctt aagaaacttt attgccaaat   2880
gtttgaacga tcggggatca tccgggtctg tggcgggaac tccacgaaaa tatccgaacg   2940
cagcaagata tcgcggtgca tctcggtctt gcctgggcag tcgccgccga cgccgttgat   3000
gtggacgccg ggcccgatca tattgtcgct caggatcgtg gcgttgtgct tgtcggccgt   3060
tgctgtcgta atgatatcgg caccttcgac cgcctgttcc gcagagatcc cgtgggcgaa   3120
gaactccagc atgagatccc cgcgctggag gatcatccag ccggcgtccc ggaaaacgat   3180
tccgaagccc aacctttcat agaaggcggc ggtggaatcg aaatctcgtg atggcaggtt   3240
gggcgtcgct tggtcggtca tttcgaaccc cagagtcccg ctcagaagaa ctcgtcaaga   3300
aggcgataga aggcgatgcg ctgcgaatcg ggagcggcga taccgtaaag cacgaggaag   3360
cggtcagccc attcgccgcc aagctcttca gcaatatcac gggtagccaa cgctatgtcc   3420
tgatagcggt ccgccacacc cagccggcca cagtcgatga atccagaaaa gcggccattt   3480
tccaccatga tattcggcaa gcaggcatcg ccatgggtca cgacgagatc atcgccgtcg   3540
ggcatgcgcg ccttgagcct ggcgaacagt tcggctggcg cgagcccctg atgctcttcg   3600
tccagatcat cctgatcgac aagaccggct tccatccgag tacgtgctcg ctcgatgcga   3660
tgtttcgctt ggtggtcgaa tgggcaggta gccggatcaa gcgtatgcag ccgccgcatt   3720
gcatcagcca tgatggatac ttttctcggca ggagcaaggt gagatgacag gagatcctgc   3780
cccggcactt cgcccaatag cagccagtcc cttcccgctt cagtgacaac gtcgagcaca   3840
gctgcgcaag gaacgcccgt cgtggccagc cacgatagcc gcgctgcctc gtcctgcagt   3900
tcattcaggg caccggacag gtcggtcttg acaaaaagaa ccgggcgccc ctgcgctgac   3960
agccggaaca cggcggcatc agagcagccg attgtctgtt gtgcccagtc atagccgaat   4020
agcctctcca cccaagcggc cggagaacct gcgtgcaatc catcttgttc aatcatgcga   4080
aacgatccag atccggtgca gattatttgg attgagagtg aatatgagac tctaattgga   4140
taccgagggg aatttatgga acgtcagtgg agcatttttg acaagaaata tttgctagct   4200
gatagtgacc ttaggcgact tttgaacgcg caataatggt ttctgacgta tgtgcttagc   4260
tcattaaact ccagaaaccc gcggctgagt ggctccttca acgttgcggt tctgtcagtt   4320
ccaaacgtaa aacggcttgt cccgcgtcat cggcggggt cataacgtga ctcccttaat   4380
tctccgctca tgatgaattc agaaataaat tcagcctaat tcggcgttaa ttcagtacat   4440
taaaaacgtc cgcaatgtgt tattaagttg tctaagcgtc aatttgttta caccacaata   4500
tatcctgcca ccagccagcc aacagctccc cgaccggcag ctcggcacaa aatcaccact   4560
```

-continued

```
cgatacaggc agcccatcag tccgggacgg cgtcagcggg agagccgttg taaggcggca   4620
gactttgctc atgttaccga tgctattcgg aagaacggca actaagctgc cgggtttgaa   4680
acacggatga tctcgcggag ggtagcatgt tgattgtaac gatgacagag cgttgctgcc   4740
tgtgatcaat tcgggcacga acccagtgga cataagcctg ttcggttcgt aagctgtaat   4800
gcaagtagcg tatgcgctca cgcaactggt ccagaacctt gaccgaacgc agcggtggta   4860
acggcgcagt ggcggttttc atggcttgtt atgactgttt ttttggggta cagtctatgc   4920
ctcgggcatc caagcagcaa gcgcgttacg ccgtgggtcg atgtttgatg ttatggagca   4980
gcaacgatgt tacgcagcag ggcagtcgcc ctaaaacaaa gttaaacatc atgggggaag   5040
cggtgatcgc cgaagtatcg actcaactat cagaggtagt tggcgtcatc gagcgccatc   5100
tcgaaccgac gttgctggcc gtacatttgt acggctccgc agtggatggc ggcctgaagc   5160
cacacagtga tattgatttg ctggttacgg tgaccgtaag gcttgatgaa acaacgcggc   5220
gagctttgat caacgacctt ttggaaactt cggcttcccc tggagagagc gagattctcc   5280
gcgctgtaga agtcaccatt gttgtgcacg acgacatcat tccgtggcgt tatccagcta   5340
agcgcgaact gcaatttgga gaatggcagc gcaatgacat tcttgcaggt atcttcgagc   5400
cagccacgat cgacattgat ctggctatct tgctgacaaa agcaagagaa catagcgttg   5460
ccttggtagg tccagcggcg gaggaactct ttgatccggt tcctgaacag gatctatttg   5520
aggcgctaaa tgaaacctta acgctatgga actcgccgcc cgactgggct ggcgatgagc   5580
gaaatgtagt gcttacgttg tcccgcattt ggtacagcgc agtaaccggc aaaatcgcgc   5640
cgaaggatgt cgctgccgac tgggcaatgg agcgcctgcc ggcccagtat cagcccgtca   5700
tacttgaagc tagacaggct tatcttggac aagaagaaga tcgcttggcc tcgcgcgcag   5760
atcagttgga agaatttgtc cactacgtga aaggcgagat caccaaggta gtcggcaaat   5820
aatgtctagc tagaaattcg ttcaagccga cgccgcttcg cggcgcggct taactcaagc   5880
gttagatgca ctaagcacat aattgctcac agccaaacta tcaggtcaag tctgctttta   5940
ttatttttaa gcgtgcataa taagccctac acaaattggg agatatatca tgcatgacca   6000
aaatccctta acgtgagttt tcgttccact gagcgtcaga ccccgtagaa aagatcaaag   6060
gatcttcttg agatcctttt tttctgcgcg taatctgctg cttgcaaaca aaaaaaccac   6120
cgctaccagc ggtggtttgt ttgccggatc aagagctacc aactcttttt ccgaaggtaa   6180
ctggcttcag cagagcgcag ataccaaata ctgtccttct agtgtagccg tagttaggcc   6240
accacttcaa gaactctgta gcaccgccta catacctcgc tctgctaatc ctgttaccag   6300
tggctgctgc cagtggcgat aagtcgtgtc ttaccgggtt ggactcaaga cgatagttac   6360
cggataaggc gcagcggtcg ggctgaacgg ggggttcgtg cacacagccc agcttggagc   6420
gaacgaccta caccgaactg agatacctac agcgtgagct atgagaaagc gccacgcttc   6480
ccgaagggag aaaggcggac aggtatccgg taagcggcag ggtcggaaca ggagagcgca   6540
cgagggagct tccaggggga aacgcctggt atctttatag tcctgtcggg tttcgccacc   6600
tctgacttga gcgtcgattt ttgtgatgct cgtcaggggg gcggagccta tggaaaaacg   6660
ccagcaacgc ggccttttta cggttcctgg ccttttgctg gccttttgct cacatgttct   6720
ttcctgcgtt atcccctgat tctgtggata accgtattac cgcctttgag tgagctgata   6780
ccgctcgccg cagccgaacg accgagcgca gcgagtcagt gagcgaggaa gcggaagagc   6840
gcctgatgcg gtattttctc cttacgcatc tgtgcggtat ttcacaccgc atatggtgca   6900
```

```
ctctcagtac aatctgctct gatgccgcat agttaagcca gtatacactc cgctatcgct       6960
acgtgactgg gtcatggctg cgccccgaca cccgccaaca cccgctgacg cgccctgacg       7020
ggcttgtctg ctcccggcat ccgcttacag acaagctgtg accgtctccg ggagctgcat       7080
gtgtcagagg tttttcaccgt catcaccgaa acgcgcgagg cagggtgcct tgatgtgggc      7140
gccggcggtc gagtggcgac ggcgcggctt gtccgcgccc tggtagattg cctggccgta       7200
ggccagccat ttttgagcgg ccagcggccg cgataggccg acgcgaagcg gcggggcgta       7260
gggagcgcag cgaccgaagg gtaggcgctt tttgcagctc ttcggctgtg cgctggccag       7320
acagttatgc acaggccagg cgggttttaa gagtttttaat aagttttaaa gagtttttagg     7380 cggaaaaatc gccttttttc tcttttatat cagtcactta catgtgtgac cggttcccaa       7440
tgtacggctt tgggttccca atgtacgggt tccggttccc aatgtacggc tttgggttcc       7500
caatgtacgt gctatccaca ggaaagagac cttttcgacc tttttcccct gctagggcaa       7560
tttgccctag catctgctcc gtacattagg aaccggcgga tgcttcgccc tcgatcaggt       7620
tgcggtagcg catgactagg atcgggccag cctgccccgc ctcctccttc aaatcgtact       7680
ccggcaggtc atttgacccg atcagcttgc gcacggtgaa acagaacttc ttgaactctc       7740
cggcgctgcc actgcgttcg tagatcgtct tgaacaacca tctggcttct gccttgcctg       7800
cggcgcggcg tgccaggcgg tagagaaaac ggccgatgcc gggatcgatc aaaaagtaat       7860
cggggtgaac cgtcagcacg tccgggttct tgccttctgt gatctcgcgg tacatccaat       7920
cagctagctc gatctcgatg tactccggcc gcccggtttc gctctttacg atcttgtagc       7980
ggctaatcaa ggcttcaccc tcggataccg tcaccaggcg gccgttcttg gccttcttcg       8040
tacgctgcat ggcaacgtgc gtggtgttta accgaatgca ggtttctacc aggtcgtctt       8100
tctgctttcc gccatcggct cgccggcaga acttgagtac gtccgcaacg tgtggacgga       8160
acacgcggcc gggcttgtct cccttccctt cccggtatcg gttcatggat tcggttagat       8220
gggaaaccgc catcagtacc aggtcgtaat cccacacact ggccatgccg gccggccctg       8280
cggaaacctc tacgtgcccg tctggaagct cgtagcggat cacctcgcca gctcgtcggt       8340
cacgcttcga cagacggaaa acggccacgt ccatgatgct gcgactatcg cgggtgccca       8400
cgtcatagag catcggaacg aaaaaatctg gttgctcgtc gcccttgggc ggcttcctaa       8460
tcgacggcgc accggctgcc ggcggttgcc gggattcttt gcggattcga tcagcggccg       8520
cttgccacga ttcaccgggg cgtgcttctg cctcgatgcg ttgccgctgg gcggcctgcg       8580
cggccttcaa cttctccacc aggtcatcac ccagcgccgc gccgatttgt accgggccgg       8640
atggtttgcg accgctcacg ccgattcctc gggcttgggg gttccagtgc cattgcaggg       8700
ccggcagaca acccagccgc ttacgcctgg ccaaccgccc gttcctccac acatgggggca      8760 ttccacggcg tcggtgcctg gttgttcttg attttccatg ccgcctcctt tagccgctaa       8820
aattcatcta ctcatttatt catttgctca tttactctgg tagctgcgcg atgtattcag       8880
atagcagctc ggtaatggtc ttgccttggc gtaccgcgta catcttcagc ttggtgtgat       8940
cctccgccgg caactgaaag ttgacccgct tcatggctgg cgtgtctgcc aggctggcca       9000
acgttgcagc cttgctgctg cgtgcgctcg acggccggc acttagcgtg tttgtgcttt        9060
tgctcatttt ctctttacct cattaactca aatgagtttt gatttaattt cagcggccag       9120
cgcctggacc tcgcgggcag cgtcgccctc gggttctgat tcaagaacgg ttgtgccggc       9180
ggcggcagtg cctgggtagc tcacgcgctg cgtgatacgg gactcaagaa tgggcagctc       9240
gtacccggcc agcgcctcgg caacctcacc gccgatgcgc gtgcctttga tcgcccgcga       9300
```

-continued

```
cacgacaaag gccgcttgta gccttccatc cgtgacctca atgcgctgct taaccagctc      9360
caccaggtcg gcggtggccc atatgtcgta agggcttggc tgcaccggaa tcagcacgaa      9420
gtcggctgcc ttgatcgcgg acacagccaa gtccgccgcc tggggcgctc cgtcgatcac      9480
tacgaagtcg cgccggccga tggccttcac gtcgcggtca atcgtcgggc ggtcgatgcc      9540
gacaacggtt agcggttgat cttcccgcac ggccgcccaa tcgcgggcac tgccctgggg      9600
atcggaatcg actaacagaa catcggcccc ggcgagttgc agggcgcggg ctagatgggt      9660
tgcgatggtc gtcttgcctg acccgccttt ctggttaagt acagcgataa ccttcatgcg      9720
ttccccttgc gtatttgttt atttactcat cgcatcatat acgcagcgac cgcatgacgc      9780
aagctgtttt actcaaatac acatcacctt tttagacggc ggcgctcggt ttcttcagcg      9840
gccaagctgg ccggccaggc cgccagcttg gcatcagaca aaccggccag gatttcatgc      9900
agccgcacgg ttgagacgtg cgcgggcggc tcgaacacgt acccggccgc gatcatctcc      9960
gcctcgatct cttcggtaat gaaaaacggt tcgtcctggc cgtcctggtg cggtttcatg      10020
cttgttcctc ttggcgttca ttctcggcgg ccgccagggc gtcggcctcg gtcaatgcgt      10080
cctcacggaa ggcaccgcgc cgcctggcct cggtgggcgt cacttcctcg ctgcgctcaa      10140
gtgcgcggta cagggtcgag cgatgcacgc caagcagtgc agccgcctct ttcacggtgc      10200
ggccttcctg gtcgatcagc tcgcgggcgt gcgcgatctg tgccggggtg agggtagggc      10260 ggggggccaaa cttcacgcct cgggccttgg cggcctcgcg cccgctccgg gtgcggtcga      10320
tgattaggga acgctcgaac tcggcaatgc cggcgaacac ggtcaacacc atgcggccgg      10380
ccggcgtggt ggtgtcggcc cacggctctg ccaggctacg caggcccgcg ccggcctcct      10440
ggatgcgctc ggcaatgtcc agtaggtcgc gggtgctgcg ggccaggcgg tctagcctgg      10500
tcactgtcac aacgtcgcca gggcgtaggt ggtcaagcat cctggccagc tccgggcggt      10560
cgcgcctggt gccggtgatc ttctcggaaa acagcttggt gcagccggcc gcgtgcagtt      10620
cggcccgttg gttggtcaag tcctggtcgt cggtgctgac gcgggcatag cccagcaggc      10680
cagcggcggc gctcttgttc atggcgtaat gtctccggtt ctagtcgcaa gtattctact      10740
ttatgcgact aaaacacgcg acaagaaaac gccaggaaaa gggcagggcg gcagcctgtc      10800
gcgtaactta ggacttgtgc gacatgtcgt tttcagaaga cggctgcact gaacgtcaga      10860
agccgactgc actatagcag cggaggggtt ggatcaaagt actttgatcc cgaggggaac      10920
cctgtggttg gcatgcacat acaaatggac gaacggataa acct      10964
```

```
<210> SEQ ID NO 8
<211> LENGTH: 6791
<212> TYPE: DNA
<213> ORGANISM: Artificial Sequence
<220> FEATURE:
<223> OTHER INFORMATION: Synthetic plasmid pTRV1

<400> SEQUENCE: 8
ataaaacatt tcaatccttt gaacgcggta gaacgtgcta attggatttt ggtgagaacg        60
cggtagaacg tacttatcac ctacagtttt attttgtttt tcttttttggt ttaatctatc       120 cagcttagta ccgagtgggg gaaagtgact ggtgtgcctta aaacctttc tttgatactt       180 tgtaaaaata catacagata caatggcgaa cggtaacttc aagttgtctc aattgctcaa       240
tgtggacgag atgtctgctg agcagaggag tcatttcttt gacttgatgc tgactaaacc       300
tgattgtgag atcgggcaaa tgatgcaaag agttgttgtt gataaagtcg atgacatgat       360
```

-continued

```
tagagaaaga aagactaaag atccagtgat tgttcatgaa gttctttctc agaaggaaca    420
gaacaagttg atggaaattt atcctgaatt caatatcgtg tttaaagacg acaaaaacat    480
ggttcatggg tttgcggctg ctgagcgaaa actacaagct ttattgcttt tagatagagt    540
tcctgctctg caagaggtgg atgacatcgg tggtcaatgg tcgttttggg taactagagg    600
tgagaaaagg attcattcct gttgtccaaa tctagatatt cgggatgatc agagagaaat    660
ttctcgacag atatttctta ctgctattgg tgatcaagct agaagtggta agagacagat    720
gtcggagaat gagctgtgga tgtatgacca atttcgtgaa aatattgctg cgcctaacgc    780
ggttaggtgc aataatacat atcagggttg tacatgtagg ggttttttctg atggtaagaa    840 gaaaggcgcg cagtatgcga tagctcttca cagcctgtat gacttcaagt tgaaagactt    900
gatggctact atggttgaga agaaaactaa agtggttcat gctgctatgc ttttttgctcc    960 tgaaagtatg ttagtggacg aaggtccatt accttctgtt gacggttact acatgaagaa   1020
gaacgggaag atctatttcg gttttgagaa agatccttcc ttttcttaca ttcatgactg   1080
ggaagagtac aagaagtatc tactggggaa gccagtgagt taccaaggga atgtgttcta   1140
cttcgaaccg tggcaggtga gaggagacac aatgcttttt tcgatctaca ggatagctgg   1200
agttccgagg aggtctctat catcgcaaga gtactaccga agaatatata tcagtagatg   1260
ggaaaacatg gttgttgtcc caattttcga tctggtcgaa tcaacgcgag agttggtcaa   1320
gaaagacctg tttgtagaga aacaattcat ggacaagtgt ttggattaca tagctaggtt   1380
atctgaccag cagctgacca taagcaatgt taaatcatac ttgagttcaa ataattgggt   1440
cttattcata aacggggcgg ccgtgaagaa caagcaaagt gtagattctc gagatttaca   1500
gttgttggct caaactttgc tagtgaagga acaagtggcg agacctgtca tgagggagtt   1560
gcgtgaagca attctgactg agacgaaacc tatcacgtca ttgactgatg tgctgggttt   1620
aatatcaaga aaactgtgga agcagtttgc taacaagatc gcagtcggcg gattcgttgg   1680
catggttggt actctaattg gattctatcc aaagaaggta ctaacctggg cgaaggacac   1740
accaaatggt ccagaactat gttacgagaa ctcgcacaaa accaaggtga tagtatttct   1800
gagtgttgtg tatgccattg gaggaatcac gcttatgcgt cgagacatcc gagatggact   1860
ggtgaaaaaa ctatgtgata tgtttgatat caaacggggg gcccatgtct tagacgttga   1920
gaatccgtgc cgctattatg aaatcaacga tttctttagc agtctgtatt cggcatctga   1980
gtccggtgag accgttttac cagatttatc cgaggtaaaa gccaagtctg ataagctatt   2040
gcagcagaag aaagaaatcg ctgacgagtt tctaagtgca aaattctcta actattctgg   2100
cagttcggtg agaacttctc caccatcggt ggtcggttca tctcgaagcg gactgggtct   2160
gttgttggaa gacagtaacg tgctgaccca agctagagtt ggagtttcaa gaaaggtaga   2220
cgatgaggag atcatggagc agtttctgag tggtcttatt gacactgaag cagaaattga   2280
cgaggttgtt ccagcctttt cagctgaatg tgaaagaggg gaaacaagcg gtacaaaggt   2340
gttgtgtaaa cctttaacgc caccaggatt tgagaacgtg ttgccagctg tcaaaccttt   2400
ggtcagcaaa ggaaaaacgg tcaaacgtgt cgattacttc caagtgatgg gaggtgagag   2460
attaccaaaa aggccggttg tcagtggaga cgattctgtg gacgctagaa gagagtttct   2520
gtactactta gatgcggaga gagtcgctca aaatgatgaa attatgtctc tgtatcgtga   2580
ctattcgaga ggagttattc gaactggagg tcagaattac ccgcacggac tgggagtgtg   2640
ggatgtggag atgaagaact ggtgcatacg tccagtggtc actgaacatg cttatgtgtt   2700
ccaaccagac aaacgtatgg atgattggtc gggatactta gaagtggctg tttgggaacg   2760
```

-continued

```
aggtatgttg gtcaacgact tcgcggtcga aaggatgagt gattatgtca tagtttgcga   2820
tcagacgtat ctttgcaata acaggttgat cttggacaat ttaagtgccc tggatctagg   2880
accagttaac tgttcttttg aattagttga cggtgtacct ggttgtggta agtcgacaat   2940
gattgtcaac tcagctaatc cttgtgtcga tgtggttctc tctactggga gagcagcaac   3000
cgacgacttg atcgagagat tcgcgagcaa aggtttttcca tgcaaattga aaaggagagt   3060
gaagacggtt gattcttttt tgatgcattg tgttgatggt tctttaaccg agacgtgtt   3120 gcatttcgat gaagctctca tggcccatgc tggtatggtg tactttttgcg ctcagatagc   3180 tggtgctaaa cgatgtatct gtcaaggaga tcagaatcaa atttctttca agcctagggt   3240
atctcaagtt gatttgaggt tttctagtct ggtcggaaag tttgacattg ttacagaaaa   3300
aagagaaact tacagaagtc cagcagatgt ggctgccgta ttgaacaagt actatactgg   3360
agatgtcaga acacataacg cgactgctaa ttcgatgacg gtgaggaaga ttgtgtctaa   3420
agaacaggtt tctttgaagc ctggtgctca gtacataact ttccttcagt ctgagaagaa   3480
ggagttggta aatttgttgg cattgaggaa agtggcagct aaagtgagta cagtacacga   3540
gtcgcaagga gagacattca aagatgtagt cctagtcagg acgaaaccta cggatgactc   3600
aatcgctaga ggtcgggagt acttaatcgt ggcgttgtcg cgtcacacac aatcacttgt   3660
gtatgaaact gtgaaagagg acgatgtaag caaagagatc agggaaagtg ccgcgcttac   3720
gaaggcggct ttggcaagat tttttgttac tgagaccgtc ttatgacggt ttcggtctag   3780
gtttgatgtc tttagacatc atgaagggcc ttgcgccgtt ccagattcag gtacgattac   3840
ggacttggag atgtggtacg acgctttgtt tccgggaaat tcgttaagag actcaagcct   3900
agacgggtat ttggtggcaa cgactgattg caatttgcga ttagacaatg ttacgatcaa   3960
aagtggaaac tggaaagaca agtttgctga aaaagaaacg tttctgaaac cggttattcg   4020
tactgctatg cctgacaaaa ggaagactac tcagttggag agtttgttag cattgcagaa   4080
aaggaaccaa gcggcaccccg atctacaaga aaatgtgcac gcaacagttc taatcgaaga   4140
gacgatgaag aagttgaaat ctgttgtcta cgatgtggga aaaattcggg ctgatcctat   4200
tgtcaataga gctcaaatgg agagatggtg gagaaatcaa agcacagcgg tacaggctaa   4260
ggtagtagca gatgtgagag agttacatga aatagactat tcgtcttaca tgtatatgat   4320
caaatctgac gtgaaaccta agactgattt aacaccgcaa tttgaatact cagctctaca   4380
gactgttgtg tatcacgaga agttgatcaa ctcgttgttc ggtccaattt tcaaagaaat   4440
taatgaacgc aagttggatg ctatgcaacc acattttgtg ttcaacacga gaatgacatc   4500
gagtgattta aacgatcgag tgaagttctt aaatacggaa gcggcttacg actttgttga   4560
gatagacatg tctaaattcg acaagtcggc aaatcgcttc catttacaac tgcagctgga   4620
gatttacagg ttatttgggc tagatgagtg ggcggccttc ctttgggagg tgtcgcacac   4680
tcaaactact gtgagagata ttcaaaatgg tatgatggcg catatttggt accaacaaaa   4740
gagtggagat gctgatactt ataatgcaaa ttcagataga acactgtgtg cactcttgtc   4800
tgaattacca ttggagaaag cagtcatggt tacatatgga ggagatgact cactgattgc   4860
gtttcctaga ggaacgcagt ttgttgatcc gtgtccaaag ttggctacta agtggaattt   4920
cgagtgcaag atttttaagt acgatgtccc aatgtttttgt gggaagttct tgcttaagac   4980
gtcatcgtgt tacgagttcg tgccagatcc ggtaaaagtt ctgacgaagt tggggaaaaa   5040
gagtataaag gatgtgcaac atttagccga gatctacatc tcgctgaatg attccaatag   5100
```

-continued

```
agctcttggg aactacatgg tggtatccaa actgtccgag tctgtttcag accggtattt    5160
gtacaaaggt gattctgttc atgcgctttg tgcgctatgg aagcatatta agagtttttac  5220 agctctgtgt acattattcc gagacgaaaa cgataaggaa ttgaacccgg ctaaggttga    5280
ttggaagaag gcacagagag ctgtgtcaaa cttttacgac tggtaatatg gaagacaagt    5340
cattggtcac cttgaagaag aagactttcg aagtctcaaa attctcaaat ctaggggcca    5400
ttgaattgtt tgtggacggt aggaggaaga gaccgaagta ttttcacaga agaagagaaa    5460
ctgtcctaaa tcatgttggt gggaagaaga gtgaacacaa gttagacgtt tttgaccaaa    5520
gggattacaa aatgattaaa tcttacgcgt ttctaaagat agtaggtgta caactagttg    5580
taacatcaca tctacctgca gatacgcctg ggttcattca aatcgatctg ttggattcga    5640
gacttactga gaaagaaag agaggaaaga ctattcagag attcaaagct cgagcttgcg      5700
ataactgttc agttgcgcag tacaaggttg aatacagtat ttccacacag gagaacgtac    5760
ttgatgtctg gaaggtgggt tgtatttctg agggcgttcc ggtctgtgac ggtacatacc    5820 cttcagtat cgaagtgtcg ctaatatggg ttgctactga ttcgactagg cgcctcaatg     5880
tggaagaact gaacagttcg gattacattg aaggcgattt taccgatcaa gaggttttcg    5940
gtgagttcat gtctttgaaa caagtggaga tgaagacgat tgaggcgaag tacgatggtc    6000
cttacagacc agctactact agacctaagt cattattgtc aagtgaagat gttaagagag    6060
cgtctaataa gaaaaactcg tcttaatgca taaagaaatt tattgtcaat atgacgtgtg    6120
tactcaaggg ttgtgtgaat gaagtcactg ttcttggtca cgagacgtgt agtatcggtc    6180
atgctaacaa attgcgaaag caagttgctg acatggttgg tgtcacacgt aggtgtgcgg    6240
aaaataattg tggatggttt gtctgtgttg ttatcaatga ttttacttttt gatgtgtata   6300 attgttgtgg ccgtagtcac cttgaaaagt gtcgtaaacg tgttgaaaca agaaatcgag    6360
aaatttggaa acaaattcga cgaaatcaag ctgaaaacat gtctgcgaca gctaaaaagt    6420
ctcataattc gaagacctct aagaagaaat tcaaagagga cagagaattt gggacaccaa    6480
aaagattttt aagagatgat gttcctttcg ggattgatcg tttgtttgct ttttgatttt    6540
attttatatt gttatctgtt tctgtgtata gactgtttga gattggcgct tggccgactc    6600
attgtcttac cataggggaa cggactttgt ttgtgttgtt atttttatttg tattttatta    6660 aaattctcaa tgatctgaaa aggcctcgag gctaagagat tattggggggg tgagtaagta   6720 cttttaaagt gatgatggtt acaaaggcaa aaggggtaaa accccctcgcc tacgtaagcg    6780 ttattacgcc c                                                          6791
```

```
<210> SEQ ID NO 9
<211> LENGTH: 11003
<212> TYPE: DNA
<213> ORGANISM: Artificial Sequence
<220> FEATURE:
<223> OTHER INFORMATION: Synthetic plasmid pTRV2
<220> FEATURE:
<221> NAME/KEY: misc_feature
<222> LOCATION: (4824)..(4824)
<223> OTHER INFORMATION: n is a, c, g, or t

<400> SEQUENCE: 9
```

```
ataaaacatt gcacctatgg tgttgccctg gctggggtat gtcagtgatc gcagtagaat     60
gtactaattg acaagttgga gaatacggta gaacgtcctt atccaacaca gcctttatcc    120
ctctccctga cgaggttttt gtcagtgtaa tatttctttt tgaactatcc agcttagtac    180
cgtacgggaa agtgactggt gtgcttatct ttgaaatgtt actttgggtt tcggttccttt   240
```

-continued

```
aggttagtaa gaaagcactt gtcttctcat acaaaggaaa acctgagacg tatcgcttac       300
gaaagtagca atgaaagaaa ggtggtggtt ttaatcgcta ccgcaaaaac gatggggtcg       360
ttttaattaa cttctcctac gcaagcgtct aaacggacgt tggggttttg ctagtttctt       420
tagagaaaac tagctaagtc tttaatgtta tcattagaga tggcataaat ataatacttg       480
tgtctgctga taagatcatt ttaatttgga cgattagact tgttgaacta caggttactg       540
aatcacttgc gctaatcaac atgggagata tgtacgatga atcatttgac aagtcgggcg       600
gtcctgctga cttgatggac gattcttggg tggaatcagt ttcgtggaaa gatctgttga       660
agaagttaca cagcataaaa tttgcactac agtctggtag agatgagatc actgggttac       720
tagcggcact gaatagacag tgtccttatt caccatatga gcagtttcca gataagaagg       780
tgtatttcct tttagactca cgggctaaca gtgctcttgg tgtgattcag aacgcttcag       840
cgttcaagag acgagctgat gagaagaatg cagtggcggg tgttacaaat attcctgcga       900
atccaaacac aacggttacg acgaaccaag ggagtactac tactaccaag gcgaacactg       960
gctcgacttt ggaagaagac ttgtacactt attacaaatt cgatgatgcc tctacagctt      1020
tccacaaatc tctaacttcg ttagagaaca tggagttgaa gagttattac cgaaggaact      1080
ttgagaaagt attcgggatt aagtttggtg gagcagctgc tagttcatct gcaccgcctc      1140
cagcgagtgg aggtccgata cgtcctaatc cctagggatt taaggacgtg aactctgttg      1200
agatctctgt gaaattcaga gggtgggtga taccatattc actgatgcca ttagcgacat      1260
ctaaataggg ctaattgtga ctaatttgag ggaatttcct ttaccattga cgtcagtgtc      1320
gttggtagca tttgagtttc gcaatgcacg aattacttag gaagtggctt gacgacacta      1380
atgtgttatt gttagataat ggtttggtgg tcaaggtacg tagtagagtc ccacatattc      1440
gcacgtatga agtaattgga aagttgtcag tttttgataa ttcactggga gatgatacgc      1500
tgtttgaggg aaaagtagag aacgtatttg tttttatgtt caggcggttc ttgtgtgtca      1560
acaaagatgg acattgttac tcaaggaagc acgatgagct ttattattac ggacgagtgg      1620
acttagattc tgtgagtaag gttaccgaat tctctagaag gcctccatgg ggatccggta      1680
ccgagctcac gcgtctcgag gcccgggcat gtcccgaaga cattaaacta cggttcttta      1740
agtagatccg tgtctgaagt tttaggttca atttaaacct acgagattga cattctcgac      1800
tgatcttgat tgatcggtaa gtcttttgta atttaatttt cttttttgatt ttattttaaa      1860 ttgttatctg tttctgtgta tagactgttt gagatcggcg tttggccgac tcattgtctt      1920 accataggggg aacggacttt gtttgtgttg ttattttatt tgtattttat taaaattctc      1980
aacgatctga aaaagcctcg cggctaagag attgttgggg ggtgagtaag tacttttaaa      2040
gtgatgatgg ttacaaaggc aaaaggggta aaacccctcg cctacgtaag cgttattacg      2100
cccgtctgta cttatatcag tacactgacg agtccctaaa ggacgaaacg ggagaacgct      2160
agccaccacc accaccacca cgtgtgaatt acaggtgacc agctcgaatt ccccgatcg       2220 ttcaaacatt tggcaataaa gtttcttaag attgaatcct gttgccggtc ttgcgatgat      2280
tatcatataa tttctgttga attacgttaa gcatgtaata attaacatgt aatgcatgac      2340
gttatttatg agatgggttt ttatgattag agtcccgcaa ttatacattt aatacgcgat      2400
agaaaacaaa atatagcgcg caaactagga taaattatcg cgcgcggtgt catctatgtt      2460
actagatcgg gaattaaact atcagtgttt gacaggatat attggcgggt aaacctaaga      2520
gaaaagagcg tttattagaa taatcggata tttaaaaggg cgtgaaaagg tttatccgtt      2580
```

-continued

```
cgtccatttg tatgtgcatg ccaaccacag ggttcccctc gggatcaaag tactttgatc   2640
caacccctcc gctgctatag tgcagtcggc ttctgacgtt cagtgcagcc gtcttctgaa   2700
aacgacatgt cgcacaagtc ctaagttacg cgacaggctg ccgccctgcc cttttcctgg   2760
cgttttcttg tcgcgtgttt tagtcgcata aagtagaata cttgcgacta gaaccggaga   2820
cattacgcca tgaacaagag cgccgccgct ggcctgctgg gctatgcccg cgtcagcacc   2880
gacgaccagg acttgaccaa ccaacgggcc gaactcacg  cggccggctg caccaagctg   2940
ttttccgaga agatcaccgg caccaggcgc gaccgcccgg agctggccag gatgcttgac   3000
cacctacgcc ctggcgacgt tgtgacagtg accaggctag accgcctggc ccgcagcacc   3060
cgcgacctac tggacattgc cgagcgcatc caggaggccg gcgcgggcct gcgtagcctg   3120
gcagagccgt gggccgacac caccacgccg gccggccgca tggtgttgac cgtgttcgcc   3180
ggcattgccg agttcgagcg ttccctaatc atcgaccgca cccggagcgg gcgcgaggcc   3240
gccaaggccc gaggcgtgaa gtttggcccc cgccctaccc tcaccccggc acagatcgcg   3300
cacgcccgcg agctgatcga ccaggaaggc cgcaccgtga aagaggcggc tgcactgctt   3360
ggcgtgcatc gctcgaccct gtaccgcgca cttgagcgca gcgaggaagt gacgcccacc   3420
gaggccaggc ggcgcggtgc cttccgtgag gacgcattga ccgaggccga cgccctggcg   3480
gccgccgaga atgaacgcca agaggaacaa gcatgaaacc gcaccaggac ggccaggacg   3540
aaccgttttt cattaccgaa gagatcgagg cggagatgat cgcggccggg tacgtgttcg   3600
agccgcccgc gcacgtctca accgtgcggc tgcatgaaat cctggccggt ttgtctgatg   3660
ccaagctggc ggcctggccg gccagcttgg ccgctgaaga aaccgagcgc cgccgtctaa   3720
aaaggtgatg tgtatttgag taaaacagct tgcgtcatgc ggtcgctgcg tatatgatgc   3780
gatgagtaaa taaacaaata cgcaaggga  acgcatgaag gttatcgctg tacttaacca   3840
gaaaggcggg tcaggcaaga cgaccatcgc aacccatcta gcccgcgccc tgcaactcgc   3900
cggggccgat gttctgttag tcgattccga tccccaggc  agtgcccgcg attgggcggc   3960
cgtgcgggaa gatcaaccgc taaccgttgt cggcatcgac cgcccgacga ttgaccgcga   4020
cgtgaaggcc atcggccggc gcgacttcgt agtgatcgac ggagcgcccc aggcggcgga   4080
cttggctgtg tccgcgatca aggcagccga cttcgtgctg attccggtgc agccaagccc   4140
ttacgacata tgggccaccg ccgacctggt ggagctggtt aagcagcgca ttgaggtcac   4200
ggatggaagg ctacaagcgg cctttgtcgt gtcgcgggcg atcaaaggca cgcgcatcgg   4260
cggtgaggtt gccgaggcgc tggccgggta cgagctgccc attcttgagt cccgtatcac   4320
gcagcgcgtg agctacccag gcactgccgc cgccggcaca accgttcttg aatcagaacc   4380
cgagggcgac gctgcccgcg aggtccaggc gctggccgct gaaattaaat caaaactcat   4440
ttgagttaat gaggtaaaga gaaaatgagc aaaagcacaa acacgctaag tgccggccgt   4500
ccgagcgcac gcagcagcaa ggctgcaacg ttggccagcc tggcagacac gccagccatg   4560
aagcgggtca ctttcagtt  gccggcggag gatcacacca agctgaagat gtacgcggta   4620
cgccaaggca agaccattac cgagctgcta tctgaataca tcgcgcagct accagagtaa   4680
atgagcaaat gaataaatga gtagatgaat tttagcggct aaaggaggcg gcatggaaaa   4740
tcaagaacaa ccaggcaccg acgccgtgga atgccccatg tgtggaggaa cgggcggttg   4800
gccaggcgta agcggctggg ttgnctgccg gccctgcaat ggcactggaa cccccaagcc   4860
cgaggaatcg gcgtgagcgg tcgcaaacca tccggcccgg tacaaatcgg cgcggcgctg   4920
ggtgatgacc tggtggagaa gttgaaggcc gcgcaggccg cccagcggca acgcatcgag   4980
```

```
gcagaagcac gccccggtga atcgtggcaa gcggccgctg atcgaatccg caaagaatcc   5040
cggcaaccgc cggcagccgg tgcgccgtcg attaggaagc cgcccaaggg cgacgagcaa   5100
ccagattttt tcgttccgat gctctatgac gtgggcaccc gcgatagtcg cagcatcatg   5160
gacgtggccg ttttccgtct gtcgaagcgt gaccgacgag ctggcgaggt gatccgctac   5220
gagcttccag acgggcacgt agaggtttcc gcagggccgg ccggcatggc cagtgtgtgg   5280
gattacgacc tggtactgat ggcggtttcc catctaaccg aatccatgaa ccgataccgg   5340
gaagggaagg gagacaagcc cggccgcgtg ttccgtccac acgttgcgga cgtactcaag   5400
ttctgccggc gagccgatgg cggaaagcag aaagacgacc tggtagaaac ctgcattcgg   5460
ttaaacacca cgcacgttgc catgcagcgt acgaagaagg ccaagaacgg ccgcctggtg   5520
acggtatccg agggtgaagc cttgattagc cgctacaaga tcgtaaagag cgaaaccggg   5580
cggccggagt acatcgagat cgagctagct gattggatgt accgcgagat cacagaaggc   5640
aagaacccgg acgtgctgac ggttcacccc gattactttt tgatcgatcc cggcatcggc   5700
cgttttctct accgcctggc acgccgcgcc gcaggcaagg cagaagccag atggttgttc   5760
aagacgatct acgaacgcag tggcagcgcc ggagagttca agaagttctg tttcaccgtg   5820
cgcaagctga tcgggtcaaa tgacctgccg gagtacgatt tgaaggagga ggcggggcag   5880
gctggcccga tcctagtcat gcgctaccgc aacctgatcg agggcgaagc atccgccggt   5940
tcctaatgta cggagcagat gctagggcaa attgccctag caggggaaaa aggtcgaaaa   6000
ggtctctttc ctgtggatag cacgtacatt gggaacccaa agccgtacat tgggaaccgg   6060
aacccgtaca ttgggaaccc aaagccgtac attgggaacc ggtcacacat gtaagtgact   6120
gatataaaag agaaaaaagg cgatttttcc gcctaaaact ctttaaaact tattaaaact   6180
cttaaaaccc gcctggcctg tgcataactg tctggccagc gcacagccga agagctgcaa   6240
aaagcgccta cccttcggtc gctgcgctcc ctacgccccg ccgcttcgcg tcggcctatc   6300
gcggccgctg gccgctcaaa aatggctggc ctacggccag gcaatctacc agggcgcgga   6360
caagccgcgc cgtcgccact cgaccgccgg cgcccacatc aaggcaccct gcctcgcgcg   6420
tttcggtgat gacggtgaaa acctctgaca catgcagctc ccggagacgg tcacagcttg   6480
tctgtaagcg gatgccggga gcagacaagc ccgtcagggc gcgtcagcgg gtgttggcgg   6540
gtgtcggggc gcagccatga cccagtcacg tagcgatagc ggagtgtata ctggcttaac   6600
tatgcggcat cagagcagat tgtactgaga gtgcaccata tgcggtgtga ataccgcac    6660 agatgcgtaa ggagaaaata ccgcatcagg cgctcttccg cttcctcgct cactgactcg   6720
ctgcgctcgg tcgttcggct gcggcgagcg gtatcagctc actcaaaggc ggtaatacgg   6780
ttatccacag aatcagggga taacgcagga agaacatgt gagcaaaagg ccagcaaaag    6840
gccaggaacc gtaaaaaggc cgcgttgctg gcgtttttcc ataggctccg cccccctgac   6900
gagcatcaca aaaatcgacg ctcaagtcag aggtggcgaa acccgacagg actataaaga   6960
taccaggcgt ttccccctgg aagctccctc gtgcgctctc ctgttccgac cctgccgctt   7020
accggatacc tgtccgcctt tctcccttcg ggaagcgtgg cgctttctca tagctcacgc   7080
tgtaggtatc tcagttcggt gtaggtcgtt cgctccaagc tgggctgtgt gcacgaaccc   7140
cccgttcagc ccgaccgctg cgccttatcc ggtaactatc gtcttgagtc caacccggta   7200
agacacgact tatcgccact ggcagcagcc actggtaaca ggattagcag agcgaggtat   7260
gtaggcggtg ctacagagtt cttgaagtgg tggcctaact acggctacac tagaaggaca   7320
```

-continued

```
gtatttggta tctgcgctct gctgaagcca gttaccttcg gaaaaagagt tggtagctct    7380
tgatccggca aacaaaccac cgctggtagc ggtggttttt ttgtttgcaa gcagcagatt    7440
acgcgcagaa aaaaaggatc tcaagaagat cctttgatct tttctacggg gtctgacgct    7500
cagtggaacg aaaactcacg ttaagggctg atgaatcccc taatgatttt tatcaaaatc    7560
attaagttaa ggtagataca catcttgtca tatgatcaaa tggtttcgcc aaaaatcaat    7620
aatcagacaa caaaatgtgc gaactcgata ttttacacga ctctctttac caattctgcc    7680
ccgaattaca cttaaaacga ctcaacagct taacgttggc ttgccacgcc ttacttgact    7740
gtaaaactct cactcttacc gaacttggcc gtaacctgcc aaccaaagcg agaacaaaac    7800
ataacatcaa acgaatcgac cgattgttag gtaatcgtca cctccacaaa gagcgactcg    7860
ctgtataccg ttggcatgct agctttatct gttcgggcaa tacgatgccc attgtacttg    7920
ttgactggtc tgatatccgt gagcaaaaac ggcttatggt attgcgagct tcagtcgcac    7980
tacacggtcg ttctgttact ctttatgaga aagcgttccc gctttcagag caatgttcaa    8040
agaaagctca tgaccaattt ctagccgacc ttgcgagcat tctaccgagt aacaccacac    8100
cgctcattgt cagtgatgct ggctttaaag tgccatggta taaatccgtt gagaagctgg    8160
gttggtactg gttaagtcga gtaagaggaa aagtacaata tgcagaccta ggagcggaaa    8220
actggaaacc tatcagcaac ttacatgata tgtcatctag tcactcaaag actttaggct    8280
ataagaggct gactaaaagc aatccaatct catgccaaat tctattgtat aaatctcgct    8340
ctaaaggccg aaaaaatcag cgctcgacac ggactcattg tcaccacccg tcacctaaaa    8400
tctactcagc gtcggcaaag gagccatgga ttctagcaac taacttacct gttgaaattc    8460
gaacacccaa acaacttgtt aatatctatt cgaagcgaat gcagattgaa gaaaccttcc    8520
gagacttgaa aagtcctgcc tacggactag gcctacgcca tagccgaacg agcagctcag    8580
agcgttttga tatcatgctg ctaatcgccc tgatgcttca actaacatgt tggcttgcgg    8640
gcgttcatgc tcagaaacaa ggttgggaca agcacttcca ggctaacaca gtcagaaatc    8700
gaaacgtact ctcaacagtt cgcttaggca tggaagtttt gcggcattct ggctacacaa    8760
taacaaggga agactcactc gtggctgcaa ccctgcttac tcaaaatcta ttcacacatg    8820
gttacgtttt ggggaaatta tgaggggatc tctcagcgtt aagggatttt ggtcatgcat    8880
tctaggtact aaaacaattc atccagtaaa atataaatatt ttattttctc ccaatcaggc    8940
ttgatcccca gtaagtcaaa aaatagctcg acatactgtt cttccccgat atcctccctg    9000
atcgaccgga cgcagaaggc aatgtcatac cacttgtccg ccctgccgct tctcccaaga    9060
tcaataaagc cacttacttt gccatctttc acaaagatgt tgctgtctcc caggtcgccg    9120
tgggaaaaga caagttcctc ttcgggcttt tccgtcttta aaaaatcata cagctcgcgc    9180
ggatctttaa atggagtgtc ttcttcccag ttttcgcaat ccacatcggc cagatcgtta    9240
ttcagtaagt aatccaattc ggctaagcgg ctgtctaagc tattcgtata gggacaatcc    9300
gatatgtcga tggagtgaaa gagcctgatg cactccgcat acagctcgat aatcttttca    9360
gggctttgtt catcttcata ctcttccgag caaaggacgc catcggcctc actcatgagc    9420
agattgctcc agccatcatg ccgttcaaag tgcaggacct ttggaacagg cagctttcct    9480
tccagccata gcatcatgtc cttttcccgt tccacatcat aggtggtccc tttataccgg    9540
ctgtccgtca ttttttaaata taggttttca ttttctccca ccagcttata taccttagca    9600
ggagacattc cttccgtatc ttttacgcag cggtattttt cgatcagttt tttcaattcc    9660
ggtgatattc tcattttagc catttattat ttccttcctc ttttctacag tatttaaaga    9720
```

-continued

```
taccccaaga agctaattat aacaagacga actccaattc actgttcctt gcattctaaa    9780
accttaaata ccagaaaaca gctttttcaa agttgttttc aaagttggcg tataacatag    9840
tatcgacgga gccgattttg aaaccgcggt gatcacaggc agcaacgctc tgtcatcgtt    9900
acaatcaaca tgctaccctc cgcgagatca tccgtgtttc aaacccggca gcttagttgc    9960
cgttcttccg aatagcatcg gtaacatgag caaagtctgc cgccttacaa cggctctccc   10020
gctgacgccg tcccggactg atgggctgcc tgtatcgagt ggtgattttg tgccgagctg   10080
ccggtcgggg agctgttggc tggctggtgg caggatatat tgtggtgtaa acaaattgac   10140
gcttagacaa cttaataaca cattgcggac gtttttaatg tactgaatta acgccgaatt   10200
aattcctagg ccaccatgtt gggcccggcg cgccaagctt gcatgcctgc aggtcaacat   10260
ggtggagcac gacactctcg tctactccaa gaatatcaaa gatacagtct cagaagacca   10320
gagggctatt gagacttttc aacaaagggt aatatcggga aacctcctcg gattccattg   10380
cccagctatc tgtcacttca tcgaaaggac agtagaaaag gaagatggct tctacaaatg   10440
ccatcattgc gataaaggaa aggctatcgt tcaagatgcc tctaccgaca gtggtcccaa   10500
agatggaccc ccacccacga ggaacatcgt ggaaaaagaa gacgttccaa ccacgtcttc   10560
aaagcaagtg gattgatgtg atggtcaaca tggtggagca cgacactctc gtctactcca   10620
agaatatcaa agatacagtc tcagaagacc agagggctat tgagactttt caacaaaggg   10680
taatatcggg aaacctcctc ggattccatt gcccagctat ctgtcacttc atcgaaagga   10740
cagtagaaaa ggaagatggc ttctacaaat gccatcattg cgataaagga aaggctatcg   10800
ttcaagatgc ctctaccgac agtggtccca agatggaccc ccacccacg aggaacatcg   10860 tggaaaaaga agacgttcca accacgtctt caaagcaagt ggattgatgt gatatctcca   10920
ctgacgtaag ggatgacgca caatcccact atccttcgca agacccttcc tctatataag   10980
gaagttcatt tcatttggag agg                                           11003
```

<210> SEQ ID NO 10
<211> LENGTH: 10644
<212> TYPE: DNA
<213> ORGANISM: Artificial Sequence
<220> FEATURE:
<223> OTHER INFORMATION: Synthetic TuMV-GFP construct

<400> SEQUENCE: 10

```
aaaaaatata aaaactcaac ataacataca caaaacgatt aaagcaaaca caaatctttc      60
aaagcattca agcaatcaaa gattctcaaa tctttcatcg ttatcaaagc aatcaccaac     120
agcaaaccaa atggcagcag ttacattcgc atcagctatc accaacgcca tcaccagcaa     180
accagcactc accggaatgg tgcagtttgg gagtttccca ccaatgccat tgcgatccac     240
caccgtcacc acagtcgcca cttcagtggc gcaacctaaa ctgtacacag tgcagtttgg     300
aagccttgac ccagtagtcg tcaagagtgg agcagggtcc cttgctaagg caacacgcca     360
gcagcctaac gttgaaatag acgttagcct cagtgaagcc gcagctctgg aggttgcgaa     420
acctagatcg aatgccgtgt tgaggatgca cgaggaagca aacaaggaga gagcactctt     480
tttggactgg gaggctagtt tgaagagaag ctcgtatgga attgctgagg acgagaaggt     540
tgtaatgaca actcatggcg tcagcaagat agtgcccaga agttcaaggg caatgaagct     600
aaagcgcgca agggagaggc gtagagcgca gcaaccaatt atattaaagt gggagcccaa     660
attgagcggg atctcaatcg gaggagggct ctctgcgagc gtaatcgaag cagaagaggt     720
```

-continued

```
tcgcacaaag tggccgcttc ataagacacc gtcaatgaag aagaggacgg tgcacagaat    780
atgcaagatg aacgaccaag gagttgacat gttgacacga tccctggtta agattttcaa    840
gactaagagt gccaacattg aatacatcgg aaagaagtcg attaaggtcg atttcatcag    900
aaaagaacga acgaaattcg caagaatcca agtagcacac ttactcggga agagagcaca    960
gcgcgacttg ttaactggaa tggaagaaaa ccattttatt gacattctca gtaagtactc   1020
aggtaacaaa acaaccataa atcctggagt agtttgcgca ggttggagtg gcatagtcgt   1080
tggaaatgga attctaaccc agaaacgaag cagaagtcca tcagaggcct ttgtaattag   1140
aggtgagcac gaaggcaagt tgtacgatgc caggatcaaa gtcacgagga caatgagtca   1200
caagattgtg cactttagtg ccatggcaag taaaggagaa gaacttttca ctggagttgt   1260
cccaattctt gttgaattag atggtgatgt taatgggcac aaattttctg tcagtggaga   1320
gggtgaaggt gatgcaacat acggaaaact tacccttaaa tttatttgca ctactggaaa   1380
actacctgtt ccttggccaa cacttgtcac tactttctct tatggtgttc aatgcttttc   1440 aagatacccca gatcatatga gcggcacga cttcttcaag agcgccatgc ctgagggata   1500
cgtgcaggag aggaccatct ctttcaagga cgacgggaac tacaagacac gtgctgaagt   1560
caagtttgag ggagacaccc tcgtcaacag gatcgagctt aagggaatcg atttcaagga   1620
ggacggaaac atcctcggcc acaagttgga atacaactac aactcccaca cgtatacat    1680 cacggcagac aaacaaaaga atggaatcaa agctaacttc aaaattagac acaacattga   1740
agatggaagc gttcaactag cagaccatta tcaacaaaat actccaattg gcgatggccc   1800 tgtccttta ccagacaacc attacctgtc cacacaatct gccctttcga aagatcccaa    1860
cgaaaagaga gaccacatgg tccttcttga gtttgtaaca gctgctggga ttacacatgg   1920
catggatgaa ctatacaaag gatccgttga ggcttgtgtc tatcaccagg caggtgcagc   1980
gggagccaac ttctggaaag gcttcgacag atgctttctc gcataccgta gtgacaatcg   2040
cgagcataca tgctattcag ggctagatgt cactgagtgc ggcgaggtgg cagcactgat   2100
gtgtttggct atgttcccat gcggaaagat aacctgccct gactgtgtaa cagatagtga   2160
gctatcccaa ggacaagcaa gcggaccatc tatgaagcac aggttgacac agctacgcga   2220
tgtcatcaag tcaagctacc cacgcttcaa gcatgcagtg cagatactag ataggtatga   2280
gcaatcactg agcagtgcaa acgagaacta ccaagatttc gcagaaatcc agagcataag   2340
cgatggagtt gaaaaagctg cattcccaca cgtcaacaag ctaaacgcaa tattgatcaa   2400
aggggccaca gtaacaggag aggaattctc gcaggctacg aagcacttgc tcgagatagc   2460
acgatacctg aagaacagaa ccgagaacat tgagaagggt tcactgaagt cctttcgcaa   2520
caagatttcc cagaaagcgc acatcaaccc aacactaatg tgtgacaacc agctcgatag   2580
aaatggaaat ttcatatggg gtgagagagg ataccatgca aaacgattct tcagcaacta   2640
ctttgaaata atcgatccaa agaaaggcta cacccaatac gagacaagag cggtaccaaa   2700
tgggtcacgg aaacttgcaa tcggcaaact aatagtccca acgaacttcg aagtttttaag   2760 ggaacagatg aaaggcgaac cggtagaacc atacccagta acagtcgagt gtgtgagcaa   2820
gttacagggt gacttcgtcc atgcatgttg ttgtgtcaca acagaatcag cgacccagt    2880 cttgtctgag atcaaaatgc caaccaaaca ccatctagtg attggtaaca gcggtgatcc   2940
aaagtacata gatctccctg agatcgagga gaataaaatg tacatagcga aagaaggtta   3000
ttgttacatc aatatcttcc tagccatgtt ggtaaatgtc aaggagtcgc aggcaaagga   3060
gttcacgaaa gttgttaggg acaaactagt tggcgaactt ggcaagtggc ccactctgtt   3120
```

-continued

```
agatgtagca accgcttgtt atttcctgaa agtattttac ccagacgttg ctaacgccga    3180
attgccacgc atgctagtgg accataagac aaagataatt catgtcgttg attcatatgg    3240
gtcactgtca actggatatc atgtccttaa gacaaacact gtggaacaac tcatcaaatt    3300
cacgagatgt aatttggagt caagcttgaa acactaccgc gttggaggaa cagaatggga    3360
ggacactcat ggatccagca acatagataa tccacagtgg tgcatcaaga ggctcataaa    3420
aggagtctac aaaccaaagc aactgaaaga agacatgttg gcaaacectt tcttaccact    3480 atatgctcta ctgtcaccag gtgtcatcct ggcattttac aatagtggct ctctagagta    3540
cttgatgaac cattacatca gggtggacag caacgtcgcc gttttgttgg tcgttttgaa    3600
atctctagcg aagaaggtgt caactagtca gagtgtgtta gcccagcttc aaatcattga    3660
acgaagtcta ccagaactca tcgaagcaaa ggctaatgtt aatgggccag atgacgcagc    3720
cactcgcgcg tgtaacagat tcatgggcat gcttctgcat atggcagaac caaactggga    3780
gcttgcggat ggtggataca caattctgag ggatcatagc atctccattt tggaaaaaag    3840
ttatctacaa atcttggacg aagcatggaa cgagttaagt tggtcggagc gctgtgctat    3900
aagatactac tcgtcaaagc aagcaatctt tacacagaaa gatttgccaa tgaaaagcga    3960
agccgattta ggcggcagat acagcgtgtc agtcatgtca tcttacgaac ggagtaagca    4020
atgtatgaaa agcgtgcact ctagtatagg taatagatta cgtagtagta tgtcttggac    4080
tagtagcaag gtgtcgaata gtgtgtgtag gactattaac tatttagtac cagatgtgtt    4140
caagtttatg aatgtactcg tttgtatcag cttactaatc aagatgactg ccgaggcgaa    4200
tcacatcgtc accacgcaaa gaaggctcaa actagatgtc gaggagacag agcgcaggaa    4260
aatagaatgg gagcttgcat tccaccatgc cattctgacg cagagtgcag gtcaacaccc    4320
aacgatagac gagttcagag cgtacatcgc cgacaaggca ccacatctaa gtgagcatat    4380
cgagcctgaa gaaaaggcgg tggttcatca agcgaagaga caatccgagc aagaactcga    4440
gcgtataata gcatttgttg cattggtgct catgatgttc gatgcagaac gaagcgactg    4500
tgtcacaaag attctcaaca agcttaaggg actagtcgcc actgtggaac ctacagtcta    4560
ccatcagact ctcaatgata tagaggatga cttgagtgag aggaacctct tcgtcgattt    4620
tgagcttagc agcgatggag atatgctcca acagcttcca gccgaaaaga catttgcctc    4680
atggtggagt catcaactaa gcagaggatt cacaatccca cactacagga cagaagggaa    4740
gttcatgact ttcaccagag caactgccac ggaagtcgcg ggtaaaatag cacacgagag    4800
tgacaaagac atattactaa tgggagcagt aggatcaggt aagtcaactg gcttgccata    4860
tcatctctcc agaaaaggga acgtattact ccttgagccg actcggccac ttgcagaaaa    4920
cgtacacaag cagttgtcgc aggcaccgtt ccatcagaac acaactctta ggatgcgcgg    4980
actaacagca ttcgggtcgg caccaatctc agtgatgacc agtggttttg cactcaatta    5040
ctttgcaaac aacagaatgc gaattgaaga atttgacttt gtcatatttg atgaatgtca    5100
cgttcatgac gccaatgcaa tggcgatgag atgtttgcta catgagtgtg actattctgg    5160
caaaattatc aaagtttcag ccacaccacc aggtcgagaa gttgagttct ccactcaata    5220
ccccgtgtcg ataagcacag aagacacact atcgtttcag gattttgtga acgcacaggg    5280
tagtggaagc aattgtgatg tgatttcaaa aggagacaat atcctcgtgt atgtagcaag    5340
ctacaatgag gtgacgcgc tttcaaaact tctaattgaa agagacttca aagtcacgaa    5400
ggttgatgga agaacgatga aagttggaaa catcgagatc accacaagtg gaacacctag    5460
```

-continued

```
taagaagcac ttcatagttg caaccaacat catagagaac ggtgttactc tagacatcga    5520
tgtggttgct gattttggaa cgaaggtact cccatatctt gatacagaca gcagaatgct    5580
gagcacaact aagacaagca tcaattatgg ggaacgtatc caaaggctag gaagagtcgg    5640
aaggcacaag ccaggtcacg ctctgcgaat aggtcacaca gagaaggggt tgagcgaagt    5700
tccaagttgt attgcaacag aagcagcttt aaagtgcttc acttatgggc ttccagtgat    5760
caccaacaac gtctcgacaa gtattcttgg taatgtaacg gtaaagcagg cacgaacaat    5820
gtctgtattt gagataacac cgttctacac aagccaagtg gtgagatatg atggctccat    5880
gcatccacag gtgcacgcac tcttaaagag attcaaactc agagactctg agattgtttt    5940
gaataaatta gccatacctc accgaggagt gaacgcttgg ctcacagcta gtgagtatgc    6000
acgacttggc gcgaatgttg aagataggcg tgacgttcga attccttta tgtgtcgcga    6060 catcccagaa aaacttcatc tagacatgtg ggatgtgatt gttaaattca aaggtgatgc    6120
aggttttggt cggctttcaa gcgccagtgc gagcaaggta gcttatactc tacagacgga    6180
cgtcaactcc atacagcgaa cagtcactat catagataca ctaatcgctg aggagagaag    6240
gaagcaggaa tacttcaaga cggtaacctc caactgtgtc tcttcttcga acttctcact    6300
gcagagcata acaaatgcga taaaatctcg tatgatgaaa gatcacacgt gcgagaacat    6360
atcagtgctt gaaggagcga agtcacagtt actcgagttt agaaacctga atgctgatca    6420
ctcatttgct acaaaaaccg atggaatatc tcggcatttc atgagtgagt atggagctct    6480
tgaggcagtt caccatcaaa acaccagcga catgagcaaa ttcctcaagc ttaagggcaa    6540
atggaataaa acgctaatca cgcgagatgt gctggtactc tgtggagttc ttggaggtgg    6600
attgtggatg gttattcagc acctgcggtc aaagatgtcc gaacccgtaa cccatgaagc    6660
gaaaggtaag aggcaaaggc agaaactaaa atttcgcaat gcccgagaca acaaaatggg    6720
tagagaagtg tacggagatg atgataccat agagcatttc ttcggtgatg cctacacaaa    6780
gaaagggaag agcaagggta ggacacgtgg tatcggcaca aaaaacagga agttcatcaa    6840
catgtatggg tttgatcctg aagatttctc tgcagttcgt ttcgtggatc cactcacagg    6900
agcgacgttg gacgacaacc cgctcacaga catcacccct gtgcaagagc acttcggcaa    6960
cataagaatg gacttactcg gggaggatga gctggactca aatgaaatac gtgtgaataa    7020
gactattcaa gcctactaca tgaacaataa aacaggcaag gctttgaagg tggatctgac    7080
accacacata cctctcaagg tgtgtgatct tcacgcaacc attgctggat tcccagagcg    7140
agaaaacgag ctgaggcaga ctggaaaggc tcagcccatc aacatagacg aagtgccaag    7200
agctaacaac gaactcgtcc cagtggacca cgagagtaac tccatgttca gagggttgcg    7260
tgactacaac ccaatatcaa acaacatttg tcatctcaca aatgtttcag atggagcatc    7320
aaactcgtta tatggagtcg gtttcggacc actcatatta acgaaccgac acctctttga    7380
gcggaataac ggtgaactcg taataaaatc acgacatggt gagttcgtga ttaaaaacac    7440
aactcagcta cacttgctac cgattccaga cagagatctt ctgctaatcc ggttaccaaa    7500
ggacgtccca cccttttccac agaaattggg tttcaggcaa cctgagaaag gtgaacgaat    7560
ttgcatggtg gggtccaatt tccaaaccaa gagcataacg agtatagtct ctgagactag    7620
tacaataatg ccagtggaga acagtcagtt ttggaaacac tggattagca ctaaagacgg    7680
ccaatgcgga agtccaatgg tgagcacgaa agacgggaaa atactcggat tacacagcct    7740
agcgaacttc cagaactcca tcaattactt tgctgctttc ccagatgatt ttgccgagaa    7800
gtatcttcat accattgaag cacacgagtg ggtcaagcac tggaagtata cactagcgc    7860
```

-continued

```
catcagttgg ggctctttga atatacaagc atcgcaaccg tccggcttgt tcaaagtaag   7920
caagctaatc tcagacctcg acagcacggc agtctacgca caaacccagc agaatcggtg   7980
gatgttcgag cagctcaacg ggaacctaaa agcgatagca cactgcccta gccagcttgt   8040
gacaaagcac acagttaaag gaaaatgtca gatgtttgac ttgtatctca agttgcatga   8100
tgaagcacga gagtatttcc aaccgatgct gggccagtat caaaagagca aactcaatcg   8160
agaagcatat gcaaaggatc ttctgaaata tgcaacgcca atcgaagcag gaaacatcga   8220
ctgtgatctg tttgaaaaga cagttgaaat agtcgtatca gatctgcgag gttatggttt   8280
cgaaacatgc aattatgtca ctgatgagaa tgacatattc gaagctctta acatgaaatc   8340
cgcagttgga gcgttgtata aaggaaagaa gaaggattac ttcgctgagt tcacacccga   8400
gatgaaagaa gaaatactga aacaaagttg tgaacggctc ttcctaggaa agatgggagt   8460
gtggaacggc tcgctgaagg cagagttgcg accactagaa aaagtggaag caaacaaaac   8520
acggacgttt actgccgcac cactagacac actgttgggt ggaaaagttt gcgtggatga   8580
tttcaacaac cagttctatg atcacaacct tagagctcct tggagcgttg gcatgacaaa   8640
gttttattgt ggttgggatc gcttgttgga gtcgttgcca gatggttggg tgtattgcga   8700
tgctgatggc tcacagttcg acagctcgct atcgccatac ttgatcaacg cagtactcaa   8760
catccgctta ggattcatgg aagagtggga cataggggag gtaatgctga gaaatttgta   8820
caccgaaatc gtgtataccc ctatttctac accagatggt acactcgtca agaagttcaa   8880
aggaaacaat agcggacagc catcgactgt tgtggacaac acgctcatgg tcatattggc   8940
agtcaactat tcactcaaga aaagcggaat tccaagtgag ttgcgcgaca gcatcatcag   9000
attcttcgtc aacggagatg atttactgct aagcgtacac ccagagtatg agtatattct   9060
tgacactatg gcagacaact ttcgtgaact gggcctgaag tatactttcg actcaagaac   9120
cagggaaaaa ggagacctct ggtttatgtc gcaccagggg cacaaaagag agggaatctg   9180
gattcccaag ctcgagccag agcgaatagt atcgattcta gaatgggatc ggtcgaaaga   9240
gccatgccat cgactagagg caatctgcgc agcgatgatt gagtcgtggg gatacgacaa   9300
gttaactcac gagatacgca agttctacgc gtggatgatt gaacaagctc catttagctc   9360
cctagcacaa gaagggaaag ctccttacat agcggaaaca gcgctgagga agctctacct   9420
tgataaggaa ccagctcaag aggatctcac ccattatttg caagcaatct ttgaggatta   9480
tgaagatggt gctgaggctt gtgtttatca ccaggcaggt gaaacgcttg atgcaggttt   9540
gacagacgag caaaagcagg cagagaagga gaagaaggag agagagaagg cagaaaagga   9600
acgagagagg caaaagcagt tggcactcaa gaaaggcaag gatgttgcac aagaagaggg   9660
aaaacgcgac aaggaagtaa acgctggaac ctctggaact ttcagtgtac ccagactcaa   9720
gagtctgaca agcaagatgc gcgtgccaag atacgagaaa agagtggctc taaacctcga   9780
tcatctaatc ctatacacgc cggagcagac ggatctatcc aacacacgtt caacgcgaaa   9840
gcagtttgac acatggtttg aaggtgtaat ggctgattac gaactgacgg aggacaaaat   9900
gcaaatcatt ctcaatggtt taatggtctg gtgcattgag aacggaacct ccccgaacat  9960
aaacggaatg tgggtgatga tggacggcga cgatcaggtg gaattcccga tcaaaccgct  10020
cattgaccac gccaaaccca catttaggca gataatggcc catttcagtg acgtagctga  10080
agcgtacatt gaaaagcgta accaagaccg accatacatg ccacgatatg gtcttcagcg  10140
caatttaacc gacatgagct tagctcgata cgcatttgat ttctatgaaa tgacttctag  10200
```

```
gactccaata cgtgcgagag aggcacacat ccagatgaaa gcagcagcac tgcgtggcgc    10260
aaataataat ttgttcggct tggatggaaa cgttggtaca acggtagaga acacggagag    10320
gcatacgacc gaggacgtta atcggaacat gcataactta ctgggcgttc aggggttgtg    10380
aagttgtatg ctggtagact ataagtattt aagtttactc gttagtattc tcgcttatgg    10440
gaaatatgta agtttgttaa agcagccagt gtgactttgt catgtgtgtt gttgttactt    10500
tctgtatttt cgccgaacat tttattggtg ttagcgcatg tagtgaggat cgtcctcgat    10560
tgccttaaca tttgatagga tgcaagggac aaaaaaaaaa aaaaaaaaaa aaaaaaaaaa    10620
aaaaaaaaaa aaaaaaaaaa aaaa                                          10644

<210> SEQ ID NO 11
<211> LENGTH: 2716
<212> TYPE: DNA
<213> ORGANISM: Artificial Sequence
<220> FEATURE:
<223> OTHER INFORMATION: Synthetic plasmid pENTR-AtU6:LbuDR:BsaI

<400> SEQUENCE: 11
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca aatccgctcc cggcggattt gtcctactca ggagagcgtt caccgacaaa     420
caacagataa aacgaaaggc ccagtcttcc gactgagcct ttcgtttat ttgatgcctg      480 gcagttccct actctcgcgt taacgctagc atggatgttt cccagtcac gacgttgtaa      540 aacgacggcc agtcttaagc tcgggcccca ataatgatt ttattttgac tgatagtgac      600
ctgttcgttg caacaaattg atgagcaatg cttttttata atgccaactt tgtacaaaaa     660
agcaggctcc gcggccgccc ccttcacctg atcaaaagtc ccacatcgat caggtgatat     720
atagcagctt agtttatata atgatagagt cgacatagcg attggattta gaccacccca     780
aaaatgaagg ggactaaaac aagagacctt ttttttttga gaccaagggt gggcgcgccg     840
acccagcttt cttgtacaaa gttggcatta taagaaagca ttgcttatca atttgttgca     900
acgaacaggt cactatcagt caaaataaaa tcattatttg ccatccagct gatatcccct     960
atagtgagtc gtattacatg gtcatagctg tttcctggca gctctggccc gtgtctcaaa    1020
atctctgatg ttacattgca caagataaaa atatatcatc atgaacaata aaactgtctg    1080
cttacataaa cagtaataca aggggtgtta tgagccatat tcaacgggaa acgtcgaggc    1140
cgcgattaaa ttccaacatg gatgctgatt tatatgggta taaatgggct cgcgataatg    1200
tcgggcaatc aggtgcgaca atctatcgct tgtatgggaa gcccgatgcg ccagagttgt    1260
ttctgaaaca tggcaaaggt agcgttgcca atgatgttac agatgagatg gtcagactaa    1320
actggctgac ggaatttatg cctcttccga ccatcaagca ttttatccgt actcctgatg    1380
atgcatggtt actcaccact gcgatccccg gaaaaacagc attccaggta ttagaagaat    1440
atcctgattc aggtgaaaat attgttgatg cgctggcagt gttcctgcgc cggttgcatt    1500
cgattcctgt ttgtaattgt cctttttaaca gcgatcgcgt atttcgtctc gctcaggcgc    1560
aatcacgaat gaataacggt ttggttgatg cgagtgattt tgatgacgag cgtaatggct    1620
```

-continued

```
ggcctgttga acaagtctgg aaagaaatgc ataaactttt gccattctca ccggattcag      1680
tcgtcactca tggtgatttc tcacttgata accttatttt tgacgagggg aaattaatag      1740
gttgtattga tgttggacga gtcggaatcg cagaccgata ccaggatctt gccatcctat      1800
ggaactgcct cggtgagttt tctccttcat tacagaaacg gctttttcaa aaatatggta      1860
ttgataatcc tgatatgaat aaattgcagt ttcatttgat gctcgatgag ttttttctaat     1920 cagaattggt taattggttg taacactggc agagcattac gctgacttga cgggacggcg      1980
caagctcatg accaaaatcc cttaacgtga gttacgcgtc gttccactga gcgtcagacc      2040
ccgtagaaaa gatcaaagga tcttcttgag atccttttttt tctgcgcgta atctgctgct     2100
tgcaaacaaa aaaaccaccg ctaccagcgg tggtttgttt gccggatcaa gagctaccaa      2160 ctcttttttcc gaaggtaact ggcttcagca gagcgcagat accaaatact gtccttctag      2220
tgtagccgta gttaggccac cacttcaaga actctgtagc accgcctaca tacctcgctc      2280
tgctaatcct gttaccagtg ctgctgcca gtggcgataa gtcgtgtctt accgggttgg       2340
actcaagacg atagttaccg gataaggcgc agcggtcggg ctgaacgggg ggttcgtgca      2400
cacagcccag cttggagcga acgacctaca ccgaactgag atacctacag cgtgagcatt      2460
gagaaagcgc cacgcttccc gaagggagaa aggcggacag gtatccggta agcggcaggg      2520
tcggaacagg agagcgcacg agggagcttc caggggggaaa cgcctggtat ctttatagtc     2580
ctgtcgggtt cgccacctc tgacttgagc gtcgattttt gtgatgctcg tcaggggggc       2640
ggagcctatg gaaaaacgcc agcaacgcgg ccttttttacg gttcctggcc ttttgctggc     2700
cttttgctca catgtt                                                       2716
```

```
<210> SEQ ID NO 12
<211> LENGTH: 2714
<212> TYPE: DNA
<213> ORGANISM: Artificial Sequence
<220> FEATURE:
<223> OTHER INFORMATION: Synthetic plasmid pENTR-AtU6:LbaDR:BsaI

<400> SEQUENCE: 12
```

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga      120
gcgcccaata cgcaaaccgc ctctccccgc gcgttggccg attcattaat gcagctggca      180
cgacaggttt cccgactgga aagcgggcag tgagcgcaac gcaattaata cgcgtaccgc      240
tagccaggaa gagtttgtag aaacgcaaaa aggccatccg tcaggatggc cttctgctta      300
gtttgatgcc tggcagttta tggcgggcgt cctgcccgcc accctccggg ccgttgcttc      360
acaacgttca aatccgctcc cggcggattt gtcctactca ggagagcgtt caccgacaaa      420
caacagataa aacgaaaggc ccagtcttcc gactgagcct ttcgttttat ttgatgcctg      480
gcagttccct actctcgcgt taacgctagc atggatgttt tcccagtcac gacgttgtaa      540
aacgacggcc agtcttaagc tcgggcccca ataatgatt ttattttgac tgatagtgac       600
ctgttcgttg caacaaattg atgagcaatg ctttttttata atgccaactt tgtacaaaaa     660
agcaggctcc gcggccgccc ccttcacctg atcaaaagtc ccacatcgat caggtgatat      720
atagcagctt agtttatata atgatagagt cgacatagcg attggctgga aagatagcc       780 caagaaagag ggcaataaca gagacctttt tttttgaga ccaagggtgg gcgcgccgac       840
ccagctttct tgtacaaagt tggcattata agaaagcatt gcttatcaat ttgttgcaac      900
```

-continued

```
gaacaggtca ctatcagtca aaataaaatc attatttgcc atccagctga tatcccctat       960
agtgagtcgt attacatggt catagctgtt tcctggcagc tctggcccgt gtctcaaaat      1020
ctctgatgtt acattgcaca agataaaaat atatcatcat gaacaataaa actgtctgct      1080
tacataaaca gtaatacaag gggtgttatg agccatattc aacgggaaac gtcgaggccg      1140
cgattaaatt ccaacatgga tgctgattta tatgggtata aatgggctcg cgataatgtc      1200
gggcaatcag gtgcgacaat ctatcgcttg tatgggaagc ccgatgcgcc agagttgttt      1260
ctgaaacatg gcaaaggtag cgttgccaat gatgttacag atgagatggt cagactaaac      1320
tggctgacgg aatttatgcc tcttccgacc atcaagcatt ttatccgtac tcctgatgat      1380
gcatggttac tcaccactgc gatccccgga aaaacagcat tccaggtatt agaagaatat      1440
cctgattcag gtgaaaatat tgttgatgcg ctggcagtgt tcctgcgccg gttgcattcg      1500
attcctgttt gtaattgtcc ttttaacagc gatcgcgtat ttcgtctcgc tcaggcgcaa      1560
tcacgaatga ataacggttt ggttgatgcg agtgattttg atgacgagcg taatggctgg      1620
cctgttgaac aagtctggaa agaaatgcat aaacttttgc cattctcacc ggattcagtc      1680
gtcactcatg gtgatttctc acttgataac cttatttttg acgaggggaa attaataggt      1740
tgtattgatg ttggacgagt cggaatcgca gaccgatacc aggatcttgc catcctatgg      1800
aactgcctcg gtgagttttc tccttcatta cagaaacggc tttttcaaaa atatggtatt      1860
gataatcctg atatgaataa attgcagttt catttgatgc tcgatgagtt tttctaatca      1920
gaattggtta attggttgta acactggcag agcattacgc tgacttgacg ggacggcgca      1980
agctcatgac caaaatccct taacgtgagt tacgcgtcgt tccactgagc gtcagacccc      2040
gtagaaaaga tcaaaggatc ttcttgagat cctttttttc tgcgcgtaat ctgctgcttg      2100
caaacaaaaa aaccaccgct accagcggtg gtttgtttgc cggatcaaga gctaccaact      2160
ctttttccga aggtaactgg cttcagcaga gcgcagatac caaatactgt ccttctagtg      2220
tagccgtagt taggccacca cttcaagaac tctgtagcac cgcctacata cctcgctctg      2280
ctaatcctgt taccagtggc tgctgccagt ggcgataagt cgtgtcttac cgggttggac      2340
tcaagacgat agttaccgga taaggcgcag cggtcgggct gaacggggggg ttcgtgcaca      2400 cagcccagct tggagcgaac gacctacacc gaactgagat acctacagcg tgagcattga      2460
gaaagcgcca cgcttcccga agggagaaag gcggacaggt atccggtaag cggcagggtc      2520
ggaacaggag agcgcacgag ggagcttcca gggggaaacg cctggtatct ttatagtcct      2580
gtcgggtttc gccacctctg acttgagcgt cgatttttgt gatgctcgtc aggggggcgg      2640
agcctatgga aaaacgccag caacgcggcc tttttacggt tcctggcctt ttgctggcct      2700
tttgctcaca tgtt                                                         2714
```

```
<210> SEQ ID NO 13
<211> LENGTH: 3034
<212> TYPE: DNA
<213> ORGANISM: Artificial Sequence
<220> FEATURE:
<223> OTHER INFORMATION: Synthetic plasmid pCR8:PEBV:LbuDR:BsaI

<400> SEQUENCE: 13
agggcgaatt cgacccagct ttcttgtaca aagttggcat tataaaaaat aattgctcat        60
caatttgttg caacgaacag gtcactatca gtcaaaataa aatcattatt tgccatccag       120
ctgatatccc ctatagtgag tcgtattaca tggtcatagc tgtttcctgg cagctctggc       180
ccgtgtctca aaatctctga tgttacattg cacaagataa aaatatatca tcatgcctcc       240
```

```
tctagaccag ccaggacaga aatgcctcga cttcgctgct gcccaaggtt gccgggtgac    300
gcacaccgtg gaaacggatg aaggcacgaa cccagtggac ataagcctgt tcggttcgta    360
agctgtaatg caagtagcgt atgcgctcac gcaactggtc cagaaccttg accgaacgca    420
gcggtggtaa cggcgcagtg gcggttttca tggcttgtta tgactgtttt tttggggtac    480
agtctatgcc tcgggcatcc aagcagcaag cgcgttacgc cgtgggtcga tgtttgatgt    540
tatggagcag caacgatgtt acgcagcagg gcagtcgccc taaaacaaag ttaaacatca    600
tgagggaagc ggtgatcgcc gaagtatcga ctcaactatc agaggtagtt ggcgtcatcg    660
agcgccatct cgaaccgacg ttgctggccg tacatttgta cggctccgca gtggatggcg    720
gcctgaagcc acacagtgat attgatttgc tggttacggt gaccgtaagg cttgatgaaa    780
caacgcggcg agctttgatc aacgaccttt tggaaacttc ggcttcccct ggagagagcg    840
agattctccg cgctgtagaa gtcaccattg ttgtgcacga cgacatcatt ccgtggcgtt    900
atccagctaa gcgcgaactg caatttggag aatggcagcg caatgacatt cttgcaggta    960
tcttcgagcc agccacgatc gacattgatc tggctatctt gctgacaaaa gcaagagaac   1020
atagcgttgc cttggtaggt ccagcggcgg aggaactctt tgatccggtt cctgaacagg   1080
atctatttga ggcgctaaat gaaaccttaa cgctatggaa ctcgccgccc gactgggctg   1140
gcgatgagcg aaatgtagtg cttacgttgt cccgcatttg gtacagcgca gtaaccggca   1200
aaatcgcgcc gaaggatgtc gctgccgact gggcaatgga gcgcctgccg gcccagtatc   1260
agcccgtcat acttgaagct agacaggctt atcttggaca agaagaagat cgcttggcct   1320
cgcgcgcaga tcagttggaa gaatttgtcc actacgtgaa aggcgagatc accaaggtag   1380
tcggcaaata accctcgagc cacccatgac caaaatccct taacgtgagt tacgcgtcgt   1440
tccactgagc gtcagacccc gtagaaaaga tcaaaggatc ttcttgagat cctttttttc   1500
tgcgcgtaat ctgctgcttg caaacaaaaa aaccaccgct accagcggtg gtttgtttgc   1560
cggatcaaga gctaccaact cttttttccga aggtaactgg cttcagcaga gcgcagatac   1620
caaatactgt ccttctagtg tagccgtagt taggccacca cttcaagaac tctgtagcac   1680
cgcctacata cctcgctctg ctaatcctgt taccagtggc tgctgccagt ggcgataagt   1740
cgtgtcttac cgggttggac tcaagacgat agttaccgga taaggcgcag cggtcgggct   1800
gaacgggggg ttcgtgcaca cagcccagct tggagcgaac gacctacacc gaactgagat   1860
acctacagcg tgagcattga gaaagcgcca cgcttcccga agggagaaag gcggacaggt   1920
atccggtaag cggcagggtc ggaacaggag agcgcacgag ggagcttcca gggggaaacg   1980
cctggtatct ttatagtcct gtcgggtttc gccacctctg acttgagcgt cgatttttgt   2040
gatgctcgtc aggggggcgg agcctatgga aaaacgccag caacgcggcc ttttttacggt   2100 tcctggcctt ttgctggcct tttgctcaca tgttctttcc tgcgttatcc cctgattctg   2160
tggataaccg tattaccgcc tttgagtgag ctgataccgc tcgccgcagc cgaacgaccg   2220
agcgcagcga gtcagtgagc gaggaagcgg aagagcgccc aatacgcaaa ccgcctctcc   2280
ccgcgcgttg gccgattcat taatgcagct ggcacgacag gtttcccgac tggaaagcgg   2340
gcagtgagcg caacgcaatt aatacgcgta ccgctagcca ggaagagttt gtagaaacgc   2400
aaaaaggcca tccgtcagga tggccttctg cttagtttga tgcctggcag tttatggcgg   2460
gcgtcctgcc cgccacccctc cgggccgttg cttcacaacg ttcaaatccg ctcccggcgg   2520
atttgtccta ctcaggagag cgttcaccga caaacaacag ataaaacgaa aggcccagtc   2580
```

-continued

```
ttccgactga gcctttcgtt ttatttgatg cctggcagtt ccctactctc gcgttaacgc      2640
tagcatggat gttttcccag tcacgacgtt gtaaaacgac ggccagtctt aagctcgggc      2700
cccaaataat gattttattt tgactgatag tgacctgttc gttgcaacaa attgatgagc      2760
aatgcttttt tataatgcca actttgtaca aaaaagcagg ctccgaattc gccctaattc      2820
gagcatcttg ttctggggtt tcacactatc tttagagaaa gtgttaagtt aattaagtta      2880
tcttaattaa gagcataatt atactgattt gtctctcgtt gatagagtct atcattctgt      2940
tactaaaaat ttgacaactc ggtttgctga cctactggtt actgtatcac ttacccgagt      3000
taacgagaac aagagacctt ttttttttga gacc                                  3034

<210> SEQ ID NO 14
<211> LENGTH: 75
<212> TYPE: DNA
<213> ORGANISM: Artificial Sequence
<220> FEATURE:
<223> OTHER INFORMATION: Synthetic AtU6 promoter

<400> SEQUENCE: 14
tgatcaaaag tcccacatcg atcaggtgat atatagcagc ttagtttata taatgataga       60
gtcgacatag cgatt                                                       75

<210> SEQ ID NO 15
<211> LENGTH: 192
<212> TYPE: DNA
<213> ORGANISM: Artificial Sequence
<220> FEATURE:
<223> OTHER INFORMATION: Synthetic PEBV promoter

<400> SEQUENCE: 15
aattcgagca tcttgttctg gggtttcaca ctatctttag agaaagtgtt aagttaatta       60
agttatctta attaagagca taattatact gatttgtctc tcgttgatag agtctatcat      120
tctgttacta aaaatttgac aactcggttt gctgacctac tggttactgt atcacttacc      180
cgagttaacg ag                                                         192

<210> SEQ ID NO 16
<211> LENGTH: 60
<212> TYPE: DNA
<213> ORGANISM: Artificial Sequence
<220> FEATURE:
<223> OTHER INFORMATION: Synthetic Lbu crRNA cloning backbone

<400> SEQUENCE: 16
gatttagacc accccaaaaa tgaaggggac taaaacaaga gacctttttt ttttgagacc       60

<210> SEQ ID NO 17
<211> LENGTH: 57
<212> TYPE: DNA
<213> ORGANISM: Artificial Sequence
<220> FEATURE:
<223> OTHER INFORMATION: Synthetic Lba crRNA cloning backbone

<400> SEQUENCE: 17
gctggagaag atagcccaag aaagagggca ataacggtct cgtaactttt tgagacc          57

<210> SEQ ID NO 18
<211> LENGTH: 28
<212> TYPE: DNA
<213> ORGANISM: Artificial Sequence
<220> FEATURE:
<223> OTHER INFORMATION: Synthetic guide sequence
```

-continued

<400> SEQUENCE: 18
gtttctgcct ttgcctctta cctttcgc                                                          28

<210> SEQ ID NO 19
<211> LENGTH: 28
<212> TYPE: DNA
<213> ORGANISM: Artificial Sequence
<220> FEATURE:
<223> OTHER INFORMATION: Synthetic guide sequence

<400> SEQUENCE: 19
ctgggaaatc ttgttgcgaa aggacttc                                                          28

<210> SEQ ID NO 20
<211> LENGTH: 28
<212> TYPE: DNA
<213> ORGANISM: Artificial Sequence
<220> FEATURE:
<223> OTHER INFORMATION: Synthetic guide sequence

<400> SEQUENCE: 20
ttgtgtttgc tttaatcgtt ttgtgtat                                                          28

<210> SEQ ID NO 21
<211> LENGTH: 164
<212> TYPE: DNA
<213> ORGANISM: Artificial Sequence
<220> FEATURE:
<223> OTHER INFORMATION: Synthetic guide sequence

<400> SEQUENCE: 21
taacgtttct gcctttgcct cttacctttc gcgctggaga agatagccca agaaagaggg        60
caataacctg ggaaatcttg ttgcgaaagg acttcgctgg agaagatagc ccaagaaaga       120
gggcaataac ttgtgtttgc tttaatcgtt ttgtgtattt tttt                       164

<210> SEQ ID NO 22
<211> LENGTH: 168
<212> TYPE: DNA
<213> ORGANISM: Artificial Sequence
<220> FEATURE:
<223> OTHER INFORMATION: Synthetic guide sequence

<400> SEQUENCE: 22
aacagtttct gcctttgcct cttacctttc gcgatttaga ccaccccaaa aatgaagggg        60
actaaaacac tgggaaatct tgttgcgaaa ggacttcgat ttagaccacc ccaaaaatga       120
aggggactaa acattgtgt ttgctttaat cgttttgtgt attttttt                     168

<210> SEQ ID NO 23
<211> LENGTH: 28
<212> TYPE: DNA
<213> ORGANISM: Artificial Sequence
<220> FEATURE:
<223> OTHER INFORMATION: Synthetic guide sequence

<400> SEQUENCE: 23
cctttcggta cttcgtccac aaacacaa                                                          28

<210> SEQ ID NO 24
<211> LENGTH: 28
<212> TYPE: DNA
<213> ORGANISM: Artificial Sequence
<220> FEATURE:

<223> OTHER INFORMATION: Synethetic guide sequence

<400> SEQUENCE: 24
gtccaatttg gggcatttta ttgaacaa                                         28

<210> SEQ ID NO 25
<211> LENGTH: 28
<212> TYPE: DNA
<213> ORGANISM: Artificial Sequence
<220> FEATURE:
<223> OTHER INFORMATION: Synthetic guide sequence

<400> SEQUENCE: 25
tcgaaagctc gtcagggttt atgaagtt                                         28

<210> SEQ ID NO 26
<211> LENGTH: 28
<212> TYPE: DNA
<213> ORGANISM: Artificial Sequence
<220> FEATURE:
<223> OTHER INFORMATION: Synthetic guide sequence

<400> SEQUENCE: 26
gaagtaactc gtaatcctgt acaatagc                                         28

<210> SEQ ID NO 27
<211> LENGTH: 169
<212> TYPE: DNA
<213> ORGANISM: Artificial Sequence
<220> FEATURE:
<223> OTHER INFORMATION: Synthetic guide sequence

<400> SEQUENCE: 27
aacagtccaa tttggggcat tttattgaac aagatttaga ccaccccaaa aatgaagggg      60
actaaaacat cgaaagctcg tcagggttta tgaagttgat ttagaccacc ccaaaaatga     120
aggggactaa aacagaagta actcgtaatc ctgtacaata gcttttttt                 169

<210> SEQ ID NO 28
<211> LENGTH: 169
<212> TYPE: DNA
<213> ORGANISM: Artificial Sequence
<220> FEATURE:
<223> OTHER INFORMATION: Synthetic guide sequence

<400> SEQUENCE: 28
aacacctttt gactcaatat gttccacaat cggatttaga ccaccccaaa aatgaagggg      60
actaaaacaa cagacatgtc agcgtacaca ctgagcagat ttagaccacc ccaaaaatga     120
aggggactaa aacagggaaa agcttcgcta gttccttcat tgtttttttt                169

<210> SEQ ID NO 29
<211> LENGTH: 28
<212> TYPE: DNA
<213> ORGANISM: Artificial Sequence
<220> FEATURE:
<223> OTHER INFORMATION: Synthetic nontargeting control guide

<400> SEQUENCE: 29
cctttcggta cttcgtccac aaacacaa                                         28

<210> SEQ ID NO 30
<211> LENGTH: 166
<212> TYPE: DNA
<213> ORGANISM: Artificial Sequence -continued

```
<220> FEATURE:
<223> OTHER INFORMATION: Synthetic guide sequence

<400> SEQUENCE: 30
aacagtccgc tttggggcat tttattgaac aagatttaga ccaccccaaa aatgaagggg      60
actaaaacat cgagcgctcg tcagggttta tgaagttgat ttagaccacc ccaaaaatga     120
aggggactaa aacagaagcg actcgtaatc ctgtacaata gctttt                    166

<210> SEQ ID NO 31
<211> LENGTH: 166
<212> TYPE: DNA
<213> ORGANISM: Artificial Sequence
<220> FEATURE:
<223> OTHER INFORMATION: Synthetic guide sequence

<400> SEQUENCE: 31
aacagtccaa ttttaggcat tttattgaac aagatttaga ccaccccaaa aatgaagggg      60
actaaaacat cgaaagctat tcagggttta tgaagttgat ttagaccacc ccaaaaatga     120
aggggactaa aacagaagta acttataatc ctgtacaata gctttt                    166

<210> SEQ ID NO 32
<211> LENGTH: 166
<212> TYPE: DNA
<213> ORGANISM: Artificial Sequence
<220> FEATURE:
<223> OTHER INFORMATION: Synthetic guide sequence

<400> SEQUENCE: 32
aacagtccaa tttggggcat tttagcgaac aagatttaga ccaccccaaa aatgaagggg      60
actaaaacat cgaagctcgt cagggttttc ggaagttgat ttagaccacc ccaaaaatga     120
aggggactaa aacagaagta actcgtaatc ctgttgaata gctttt                    166

<210> SEQ ID NO 33
<211> LENGTH: 117
<212> TYPE: DNA
<213> ORGANISM: Artificial Sequence
<220> FEATURE:
<223> OTHER INFORMATION: Synthetic nontargeting guide control

<400> SEQUENCE: 33
aacacctttc ggtacttcgt ccacaaacac aacgggaacc attcaaaaca gcatagcaag      60
ttaaaataag gctagtccgt tatcaacttg aaaaagtggc accgagtcgg tgctttt        117

<210> SEQ ID NO 34
<211> LENGTH: 117
<212> TYPE: DNA
<213> ORGANISM: Artificial Sequence
<220> FEATURE:
<223> OTHER INFORMATION: Synthetic guide sequence

<400> SEQUENCE: 34
aacagaagta actcgtaatc ctgtacaata gccgggaacc attcaaaaca gcatagcaag      60
ttaaaataag gctagtccgt tatcaacttg aaaaagtggc accgagtcgg tgctttt        117

<210> SEQ ID NO 35
<211> LENGTH: 117
<212> TYPE: DNA
<213> ORGANISM: Artificial Sequence
<220> FEATURE:
<223> OTHER INFORMATION: Synthetic guide sequence
```

-continued

```
<400> SEQUENCE: 35
aacagtactt agtggaattg cagaagattt ggcgggaacc attcaaaaca gcatagcaag      60
ttaaaataag gctagtccgt tatcaacttg aaaaagtggc accgagtcgg tgctttt       117

<210> SEQ ID NO 36
<211> LENGTH: 165
<212> TYPE: DNA
<213> ORGANISM: Artificial Sequence
<220> FEATURE:
<223> OTHER INFORMATION: Synthetic guide sequence

<400> SEQUENCE: 36
aacataagct gaactacctt ggactctcaa gtgatttaga ccaccccaaa aatgaagggg      60
actaaaacat tgaaagttcg tcagggttta taaagttgat ttagacaccc caaaaatgaa     120
ggggactaaa acacaagtaa ctcataatcc tgtacaatag ctttt                    165

<210> SEQ ID NO 37
<211> LENGTH: 28
<212> TYPE: DNA
<213> ORGANISM: Artificial Sequence
<220> FEATURE:
<223> OTHER INFORMATION: Synthetic nontargeting control guide

<400> SEQUENCE: 37
cctttcggta cttcgtccac aaacacaa                                        28

<210> SEQ ID NO 38
<211> LENGTH: 24
<212> TYPE: DNA
<213> ORGANISM: Artificial Sequence
<220> FEATURE:
<223> OTHER INFORMATION: Forward primer

<400> SEQUENCE: 38
ggactggatg agaaagcaag gtgt                                            24

<210> SEQ ID NO 39
<211> LENGTH: 24
<212> TYPE: DNA
<213> ORGANISM: Artificial Sequence
<220> FEATURE:
<223> OTHER INFORMATION: Reverse primer

<400> SEQUENCE: 39
atcgaaagct cgtcagggtt tatg                                            24

<210> SEQ ID NO 40
<211> LENGTH: 21
<212> TYPE: DNA
<213> ORGANISM: Artificial Sequence
<220> FEATURE:
<223> OTHER INFORMATION: Forward primer

<400> SEQUENCE: 40
agctttacct cccaagtcat c                                               21

<210> SEQ ID NO 41
<211> LENGTH: 20
<212> TYPE: DNA
<213> ORGANISM: Artificial Sequence
<220> FEATURE:
<223> OTHER INFORMATION: Reverse primer

<400> SEQUENCE: 41
```

-continued

```
agaacgcctg tcaatcttgg                                       20

<210> SEQ ID NO 42
<211> LENGTH: 23
<212> TYPE: DNA
<213> ORGANISM: Artificial Sequence
<220> FEATURE:
<223> OTHER INFORMATION: Forward primer

<400> SEQUENCE: 42
gaaggagaag aaggagagag aga                                   23

<210> SEQ ID NO 43
<211> LENGTH: 21
<212> TYPE: DNA
<213> ORGANISM: Artificial Sequence
<220> FEATURE:
<223> OTHER INFORMATION: Reverse primer

<400> SEQUENCE: 43
cagaggttcc agcgtttact t                                     21

<210> SEQ ID NO 44
<211> LENGTH: 22
<212> TYPE: DNA
<213> ORGANISM: Artificial Sequence
<220> FEATURE:
<223> OTHER INFORMATION: Forward primer

<400> SEQUENCE: 44
tgaggacgag aaggttgtaa tg                                    22

<210> SEQ ID NO 45
<211> LENGTH: 18
<212> TYPE: DNA
<213> ORGANISM: Artificial Sequence
<220> FEATURE:
<223> OTHER INFORMATION: Reverse primer

<400> SEQUENCE: 45
attggttgct gcgctcta                                         18

<210> SEQ ID NO 46
<211> LENGTH: 22
<212> TYPE: DNA
<213> ORGANISM: Artificial Sequence
<220> FEATURE:
<223> OTHER INFORMATION: Forward primer

<400> SEQUENCE: 46
ccgaacaagg aacaagtgaa ag                                    22

<210> SEQ ID NO 47
<211> LENGTH: 22
<212> TYPE: DNA
<213> ORGANISM: Artificial Sequence
<220> FEATURE:
<223> OTHER INFORMATION: Reverse primer

<400> SEQUENCE: 47
gtcctcatct tcaatgccag ta                                    22

<210> SEQ ID NO 48
<211> LENGTH: 21
<212> TYPE: DNA
```

-continued

```
<213> ORGANISM: Artificial Sequence
<220> FEATURE:
<223> OTHER INFORMATION: Forward primer

<400> SEQUENCE: 48
cgcctcagag ctgtaaacat a                                      21

<210> SEQ ID NO 49
<211> LENGTH: 20
<212> TYPE: DNA
<213> ORGANISM: Artificial Sequence
<220> FEATURE:
<223> OTHER INFORMATION: Reverse primer

<400> SEQUENCE: 49
ctccgaacca gccgaataaa                                        20

<210> SEQ ID NO 50
<211> LENGTH: 25
<212> TYPE: DNA
<213> ORGANISM: Artificial Sequence
<220> FEATURE:
<223> OTHER INFORMATION: Forward primer

<400> SEQUENCE: 50
ggtcacaaac cgatattgct ggagg                                  25

<210> SEQ ID NO 51
<211> LENGTH: 28
<212> TYPE: DNA
<213> ORGANISM: Artificial Sequence
<220> FEATURE:
<223> OTHER INFORMATION: Reverse primer

<400> SEQUENCE: 51
acagacatgt cagcgtacac actgagca                               28

<210> SEQ ID NO 52
<211> LENGTH: 27
<212> TYPE: DNA
<213> ORGANISM: Artificial Sequence
<220> FEATURE:
<223> OTHER INFORMATION: Forward primer

<400> SEQUENCE: 52
gctgaaaata tttaggcagt tgaactc                                27

<210> SEQ ID NO 53
<211> LENGTH: 23
<212> TYPE: DNA
<213> ORGANISM: Artificial Sequence
<220> FEATURE:
<223> OTHER INFORMATION: Reverse primer

<400> SEQUENCE: 53
ggaacccttt aagttcgtca gct                                    23

<210> SEQ ID NO 54
<211> LENGTH: 24
<212> TYPE: DNA
<213> ORGANISM: Artificial Sequence
<220> FEATURE:
<223> OTHER INFORMATION: Forward primer

<400> SEQUENCE: 54
gttcgggatt atgcgaaagt gacc                                   24
```

-continued

```
<210> SEQ ID NO 55
<211> LENGTH: 23
<212> TYPE: DNA
<213> ORGANISM: Artificial Sequence
<220> FEATURE:
<223> OTHER INFORMATION: Reverse primer

<400> SEQUENCE: 55
acggaaaacc tccagttcct cgc                                            23

<210> SEQ ID NO 56
<211> LENGTH: 34
<212> TYPE: DNA
<213> ORGANISM: Artificial Sequence
<220> FEATURE:
<223> OTHER INFORMATION: Reverse primer

<400> SEQUENCE: 56
gactagcgaa ttcaattcga gcatcttgtt ctgg                               34

<210> SEQ ID NO 57
<211> LENGTH: 29
<212> TYPE: DNA
<213> ORGANISM: Artificial Sequence
<220> FEATURE:
<223> OTHER INFORMATION: Forward primer

<400> SEQUENCE: 57
cagtacaacg cgtctgggtc gaattcgcc                                     29

<210> SEQ ID NO 58
<211> LENGTH: 85
<212> TYPE: DNA
<213> ORGANISM: Artificial Sequence
<220> FEATURE:
<223> OTHER INFORMATION: Synthetic nanostring probe

<400> SEQUENCE: 58
cgtgtatagg attagatgat cgaggtttag agccactctt ttctcgtatc caacagccac   60
tttttttcca aattttgcaa gagcc                                         85

<210> SEQ ID NO 59
<211> LENGTH: 63
<212> TYPE: DNA
<213> ORGANISM: Artificial Sequence
<220> FEATURE:
<223> OTHER INFORMATION: Synthetic nanostring probe

<400> SEQUENCE: 59
cgaaagccat gacctccgat cactccgcgt tgaacgtgtg ttggatagat ccgtctgctc   60
cgg                                                                 63

<210> SEQ ID NO 60
<211> LENGTH: 85
<212> TYPE: DNA
<213> ORGANISM: Artificial Sequence
<220> FEATURE:
<223> OTHER INFORMATION: Synthetic nanostring probe

<400> SEQUENCE: 60
cgaaaggact tcagtgaacc cttctcaatg ttctcggttc tgttcttcag caccgtgtgg   60
acggcaactc agagataacg catat                                         85
```

```
<210> SEQ ID NO 61
<211> LENGTH: 75
<212> TYPE: DNA
<213> ORGANISM: Artificial Sequence
<220> FEATURE:
<223> OTHER INFORMATION: Synthetic nanostring probe

<400> SEQUENCE: 61
cgaaagccat gacctccgat cactctgtca cacattagtg ttgggttgat gtgcgctttc    60
tgggaaatct tgttg                                                     75

<210> SEQ ID NO 62
<211> LENGTH: 85
<212> TYPE: DNA
<213> ORGANISM: Artificial Sequence
<220> FEATURE:
<223> OTHER INFORMATION: Synthetic nanostring probe

<400> SEQUENCE: 62
cgcagttacg cacataggtg tccagcttgt ttaacagctt attttcgata catcctcttc    60
ttttcttggt gttgagaaga tgctc                                         85

<210> SEQ ID NO 63
<211> LENGTH: 75
<212> TYPE: DNA
<213> ORGANISM: Artificial Sequence
<220> FEATURE:
<223> OTHER INFORMATION: Synthetic nanostring probe

<400> SEQUENCE: 63
cgaaagccat gacctccgat cactcgaagt ctgaagtggc tatctccccg tcttgcaaat    60
aatagttgta cttgc                                                    75

<210> SEQ ID NO 64
<211> LENGTH: 85
<212> TYPE: DNA
<213> ORGANISM: Artificial Sequence
<220> FEATURE:
<223> OTHER INFORMATION: Synthetic nanostring probe

<400> SEQUENCE: 64
ttgggtaagc cccaaagaat atgtgcaacc cagtctcgta ccaatctcca caaagacgcc    60
tatcttccag tttgatcggg aaact                                         85

<210> SEQ ID NO 65
<211> LENGTH: 75
<212> TYPE: DNA
<213> ORGANISM: Artificial Sequence
<220> FEATURE:
<223> OTHER INFORMATION: Synthetic nanostring probe

<400> SEQUENCE: 65
cgaaagccat gacctccgat cactcccact gcaaccgatc gttaatccct agttctccaa    60
acaggttctg catat                                                    75

<210> SEQ ID NO 66
<211> LENGTH: 85
<212> TYPE: DNA
<213> ORGANISM: Artificial Sequence
<220> FEATURE:
<223> OTHER INFORMATION: Synthetic nanostring probe

<400> SEQUENCE: 66
```

```
cagggacggt tccaatgcca ccaatcttgt aaacatcctg aagtggaaga ccaatttggt    60
tttactcccc tcgattatgc ggagt                                           85

<210> SEQ ID NO 67
<211> LENGTH: 60
<212> TYPE: DNA
<213> ORGANISM: Artificial Sequence
<220> FEATURE:
<223> OTHER INFORMATION: Synthetic nanostring probe

<400> SEQUENCE: 67
cgaaagccat gacctccgat cactcaccag gcttgagcac accagtctcc acacgaccaa    60

<210> SEQ ID NO 68
<211> LENGTH: 79
<212> TYPE: DNA
<213> ORGANISM: Artificial Sequence
<220> FEATURE:
<223> OTHER INFORMATION: Synthetic nanostring probe

<400> SEQUENCE: 68
tcccatcagg cctaatcaag gtattgactt tctttgtctg gatgcgaacc taactcctcg    60
ctacattcct attgttttc                                                  79

<210> SEQ ID NO 69
<211> LENGTH: 75
<212> TYPE: DNA
<213> ORGANISM: Artificial Sequence
<220> FEATURE:
<223> OTHER INFORMATION: Synthetic nanostring probe

<400> SEQUENCE: 69
cgaaagccat gacctccgat cactcaacgt ccaatgcatc gtagtcagga gtcaacctca    60
catatgcttt cttcg                                                      75

<210> SEQ ID NO 70
<211> LENGTH: 85
<212> TYPE: DNA
<213> ORGANISM: Artificial Sequence
<220> FEATURE:
<223> OTHER INFORMATION: Synthetic nanostring probe

<400> SEQUENCE: 70
cttgccaagt gcagcacaac cctcaacagc taataaacgt acagaatcct cagataaggt    60
tgttattgtg gaggatgtta ctaca                                           85

<210> SEQ ID NO 71
<211> LENGTH: 75
<212> TYPE: DNA
<213> ORGANISM: Artificial Sequence
<220> FEATURE:
<223> OTHER INFORMATION: Synthetic nanostring probe

<400> SEQUENCE: 71
cgaaagccat gacctccgat cactcttgac aatgacaggc aggatgtgtg caacacaatc    60
ctgtggctcc aacag                                                      75

<210> SEQ ID NO 72
<211> LENGTH: 28
<212> TYPE: DNA
<213> ORGANISM: Artificial Sequence
<220> FEATURE:
```

-continued

<223> OTHER INFORMATION: Synthetic guide sequence

<400> SEQUENCE: 72
taacgaatct ggagctgaat tatccatg                                            28

<210> SEQ ID NO 73
<211> LENGTH: 28
<212> TYPE: DNA
<213> ORGANISM: Artificial Sequence
<220> FEATURE:
<223> OTHER INFORMATION: Synthetic guide sequence

<400> SEQUENCE: 73
ctacaagttc cgagacgttt cggctcta                                            28

<210> SEQ ID NO 74
<211> LENGTH: 28
<212> TYPE: DNA
<213> ORGANISM: Artificial Sequence
<220> FEATURE:
<223> OTHER INFORMATION: Synthetic guide sequence

<400> SEQUENCE: 74
aggagctgca ttttgttagc aaaagcaa                                            28

<210> SEQ ID NO 75
<211> LENGTH: 166
<212> TYPE: DNA
<213> ORGANISM: Artificial Sequence
<220> FEATURE:
<223> OTHER INFORMATION: Synthetic guide sequence

<400> SEQUENCE: 75
aacataacga atctggagct gaattatcca tggatttaga ccaccccaaa aatgaagggg      60
actaaaacac tacaagttcc gagacgtttc ggctctagat ttagaccacc ccaaaaatga     120
aggggactaa acaaggagc tgcattttgt tagcaaaagc aatttt                     166

<210> SEQ ID NO 76
<211> LENGTH: 168
<212> TYPE: DNA
<213> ORGANISM: Artificial Sequence
<220> FEATURE:
<223> OTHER INFORMATION: Synthetic nontargeting control guide

<400> SEQUENCE: 76
aacagtttct gcctttgcct cttacctttc gcgatttaga ccaccccaaa aatgaagggg      60
actaaaacac tgggaaatct tgttgcgaaa ggacttcgat ttagaccacc ccaaaaatga     120
aggggactaa acattgtgt ttgctttaat cgttttgtgt attttttt                   168

The invention claimed is:

1. A system comprising a short multi-repeat RNA targeting construct for manipulating an RNA target without introducing a nuclease protein, said construct comprising three or more distinct guide nucleotide sequences that are complementary to the same RNA target, wherein each guide nucleotide sequence consists of a single-stranded antisense nucleotide fragments of 100 nt or less, wherein said single-stranded antisense nucleotide fragments are not self-complementary and do not form double-stranded structures with themselves, said system being free of constructs comprising nuclease-encoding nucleotide sequences or nuclease protein.

2. The system of claim 1, wherein each guide nucleotide sequence consists of a single-stranded antisense nucleotide fragment of 15 nt to 100 nt.

3. The system of claim 1, wherein each guide nucleotide sequence consists of a single-stranded antisense nucleotide fragment of 80 nt or less.

4. The system of claim 1, wherein each guide nucleotide sequence consists of a single-stranded antisense nucleotide fragment of 50 nt or less.

5. The system of claim 1, wherein each guide nucleotide sequence consists of a single-stranded antisense nucleotide fragment of 22 nt to 30 nt.

6. The system of claim 1, wherein said guide nucleotide sequences are guide RNA (crRNA) or DNA encoding for the guide RNA, which are capable of binding or hybridizing to the RNA target.

7. The system of claim 1, wherein the RNA target is a coding sequence selected from mRNA or pre-mRNA, or a non-coding sequence selected from ncRNA, IncRNA, tRNA, or rRNA.

8. The system of claim 1, wherein said guide nucleotide sequences each bind to a different region of the same RNA target.

9. The system of claim 1, wherein each of said three or more distinct guide nucleotide sequences are:

directly linked on a single expression cassette; or indirectly linked on a single expression cassette, such that each guide nucleotide sequence is separated by an intervening sequence on said expression cassette.

10. The system of claim 9, wherein said single expression cassette is a homogenous multimer wherein each of said three or more distinct guide nucleotide sequences consists of the same sequence and has complementarity with the same region of the same RNA target.

11. The system of claim 10, wherein said homogenous multimer comprises up to eight repeats of the same guide nucleotide sequence.

12. The system of claim 9, wherein said single expression cassette is a heterogenous multimer wherein each of said three or more distinct guide nucleotide sequences consists of different sequences having complementarity with different regions of the same RNA target.

13. The system of claim 9, wherein said expression cassette comprises at least one regulatory element adjacent said three or more distinct guide nucleotide sequences.

14. A composition for manipulation of RNA targets without introducing a nuclease protein, said composition comprising a system comprising plurality of short multi-repeat RNA targeting constructs according to claim 1 dispersed in a carrier or vehicle, wherein said composition is free of nuclease-encoding nucleotide sequence or nuclease protein.

15. A method of modifying an RNA target without introducing a nuclease protein, said method comprising delivering to said RNA target a system comprising a short multi-repeat RNA targeting construct according to claim 1 without introducing a nuclease-encoding nucleotide sequence or nuclease protein.

16. A method of gene silencing without introducing a nuclease protein, the method comprising delivering to a cell, tissue, organ, or organism, a system comprising a short multi-repeat RNA targeting construct according to claim 1 without introducing a nuclease-encoding nucleotide sequence or nuclease protein, wherein at least one of said two or more distinct guide nucleotide sequences is complementary to an RNA target associated with said gene.

17. A method of manipulating a plant characteristic without introducing a nuclease protein, said method comprising delivering to a plant cell, tissue, or plant a system comprising a short multi-repeat RNA targeting construct according to claim 1 without introducing a nuclease-encoding nucleotide sequence or nuclease protein, wherein at least one of said three or more distinct guide nucleotide sequences is complementary to an RNA target associated with a gene encoding for said plant characteristic.

18. A seed, seedling, or progeny of a plant produced according to the method of claim 17, wherein said seed, seedling, or progeny expresses said short multi-repeat RNA targeting construct without a bacterial nuclease protein.

19. The system of claim 12, said expression cassette further comprising three or more additional distinct guide nucleotide sequences having complementarity with a different RNA target.

* * * * *